US010711061B2

(12) United States Patent
Morsey et al.

(10) Patent No.: US 10,711,061 B2
(45) Date of Patent: *Jul. 14, 2020

(54) ANTIBODIES AGAINST CANINE PD-1

(71) Applicant: Intervet Inc., Madison, NJ (US)

(72) Inventors: Mohamad Morsey, Omaha, NE (US); Yuanzheng Zhang, Edison, NJ (US); Denise Bartels-Morozov, Fremont, NE (US); Jason Erskine, Omaha, NE (US); Ian Tarpey, St. Ives (GB)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/894,493

(22) Filed: Feb. 12, 2018

(65) Prior Publication Data
US 2018/0251554 A1 Sep. 6, 2018

Related U.S. Application Data

(63) Continuation of application No. 15/104,844, filed as application No. PCT/EP2014/078655 on Dec. 19, 2014, now Pat. No. 9,944,704.

(60) Provisional application No. 62/030,812, filed on Jul. 30, 2014, provisional application No. 61/918,847, filed on Dec. 20, 2013, provisional application No. 61/918,946, filed on Dec. 20, 2013.

(51) Int. Cl.
*C07K 16/28* (2006.01)
*A61K 39/00* (2006.01)
*A61P 37/04* (2006.01)
*A61K 39/395* (2006.01)

(52) U.S. Cl.
CPC .......... *C07K 16/2803* (2013.01); *A61K 39/00* (2013.01); *A61K 39/3955* (2013.01); *A61P 37/04* (2018.01); *C07K 16/2818* (2013.01); *C07K 16/2896* (2013.01); *A61K 2039/55516* (2013.01); *C07K 2317/24* (2013.01); *C07K 2317/34* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,005,079 A | 12/1999 | Casterman et al. |
| 6,703,360 B2 | 3/2004 | McCall et al. |
| 6,808,710 B1 | 10/2004 | Wood et al. |
| 6,936,704 B1 | 8/2005 | Freeman et al. |
| 7,038,013 B2 | 5/2006 | Freeman et al. |
| 7,101,550 B2 | 9/2006 | Wood et al. |
| 7,105,328 B2 | 9/2006 | Wood et al. |
| 7,261,890 B2 | 8/2007 | Krah, III et al. |
| 7,432,059 B2 | 10/2008 | Freeman et al. |
| 7,595,048 B2 | 9/2009 | Honjo et al. |
| 7,635,757 B2 | 12/2009 | Freeman et al. |
| 7,638,492 B2 | 12/2009 | Wood et al. |
| 7,700,301 B2 | 4/2010 | Wood et al. |
| 7,709,214 B2 | 5/2010 | Freeman et al. |
| 7,722,868 B2 | 5/2010 | Freeman et al. |
| 7,807,158 B2 | 10/2010 | Endl et al. |
| 8,008,449 B2 | 8/2011 | Korman et al. |
| 8,337,842 B2 | 12/2012 | Hansen |
| 8,354,509 B2 | 1/2013 | Carven et al. |
| 8,569,460 B2 | 10/2013 | Hansen |
| 8,652,470 B2 | 2/2014 | Hansen |
| 8,735,553 B1 | 5/2014 | Li et al. |
| 9,067,999 B1 | 6/2015 | Honjo et al. |
| 9,580,496 B2 | 2/2017 | Gearing |
| 9,616,120 B2 | 4/2017 | Hansen |
| 9,790,280 B2 | 10/2017 | Rue et al. |
| 10,280,223 B2 | 5/2019 | Mizuno |
| 2002/0165135 A1 | 11/2002 | McCall et al. |
| 2007/0003546 A1 | 1/2007 | Lazar et al. |
| 2007/0148164 A1 | 6/2007 | Farrington et al. |
| 2010/0203056 A1 | 8/2010 | Irving |
| 2010/0266617 A1 | 10/2010 | Carven et al. |
| 2011/0318373 A1 | 12/2011 | Sasikumar et al. |
| 2012/0039906 A1 | 2/2012 | Olive |
| 2012/0237522 A1 | 9/2012 | Kang |

FOREIGN PATENT DOCUMENTS

| | | |
|---|---|---|
| EP | 1537878 | 6/2005 |
| EP | 1836226 B1 | 6/2011 |
| EP | 2705057 B1 | 3/2016 |
| JP | 2014140982 | 1/2016 |
| RU | 2457217 C2 | 7/2012 |
| WO | WO9404678 | 3/1994 |
| WO | WO9425591 | 11/1994 |
| WO | 1999051642 A1 | 10/1999 |
| WO | WO2003042402 | 5/2003 |
| WO | 2008076255 A2 | 6/2008 |

(Continued)

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*
Simonyan, L. et al., Confirmational Epitope Mapping by Cross-Link Mass Spectrometry: Analysis of Ipilimumab, Nivolumab and Pembrolizumab, 2017, Retrieved from the Internet a: URL: https://covalx.com/pdf/171113-CovalX-XLMS%20Xray%20Comparions-PEGSEU17.pdf, XP055516470.
Baudino et al., Crucial Role of aspartic acid at position 265 in the CH2 domain for muri e IgG2a and IgG2b Fc-assiciated effector functions, J. Immunology, 2008, pp. 6664-6669, vol. 181.

(Continued)

*Primary Examiner* — Nelson B Moseley, II

(57) ABSTRACT

The present invention discloses antibodies to canine PD-1 that have specific sequences and a high binding affinity for canine PD-1. The invention also discloses the use of the antibodies of the present invention in the treatment of cancer in dogs.

17 Claims, 12 Drawing Sheets

Specification includes a Sequence Listing.

(56) References Cited

FOREIGN PATENT DOCUMENTS

| | | |
|---|---|---|
| WO | WO2008083174 A2 | 7/2008 |
| WO | WO2008156712 | 12/2008 |
| WO | 2010027488 A2 | 3/2010 |
| WO | 2010110838 A2 | 9/2010 |
| WO | 2010117448 A2 | 10/2010 |
| WO | WO2010117760 A2 | 10/2010 |
| WO | WO2012135408 | 10/2012 |
| WO | 2012153121 A1 | 11/2012 |
| WO | 2012153122 A1 | 11/2012 |
| WO | 2012153123 A1 | 11/2012 |
| WO | 2012153126 A1 | 11/2012 |
| WO | 2013030568 A1 | 3/2013 |
| WO | 2013034900 A1 | 3/2013 |
| WO | 2013054127 A1 | 4/2013 |
| WO | 2013063186 A2 | 5/2013 |
| WO | WO2013124666 A1 | 8/2013 |
| WO | 2015091910 A2 | 6/2015 |
| WO | 2015091914 | 6/2015 |
| WO | WO2016006241 | 1/2016 |

OTHER PUBLICATIONS

Dorai, H et al., Aglycosylated chimeric mouse/human IgG1 antibody retains some effector function, Hybridoma, 1991, pp. 211-217, 10(2).

Lund et al., J. Immunol., J. Immunol., 1996, pp. 4963-4969, 157.

Mimura, Y et al., Glycosylation engineering of therapeutic IgG antibodies: challenges for the safety, functionality and efficacy, Protein Cell, 2018, pp. 47-62, 9(1).

Tao et al., J. Immunol., Journal of Immunology, 1989, pp. 2595-2601, 143.

Folkl, A et al, Feline programmed death and its ligand: Characterization and changes with feline immunodeficiency virus infection, Veterinary Immunology and Immunopathology, 2010, 107-114, 134.

Amgen vs. Sanofi and Regeneron, Case 17-1480, Document 176, filed Feb. 6, 2018, United States Court of Appeals for the Federal Circuit, Response to Petition for Rehearing En Banc, 27 pages.

Atherton, MJ et al., Cancer immunology and canine malignant melanoma: A comparative review, Veterinary Immunology and Immunopathology, 2016, pp. 15-26, 169.

Brown, Mckay et al., Tolerance of single, but not multiple, amino acid replacements in antibody VH CDR 2: a means of minimizing B cell wastage from somatic hypermutation?, The Journal of Immunology, 1996, 3285-3291, 156 (9).

Ching Chen et al., Enhancement and destruction of antibody function by somatic mutation: unequal occurrence is controlled by V gene combinatorial associations, The EMBO Journal, 1995, 2784-2794, 14-12.

Pakula, Andrew A., Genetic Analysis of Protein Stability and Function, Annu. Rev. Genet., 1989, 289-310, 23.

U.S. Appl. No. 15/104,844, filed Jun. 15, 2016.

Al-Lazikani, Standard Conformations for the Canonical Structures of Immunoglobulins, J. Mol. Biol., 1997, 927-948, 273.

Alegre, A non-activating "humanized" anti-CD3 monoclonal antibody retains immunosuppressive properties in vivo, Transplantation, 1994, 1537-1543, 57.

Barber et al., Restoring function in exhausted CD8 T cells during chronic viral infection, Nature, 2006, pp. 682-687, vol. 439.

Bendig, Mary E., humanization of Rodent Monoclonal Antibodies by CDR Grafting, Methods: A companion to methods in Enzymology, 1993, 83-93, 8.

Bergeron et al., Comparative functional characterization of canine IgG subclasses, Veterinary Immunology and Immunopathology, 2014, pp. 31-41, 157, WO.

Berglund, L et al., The epitope space of the human proteome, Protein Science, 2008, pp. 606-613, 17.

Brown, Blockade of Programmed Death-1 Ligands on Dendritic Cells Enhances T Cell Activation and Cytokine Production, J. Immunol., 2003, pp. 1257-1266, vol. 170.

Chan et al., Therapeutic antibodies for autoimmunity and inflammation, The Journal of Immunology, 2010, pp. 301-316, 10-5, WO.

Chothia et al, Canonical Structures for the Hypervariable Regions of Immunoglobins, J. Mol. Biol., 1987, 901-917, 196.

Chothia et al., Conformations of immunoglobin hypervariable regions, Nature, 1989, 877-883, 342.

Cobbold, et al., The immunology of companion animals: reagents and therapeutic strategies with potential veterinary and human clinical applications, Immunology Today, 1994, pp. 347-353, 15-8.

Colman, Effects of amino acid sequence changes on antibody-antigen interactions, Research Immunology, 1994, 33-36, 145.

Dong et al., Tumor-associated B7-H1 promotes T-cell apoptosis: A potential mechanism of immune evasion, Nature Medicine, 2002, pp. 793-800, vol. 8(8).

Esch, et al., Programmed Death 1-Mediated T Cell Exhaustion during Visceral Leishmaniasis Impairs Phagocyte Functioni, The Journal of Immunology, 2013, pp. 5542-5550, 191, WO.

Gearing, DP et al., A fully caninised anti-NGF monoclonal antibody for pain relief in dogs, BMC Veterinary Research, 2013, pp. 1-11, vol. 9 (226), WO.

Geczy, T et. al., Molecular basis for failure of "Atypical" C1 domain of Vav1 to bind diacylglycerol/phorbol ester, The Journal of Biological Chemistry, 2012, pp. 13137-13158, 287(16).

Hutchins, Improved bio distribution, tumor targeting and reduced immunogenicity in mice with a gamma 4 variant of CAMPATH-1H, Proc. Natl. Acad. Sci. USA, 1995, pp. 11980-11984, 92.

Ikebuchi et al., Blockade of bovine PD-1 increases T cell funtion and inhibits bovine leukemia virus expression in B cells in vitro, Veterinary Research, 2013, 1-15, 44-59.

International Search Report for PCT/EP2014/078653 dated Jul. 6, 2015, 8 pages.

International Search report for PCT/EP2014/078665 dated Jul. 23, 2015, 20 pages.

International Search Report for PCT/EP2015/078655 dated Aug. 13, 2015, 28 pages.

Iwai, Involvement of PD-L1 on tumor cells in the escape from host immune system and tumor immunotherapy by PD-L1 blockade, Proc. Natl. Acad. Sci. USA, 2002, pp. 12293-12297, vol. 99.

Jackson, et al., In Vitro Antibody Maturation, Improvement of a High Affinity, Neutralizing Antibody Against IL-1Beta, The Journal of Immunology, 1995, pp. 3310-3319, 154, WO.

Kabat, The Structural Basis of Antibody Complementarity, Adv. Prot. Chem., 1978, 1-75, 32.

Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.

Khantasup, K et al., Design and generation of humanized single-chain Fv derived from mouse hybridoma for potential targeting application, Monoclonal antibodies, 2015, pp. 404-417, 34(6).

Lin, The PD-1/PD-L1 complex resembles the antigen-binding Fv domains of antibodies and T cell receptors, Proc. Natl. Acad. Sci. USA, 2008, pp. 3011-3016, vol. 105.

Lin, Y et al., Improved affinity of a chicken single-chain antibody to avian infectious bronchitis virus by site-detected mutagenesis of complementarity-determing region H3, African journal of biotechnology, 2011, pp. 18294-18302, 10(79).

Lyford-Pike, et al., Evidence for a Role of the PD-1:PD-L1 Pathway in Immune Resistance of HPV-Associated Head and Neck Squamous Cell Carcinoma, Cancer Research, 2012, pp. 1733-1741, 73-6, WO.

Mariuzza, RA et al., The structural basis of antigen-antibody recognition, Ann. Rev. Biophys. Biophys. Chem., 1987, pp. 139-159, 16.

Mccarthy, BJ et al., Altering the fine specificity of an anti-legionella single chain antibody by a single amino acid insertion, Journal of Immunological Methods, 2001, pp. 137-149, 251.

Mcdermott, et al., PD-1 as a potential target in cancer therapy, Cancer Medicine, 2013, pp. 662-673, WO.

Mcearchern, Engineered anti-CD70 antibody with multiple effector functions exhibits in vitro and in vivo antitumor activities, Blood, 2007, 1185-1192, 109.

(56) References Cited

OTHER PUBLICATIONS

Muyldermans, Recognition of antigens by single-domain antibody fragments: the superfluous luxury of paired domains, Trends Biochem. Sci., 2001, 230-235, 26.

National Service Foundation Award Abstract #1262435, ABI Innovation: Predicting the combined impact of multiple mutations on protein functional adaptation, 2012, 2 pages.

NCBI Reference Sequence: XP_543338.3, Sep. 24, 2013, XP055179334, retrieved from Internet: URL:http://www.ncbi.nlm.nih.gov/protein/XP_543338.

Nomi et al., Clinical Significance and Therapeutic Potential of the Programmed Death-1 Ligand/Programmed Death-1 Pathway in Human Pancreatic Cancer, Clinical Cancer Research, 2007, pp. 2151-2157, vol. 13.

Okazaki, PD-1 and PD-1 ligands: from discovery to clinical application, Int. Immunol., 2007, pp. 813-824, vol. 19.

Paul, WE, Fundamental Immunology, Fundamental Immunolgy, third edition, 1993, 292-295, Third Edition.

Reichmann, Single domain antibodies: comparison of camel VH and camelised human VH domains, J. Immunol. Methods, 1999, 25-38, 231.

Roguin, LP et al., Monoclonal antibodies inducing conformational changes on the antigen molecule, Scandinaavian Journal of Immunology, 2003, pp. 387-394, 58.

Rudikoff, Single amino acid substitution altering antigen-binding specificity, Proc. Natl. Acad. Sci. USA, 1982, pp. 1979-1983, vol. 79.

Sazinsky, Aglycosylated immunoglobin G1 variants productively engage activating Fc receptors, Proc. Natl. Acad. Sci., 2008, 20167-20172, 105.

Shields, High Resolution Mapping of the Binding Site on Human IgG1 for FcyRI, FcyRII, FcyRIII, and FcRn and Design of IgG1 Variants with Improved Binding to the FeyR, J. of Biol. Chem., 2001, 6591-6604, 276-9.

Strome et al., B7-H1 Blockade Augments Adoptive T-Cell Immunotherapy for Squamous Cell Cancinoma, Cancer Research, 2003, pp. 6501-6505, vol. 63.

Tang et al., Cloning and characterization of cDNAs encoding four different canine immunoglobulin Y chains, Veterinary Immunology and Immunopathology, 2001, pp. 259-270, 80.

Thompson et al., PD-1 Is Expressed by Tumor-Infiltrating Immune Cells and Is Associated with Poor Outcome for Patients with Renal Cell Carcinoma, Clinical Cancer Research, 2007, pp. 1757-1761, vol. 15.

Thompson et al., Tumor B7-H1 Is Associated with Poor Prognosis in Renal Cell Carcinoma Patients with Long-Term Follow-up, Cancer Res., 2006, pp. 3381-3385, vol. 66.

Tsushima et al., Predominant expression of B7-H1 and its immunoregulatory roles in oral squamous cell carcinoma, Oral Oncol., 2006, pp. 268-274, vol. 42.

Tzartos, SJ, Epitope mapping by antibody competition, Methods in Molecular Biology, 1996, pp. 55-66, 66.

Wintterle et al., Expression of the B7-Related Molecule B7-H1 by Glioma Cells: A Potential Mechanism of Immune Paralysis, Cancer Res., 2003, pp. 7462-7467, vol. 63.

Wong, et al., Structural Requirements for a Specificity Switch and for Maintenance of Affinity Using Mutational Analysis of a Phage-Displayed Anti-Arsonate Antibody of Fab Heavy Chain First Complementarity-Determining Region, Journal of Immunology, 1998, pp. 5990-5997, 160, WO.

Zhang et al., Structural and Functional Analysis of the Costimulatory Receptor Programmed Death-1, Immunity, 2004, pp. 337-347, vol. 20.

* cited by examiner

Alignment of canine IgGB CHs lacking ADCC function cIgGB wt          SASTTAPSVFPLAPSCGSTSGSTVALACLVSGYFPEPVTVSWNSGSLTSGVHTFPSVLQSSGLYSLSSMVTVPSSRWPSETFTCNVAHPASTKVDKPVPKRENGRVPRPPDCPKCPAPE
cIgGB(+)A-hinge   SASTTAPSVFPLAPSCGSTSGSTVALACLVSGYFPEPVTVSWNSGSLTSGVHTFPSVLQSSGLYSLSSMVTVPSSRWPSETFTCNVAHPASTKVDKPVFNEC----PCTDTPPCPAPE
cIgGB(+)D-hinge   SASTTAPSVFPLAPSCGSTSGSTVALACLVSGYFPEPVTVSWNSGSLTSGVHTFPSVLQSSGLYSLSSMVTVPSSRWPSETFTCNVAHPASTKVDKPVPK---ES----TCKCISPCPAPE
cIgGB(-)ADCC      SASTTAPSVFPLAPSCGSTSGSTVALACLVSGYFPEPVTVSWNSGSLTSGVHTFPSVLQSSGLYSLSSMVTVPSSRWPSETFTCNVAHPASTKVDKPVPKRENGRVPRPPDCPKCPAPE cIgGB             MLGGPSVFIFPPKPKDTLLIARTPEVTCVVVDLDPEDPEVQISWFVDGKQMQTAKTQPREEQFNGTYRVVSVLPIGHQDWLKGKQFTCKVNNKALPSPIERTISKARGQAHQPSVYVLPP
cIgGB(+)A-hinge   MLGGPSVFIFPPKPKATLLIARTPEVTCVVVDLDPEDPEVQISWFVDGKQMQTAKTQPREEQFAGTYRVVSVLPIGHQDWLKGKQFTCKVNNKALPSPIERTISKARGQAHQPSVYVLPP
cIgGB(+)D-hinge   MLGGPSVFIFPPKPKATLLIARTPEVTCVVVDLDPEDPEVQISWFVDGKQMQTAKTQPREEQFAGTYRVVSVLPIGHQDWLKGKQFTCKVNNKALPSPIERTISKARGQAHQPSVYVLPP
cIgGB(-)ADCC      MLGGPSVFIFPPKPKATLLIARTPEVTCVVVDLDPEDPEVQISWFVDGKQMQTAKTQPREEQFAGTYRVVSVLPIGHQDWLKGKQFTCKVNNKALPSPIERTISKARGQAHQPSVYVLPP canIgGB           SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK
cIgGB(+)A-hinge   SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK
cIgGB(+)D-hinge   SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK
cIgGB(-)ADCC      SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK

FIG.8A cIgGB wt

SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENGRVPRPPDCPKCPAPEMLGGPSVFIFPPKPKDT
LLIARTPEVTCVVVDLDPEDPEVQISWFVDGKQMQTAKTQPREEQFNGTYRVVSVLPIGHQDWLKGKQFTCKVNNKALPSPIERTISKARGQAHQPSVYVLPPSREELSKNTVSLTCLIKDFFPPDIDVEWQSNGQQ
EPESKYRTTPPQLDEDGSYFLYSKLSVDKSRWQRGDTFICAVMHEALHNHYTQESLSHSPGK cIgGB(+)A-hinge SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVFNECRCTDTPPCPAPEMLGGPSVFIFPPKPKATLLIAR
TPEVTCVVVDLDPEDPEVQISWFVDGKQMQTAKTQPREEQFAGTYRVVSVLPIGHQDWLKGKQFTCKVNNKALPSPIERTISKARGQAHQPSYVLPPSREELSKNTVSLTCLIKDFFPPDIDVEWQSNGQQEPESK
YRTTPPQLDEDGSYFLYSKLSVDKSRWQRGDTFICAVMHEALHNHYTQESLSHSPGK cIgGB(+)D-hinge SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKESTCKCISPCPAPEMLGGPSVFIFPPKPKATLLIAR
TPEVTCVVVDLDPEDPEVQISWFVDGKQMQTAKTQPREEQFAGTYRVVSVLPIGHQDWLKGKQFTCKVNNKALPSPIERTISKARGQAHQPSYVLPPSREELSKNTVSLTCLIKDFFPPDIDVEWQSNGQQEPESK
YRTTPPQLDEDGSYFLYSKLSVDKSRWQRGDTFICAVMHEALHNHYTQESLSHSPGK cIgGB(-)ADCC SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENGRVPRPPDCPKCPAPEMLGGPSVFIFPPKPKAT
LLIARTPEVTCVVVDLDPEDPEVQISWFVDGKQMQTAKTQPREEQFAGTYRVVSVLPIGHQDWLKGKQFTCKVNNKALPSPIERTISKARGQAHQPSVYVLPPSREELSKNTVSLTCLIKDFFPPDIDVEWQSNGQQ
EPESKYRTTPPQLDEDGSYFLYSKLSVDKSRWQRGDTFICAVMHEALHNHYTQESLSHSPGK

FIG. 8B

ANTIBODIES AGAINST CANINE PD-1

CROSS-REFERENCE TO RELATED APPLICATIONS

This application is a Continuation of U.S. application Ser. No. 15/104,844 filed on Jun. 15, 2016, which is a national stage entry under 35 U.S.C. § 371 of PCT/EP2014/078655, filed on Dec. 19, 2014, which claims priority to U.S. Provisional Application No. 61/918,946, filed on Dec. 20, 2013, U.S. Provisional Application No. 61/918,847, filed on Dec. 20, 2013, and U.S. Provisional Application No. 62/030,812, filed Jul. 30, 2014. The contents of all of which are hereby incorporated by reference in their entireties.

FIELD OF THE INVENTION

The present invention relates to murine antibodies to canine PD-1 that have specific sequences and a high binding affinity for canine PD-1. The invention also relates to use of the antibodies of the present invention in the treatment of cancer in dogs.

BACKGROUND OF THE INVENTION

An immunoinhibitory receptor that is primarily expressed on activated T and B cells, Programmed Cell Death Receptor 1, also referred to as Programmed Death Receptor 1 (PD-1), is a member of the immunoglobulin superfamily related to CD28 and CTLA-4. PD-1 and like family members are type I transmembrane glycoproteins containing an extracellular Ig Variable-type (V-type) domain that binds its ligands and a cytoplasmic tail that binds signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

PD-1 attenuates T-cell responses when bound to Programmed Cell Death Ligand 1, also referred to as Programmed Death Ligand 1 (PD-L1), and/or Programmed Cell Death Ligand 2, also referred to as Programmed Death Ligand 2 (PD-L2). The binding of either of these ligands to PD-1 negatively regulates antigen receptor signaling. Blocking the binding of PD-L1 to PD-1 enhances tumor-specific CD8$^+$ T-cell immunity, while aiding the clearance of tumor cells by the immune system. The three-dimensional structure of murine PD-1, as well as the co-crystal structure of mouse PD-1 with human PD-L1 have been reported [Zhang et al., Immunity 20: 337-347 (2004); Lin et al., *Proc. Natl. Acad. Sci. USA* 105: 3011-3016 (2008)].

PD-L1 and PD-L2 are type I transmembrane ligands that contain both IgV- and IgC-like domains in the extracellular region along with short cytoplasmic regions with no known signaling motifs. Both PD-L1 and PD-L2 are either constitutively expressed or can be induced in a variety of cell types, including non-hematopoietic tissues as well as various tumor types. PD-L1 is not only expressed on B, T, myeloid and dendritic cells (DCs), but also on peripheral cells, such as microvascular endothelial cells and non-lymphoid organs e.g., heart or lung. In contrast, PD-L2 is only found on macrophages and DCs. The expression pattern of PD-1 ligands suggests that PD-1 plays a role in maintaining peripheral tolerance and may further serve to regulate self-reactive T- and B-cell responses in the periphery.

In any case, it is now abundantly clear that PD-1 plays a critical role in at least certain human cancers, presumably by mediating immune evasion. Accordingly, PD-L1 has been shown to be expressed on a number of mouse and human tumors and is inducible by IFN gamma in the majority of PD-L1 negative tumor cell lines [Iwai et al., *Proc. Natl. Acad. Sci. U.S.A.* 99: 12293-12297 (2002); Strome et al., *Cancer Res.*, 63: 6501-6505 (2003)]. Furthermore, the expression of PD-1 on tumor infiltrating lymphocytes and/or PD-L1 on tumor cells has been identified in a number of primary human tumor biopsies. Such tumor tissues include cancers of the lung, liver, ovary, cervix, skin, colon, glioma, bladder, breast, kidney, esophagus, stomach, oral squamous cell, urothelial cell, and pancreas, as well as tumors of the head and neck [Brown et al., *J. Immunol.* 170: 1257-1266 (2003); Dong et al., *Nat. Med.* 8: 793-800 (2002); Wintterle et al., *Cancer Res.* 63: 7462-7467 (2003); Strome et al., *Cancer Res.*, 63: 6501-6505 (2003); Thompson et al., *Cancer Res.* 66: 3381-5 (2006); Thompson et al., *Clin. Cancer Res.* 13: 1757-1761 (2007); Nomi et al., *Clin. Cancer Res.* 13: 2151-2157. (2007)]. More strikingly, PD-ligand expression on tumor cells has been correlated to poor prognosis of human cancer patients across multiple tumor types [reviewed in Okazaki and Honjo, *Int. Immunol.* 19: 813-824 (2007)].

Moreover, Nomi et al. [*Clin. Cancer Res.* 13: 2151-2157 (2007)] demonstrated the therapeutic efficacy of blocking the binding of PD-L1 to PD-1 in a murine model of aggressive pancreatic cancer through administering either PD-1 or PD-L1 directed antibody. These antibodies effectively promoted tumor reactive CD8$^+$ T cell infiltration into the tumor resulting in the up-regulation of anti-tumor effectors including IFN gamma, granzyme B, and perforin. Similarly, the use of antibodies to block the binding of PD-L1 and PD-1 significantly inhibited tumor growth in a model of mouse squamous cell carcinoma [Tsushima et al., *Oral Oncol.* 42: 268-274 (2006)].

In other studies, transfection of a murine mastocytoma line with PD-L1 led to decreased lysis of the tumor cells when co-cultured with a tumor-specific CTL clone. Lysis was restored when anti-PD-L1 monoclonal antibody was added [Iwai et al., *Proc. Natl. Acad. Sci. U.S.A.* 99: 12293-12297 (2002)]. In vivo, blocking the PD1/PD-L1 interaction was shown to increase the efficacy of adoptive T cell transfer therapy in a mouse tumor model [Strome et al., *Cancer Res.* 63: 6501-6505 (2003)]. Further evidence for the role of PD-1 in cancer treatment comes from experiments performed with PD-1 knockout mice in which PD-L1 expressing myeloma cells grew only in wild-type animals (resulting in tumor growth and associated animal death), but not in PD-1 deficient mice [Iwai Y. et al., *Proc. Natl. Acad. Sci. U.S.A.* 99: 12293-12297 (2002)]. More recently, antibodies against PD-1 (including humanized murine monoclonal antibodies against human PD-1) have shown at least initial success in cancer therapy in humans [see e.g., U.S. Pat. No. 8,354,509 B2, U.S. Pat. No. 8,008,449 B2, and U.S. Pat. No. 7,595,048 B2].

Anti-PD-1 antibodies may also be useful in chronic viral infection. Memory CD8$^+$ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. [*Nature* 439: 682-687 (2006)] showed that mice infected with a laboratory strain of LCMV developed chronic infection resulted in high levels of virus in the blood and other tissues. These mice initially developed a robust T cell response, but eventually succumbed to the infection upon T cell exhaustion. Barber et al. found that the decline in number and function of the effector T cells in chronically infected mice could be reversed by injecting an antibody that blocked the interaction between PD-1 and PD-L1.

The citation of any reference herein should not be construed as an admission that such reference is available as "prior art" to the instant application.

SUMMARY OF THE INVENTION

The present invention relates to anti-canine PD-1 antibodies that have a high binding affinity to canine PD-1, as well as have the ability to block the binding of canine PD-1 to canine PD-L1. In particular embodiments such anti-canine PD-1 antibodies are murine anti-canine PD-1 antibodies. In particular embodiments the anti-canine PD-1 antibodies have a high binding affinity to canine PD-1, as well as have the ability to also block the binding of canine PD-1 to canine PD-L2.

Moreover, the present invention relates to the complementary determining regions (CDRs) comprised by these antibodies and the combination of these CDRs (e.g., obtained from murine anti-canine PD-1 antibodies) into canine frames to form caninized anti-canine PD-1 antibodies. The present invention also relates to use of such antibodies in the treatment of disease such as cancer and/or those due to infections.

Accordingly, the present invention provides unique sets of CDRs from seven exemplified murine anti-canine PD-1 antibodies. Although each of the seven exemplified murine anti-canine PD-1 antibodies have a unique set of CDRs, i.e., three light chain CDRs: CDR light 1 (CDRL1), CDR light 2 (CDRL2), and CDR light 3 (CDRL3) and three heavy chain CDRs CDR heavy 1 (CDRH1), CDR heavy 2 (CDRH2) and CDR heavy 3 (CDRH3), as detailed below, there is substantial sequence homology within each group of CDRs, e.g., the set of CDRL1s. Therefore, the present invention not only provides the amino acid sequences of the six CDRs from seven exemplified murine anti-canine PD-1 antibodies, but further provides conservatively modified variants of those CDRs, as well as variants that comprise (e.g., share) the same canonical structure and/or bind to one or more (e.g., 1 to 4, or even all) amino acid residues of canine PD-1 that are comprised by an epitope of canine PD-1.

Therefore, the present invention provides an antibody or antigen binding fragment thereof that binds canine Programmed Death Receptor 1 (canine PD-1) with specificity comprising a light chain complementary determining region 1 (VL CDR1) that comprises the amino acid sequence of SEQ ID NO: 13, SEQ ID NO: 14, or SEQ ID NO: 15, and/or a light chain complementary determining region 2 (VL CDR2) comprising the amino acid sequence of SEQ ID NO: 16, SEQ ID NO: 17, SEQ ID NO: 18, SEQ ID NO: 19, SEQ ID NO: 20, or SEQ ID NO: 21, and/or a light chain complementary determining region 3 (VL CDR3) comprising the amino acid sequence of SEQ ID NO: 22, SEQ ID NO: 23, SEQ ID NO: 24, SEQ ID NO: 25, or SEQ ID NO: 26, and/or a heavy chain complementary determining region 1 (VH CDR1) in which the CDRH1 comprises the amino acid sequence of SEQ ID NO: 27, SEQ ID NO: 28, SEQ ID NO: 29, or SEQ ID NO: 30, and/or a heavy chain complementary determining region 2 (VH CDR2) comprising the amino acid sequence of SEQ ID NO: 31, SEQ ID NO: 32, SEQ ID NO: 33, SEQ ID NO: 34, or SEQ ID NO: 35, and/or a heavy chain complementary determining region 3 (VH CDR3) comprising the amino acid sequence of SEQ ID NO: 36, SEQ ID NO: 37, SEQ ID NO: 38, or SEQ ID NO: 114. In particular embodiments the antibody is a mammalian antibody. In more particular embodiments the antibody is a caninized antibody.

Accordingly, a caninized antibody of the present invention or antigen binding fragment thereof comprises one or more of the heavy chain complementary determining region 1 (VH CDR1) with an amino acid sequence of SEQ ID NO: 27, SEQ ID NO: 28, SEQ ID NO: 29, or SEQ ID NO: 30. In another embodiment, the heavy chain complementary determining region 2 (VH CDR2) comprises an amino acid sequence of SEQ ID NO: 31, SEQ ID NO: 32, SEQ ID NO: 33, SEQ ID NO: 34, or SEQ ID NO: 35. In still another embodiment the heavy chain complementary determining region 3 (VH CDR3) comprises an amino acid sequence of SEQ ID NO: 36, SEQ ID NO: 37, SEQ ID NO: 38, or SEQ ID NO: 114. In a particular embodiment of this type, the caninized antibody or antigen binding fragment comprises both a VH CDR1 comprising an amino acid sequence of SEQ ID NO: 27, SEQ ID NO: 28, SEQ ID NO: 29, or SEQ ID NO: 30 and a VH CDR2 comprising an amino acid sequence of SEQ ID NO: 31, SEQ ID NO: 32, SEQ ID NO: 33, SEQ ID NO: 34, or SEQ ID NO: 35. In another such embodiment, the caninized antibody or antigen binding fragment comprises both a VH CDR1 comprising an amino acid sequence of SEQ ID NO: 27, SEQ ID NO: 28, SEQ ID NO: 29, or SEQ ID NO: 30 and a VH CDR3 comprising an amino acid sequence of SEQ ID NO: 36, SEQ ID NO: 37, SEQ ID NO: 38, or SEQ ID NO: 114. In yet another such embodiment, the caninized antibody or antigen binding fragment comprises both a VH CDR2 comprising an amino acid sequence of SEQ ID NO: 31, SEQ ID NO: 32, SEQ ID NO: 33, SEQ ID NO: 34, or SEQ ID NO: 35 and a VH CDR3 comprising an amino acid sequence of SEQ ID NO: 36, SEQ ID NO: 37, SEQ ID NO: 38, or SEQ ID NO: 114. In still another such embodiment, the caninized antibody or antigen binding fragment comprises a VH CDR1 comprising an amino acid sequence of SEQ ID NO: 27, SEQ ID NO: 28, SEQ ID NO: 29, or SEQ ID NO: 30, a VH CDR2 comprising an amino acid sequence of SEQ ID NO: 31, SEQ ID NO: 32, SEQ ID NO: 33, SEQ ID NO: 34, or SEQ ID NO: 35, and a VH CDR3 comprising an amino acid sequence of SEQ ID NO: 36, SEQ ID NO: 37, SEQ ID NO: 38, or SEQ ID NO: 114.

In particular embodiments, the caninized antibody or antigen binding fragment also comprises a light chain complementary determining region 1 (VL CDR1) comprising an amino acid sequence of SEQ ID NO: 13, SEQ ID NO: 14, or SEQ ID NO: 15. In related embodiments the light chain complementary determining region 2 (VL CDR2) comprises an amino acid sequence of SEQ ID NO: 16, SEQ ID NO: 17, SEQ ID NO: 18, SEQ ID NO: 19, SEQ ID NO: 20, or SEQ ID NO: 21. In still another embodiment the light chain complementary determining region 3 (VL CDR3) comprises an amino acid sequence of SEQ ID NO: 22, SEQ ID NO: 23, SEQ ID NO: 24, SEQ ID NO: 25, or SEQ ID NO: 26. In a particular embodiment of this type, the caninized antibody or antigen binding fragment comprises both a VL CDR1 comprising an amino acid sequence of SEQ ID NO: 13, SEQ ID NO: 14, or SEQ ID NO: 15 and a VL CDR2 comprising an amino acid sequence of SEQ ID NO: 16, SEQ ID NO: 17, SEQ ID NO: 18, SEQ ID NO: 19, SEQ ID NO: 20, or SEQ ID NO: 21.

In other such embodiments, the caninized antibody or antigen binding fragment comprises both a VL CDR1 comprising an amino acid sequence of SEQ ID NO: 13, SEQ ID NO: 14, or SEQ ID NO: 15 and a VL CDR3 comprising an amino acid sequence of SEQ ID NO: 22, SEQ ID NO: 23, SEQ ID NO: 24, SEQ ID NO: 25, or SEQ ID NO: 26. In yet another such embodiments, the caninized antibody or antigen binding fragment comprises both a VL CDR2 comprising an amino acid sequence of SEQ ID NO: 16, SEQ ID NO: 17, SEQ ID NO: 18, SEQ ID NO: 19, SEQ ID NO: 20, or SEQ ID NO: 21 and a VL CDR3 comprising an amino acid sequence of SEQ ID NO: 22, SEQ ID NO: 23, SEQ ID NO: 24, SEQ ID NO: 25, or SEQ ID NO: 26. In still other such embodiments, the caninized antibody or antigen binding fragment comprises a VL CDR1 comprising an amino acid sequence of SEQ ID NO: 13, SEQ ID NO: 14, or SEQ ID NO: 15, a VL CDR2 comprising an amino acid sequence of SEQ ID NO: 16, SEQ ID NO: 17, SEQ ID NO: 18, SEQ ID NO: 19, SEQ ID NO: 20, or SEQ ID NO: 21, and a VL CDR3 comprising an amino acid sequence of SEQ ID NO: 22, SEQ ID NO: 23, SEQ ID NO: 24, SEQ ID NO: 25, or SEQ ID NO: 26.

In particular embodiments the caninized anti-canine PD-1 antibody further comprises complementary determining regions (CDRs) in which the CDRs have canonical structures of: H1-1, H2-1, and H3-6, respectively for CDR1, CDR2, and CDR3 of the heavy chain, i.e., CDR1 of the heavy chain has the canonical structure class 1, CDR2 of the heavy chain has the canonical structure class 1, and CDR3 of the heavy chain has the canonical structure class 6. In even more particular embodiments, the CDRs for the corresponding light chains have canonical structures of: L1-3, L2-1, and L3-1, respectively for CDR1, CDR2, and CDR3 of the light chain. In other embodiments the caninized anti-canine PD-1 antibody further comprises complementary determining regions (CDRs) in which the CDRs have canonical structures of: H1-1, H2-1, and H3-11, respectively for CDR1, CDR2, and CDR3 of the heavy chain. In even more particular embodiments of this type, the CDRs for the corresponding light chains have canonical structures of: L1-2A, L2-1, and L3-1, respectively for CDR1, CDR2, and CDR3 of the light chain. In still other embodiments the caninized anti-canine PD-1 antibody further comprises complementary determining regions (CDRs) in which the CDRs have canonical structures of: H1-1, H2-2A, and H3-11, respectively for CDR1, CDR2, and CDR3 of the heavy chain. In even more particular embodiments of this type, the CDRs for the corresponding light chains have canonical structures of: L1-2A, L2-1, and L3-1, respectively for CDR1, CDR2, and CDR3 of the light chain. In yet other embodiments the caninized anti-canine PD-1 antibody further comprises complementary determining regions (CDRs) in which the CDRs have canonical structures of: H1-1, H2-2A, and H3-13, respectively for CDR1, CDR2, and CDR3 of the heavy chain. In even more particular embodiments of this type, the CDRs for the corresponding light chains have canonical structures of: L1-4, L2-1, and L3-1, respectively for CDR1, CDR2, and CDR3 of the light chain.

Furthermore, the present invention provides antibodies to canine PD-1, e.g., monoclonal antibodies, that comprise variants of the CDRs of the present invention that have the corresponding canonical structures provided herein and that bind to the amino acid sequence of SEQ ID NO: 103. In particular embodiments of this type, the dissociation constant (Kd) for antibody-canine PD-1 binding is $1 \times 10^{-5}$ to $1 \times 10^{-12}$ M. In more particular embodiments the antibodies to canine PD-1, comprise variants of the CDRs of the present invention that have the corresponding canonical structures provided herein and bind to the amino acid sequence of SEQ ID NO: 104.

The present invention also provides an isolated caninized antibody or antigen binding fragment thereof that specifically binds Programmed Death Receptor 1 (PD-1) comprising a canine IgG heavy chain and a canine kappa or lambda light chain. In particular embodiments of this type, the canine kappa or lambda light chain that comprises three light chain complementary determining regions (CDRs): CDR light 1 (CDRL1), CDR light 2 (CDRL2), and CDR light 3 (CDRL3); and the canine IgG heavy chain comprises three heavy chain CDRs: CDR heavy 1 (CDRH1), CDR heavy 2 (CDRH2) and CDR heavy 3 (CDRH3) is obtained from the murine anti-canine PD-1 antibodies. Particular embodiments of the caninized antibodies and antigen binding fragments thereof of the present invention bind canine PD-1 and/or block the binding of canine PD-1 to canine Programmed Death Ligand 1 (PD-L1).

In specific embodiments, the present invention provides an isolated mammalian antibody or antigen binding fragment thereof that binds canine Programmed Death Receptor 1 (canine PD-1) with specificity comprising three light chain complementary determining regions (CDRs): CDR light 1 (CDRL1), CDR light 2 (CDRL2), and CDR light 3 (CDRL3); and three heavy chain CDRs: CDR heavy 1 (CDRH1), CDR heavy 2 (CDRH2) and CDR heavy 3 (CDRH3). In certain embodiments the CDRL1 comprises the amino acid sequence of SEQ ID NO: 13, a variant of SEQ ID NO: 13, a conservatively modified variant of SEQ ID NO: 13, a variant of SEQ ID NO: 13 that comprises the canonical structure class of 3, SEQ ID NO: 15, a variant of SEQ ID NO: 15, a conservatively modified variant of SEQ ID NO: 15, or a variant of SEQ ID NO: 15 that comprises the canonical structure class of 2A; the CDRL2 comprises the amino acid sequence of SEQ ID NO: 16, a variant of SEQ ID NO: 16, a conservatively modified variant of SEQ ID NO: 16, a variant of SEQ ID NO: 16 that comprises the canonical structure class of 1, SEQ ID NO: 18, a variant of SEQ ID NO: 18, a conservatively modified variant of SEQ ID NO: 18, a variant of SEQ ID NO: 18 that comprises the canonical structure class of 1, SEQ ID NO: 19, a variant of SEQ ID NO: 19, a conservatively modified variant of SEQ ID NO: 19, a variant of SEQ ID NO: 19 that comprises the canonical structure class of 1, SEQ ID NO: 20, a variant of SEQ ID NO: 20, a conservatively modified variant of SEQ ID NO: 20, a variant of SEQ ID NO: 20 that comprises the canonical structure class of 1, SEQ ID NO: 21, a variant of SEQ ID NO: 21, a conservatively modified variant of SEQ ID NO: 21, or a variant of SEQ ID NO: 21 that comprises the canonical structure class of 1, the CDRL3 comprises the amino acid sequence of SEQ ID NO: 22, a variant of SEQ ID NO: 22, a conservatively modified variant of SEQ ID NO: 22, or a variant of SEQ ID NO: 22 that comprises the canonical structure class of 1, SEQ ID NO: 24, a variant of SEQ ID NO: 24, a conservatively modified variant of SEQ ID NO: 24, a variant of SEQ ID NO: 24 that comprises the canonical structure class of 1, SEQ ID NO: 25, a variant of SEQ ID NO: 25, a conservatively modified variant of SEQ ID NO: 25, a variant of SEQ ID NO: 25 that comprises the canonical structure class of 1, SEQ ID NO: 26, a variant of SEQ ID NO: 26, a conservatively modified variant of SEQ ID NO: 26, or a variant of SEQ ID NO: 26 that comprises the canonical structure class of 1, the CDRH1 comprises the amino acid sequence of SEQ ID NO: 27, a variant of SEQ ID NO: 27, a conservatively modified variant of SEQ ID NO: 27, a variant of SEQ ID NO: 27 that comprises the canonical structure class of 1, SEQ ID NO: 29, a variant of SEQ ID NO: 29, a conservatively modified variant of SEQ ID NO: 29, a variant of SEQ ID NO: 29 that comprises the canonical structure class of 1, SEQ ID NO: 30, a variant of SEQ ID NO: 30, a conservatively modified variant of SEQ ID NO: 30, or a variant of SEQ ID NO: 30 that comprises the canonical structure class of 1, the CDRH2 comprises the amino acid sequence of SEQ ID NO: 31, a variant of SEQ ID NO: 31, a conservatively modified variant of SEQ ID NO: 31, or a variant of SEQ ID NO: 31 that comprises the canonical structure class of 1, SEQ ID NO: 33, a variant of SEQ ID NO: 33, a conservatively modified variant of SEQ ID NO: 33, a variant of SEQ ID NO: 33 that comprises the canonical structure class of 2A, SEQ ID NO: 34, a variant of SEQ ID NO: 34, a conservatively modified variant of SEQ ID NO: 34, a variant of SEQ ID NO: 34 that comprises the canonical structure class of 1, SEQ ID NO: 35, a variant of SEQ ID NO: 35, a conservatively modified variant of SEQ ID NO: 35, or a variant of SEQ ID NO: 35 that comprises the canonical structure class of 1, the CDRH3 comprises the amino acid sequence of SEQ ID NO: 36, a variant of SEQ ID NO: 36, a conservatively modified variant of SEQ ID NO: 36, a variant of SEQ ID NO: 35 that comprises the canonical structure class of 6, SEQ ID NO: 38, a variant of SEQ ID NO: 38, a conservatively modified variant of SEQ ID NO: 38, a variant of SEQ ID NO: 38 that comprises the canonical structure class of 11, SEQ ID NO: 114, a variant of SEQ ID NO: 114, a conservatively modified variant of SEQ ID NO: 114, or a variant of SEQ ID NO: 114 that comprises the canonical structure class of 11. In particular embodiments the antibody and antigen binding fragment thereof bind canine PD-1 and block the binding of canine PD-1 to canine Programmed Death Ligand 1 (PD-L1). In related embodiments the antibody also blocks the binding of canine PD-1 to canine Programmed Death Ligand 2 (PD-L2). In particular embodiments the isolated mammalian antibody is a caninized antibody. In more particular embodiments when bound to canine PD-1, the antibody or antigen binding fragment thereof binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104.

In other embodiments the CDRL1 comprises the amino acid sequence of SEQ ID NO: 13, a variant of SEQ ID NO: 13, a conservatively modified variant of SEQ ID NO: 13, or a variant of SEQ ID NO: 13 that comprises the canonical structure class of 3; the CDRL2 comprises the amino acid sequence of SEQ ID NO: 16, a variant of SEQ ID NO: 16, a conservatively modified variant of SEQ ID NO: 16, or a variant of SEQ ID NO: 16 that comprises the canonical structure class of 1; the CDRL3 comprises the amino acid sequence of SEQ ID NO: 22, a variant of SEQ ID NO: 22, a conservatively modified variant of SEQ ID NO: 22, or a variant of SEQ ID NO: 22 that comprises the canonical structure class of 1, the CDRH1 comprises the amino acid sequence of SEQ ID NO: 27, a variant of SEQ ID NO: 27, a conservatively modified variant of SEQ ID NO: 27, or a variant of SEQ ID NO: 27 that comprises the canonical structure class of 1; the CDRH2 comprises the amino acid sequence of SEQ ID NO: 31, a variant of SEQ ID NO: 31, a conservatively modified variant of SEQ ID NO: 31, and a variant of SEQ ID NO: 31 that comprises the canonical structure class of 1, the CDRH3 comprises the amino acid sequence of SEQ ID NO: 36, a variant of SEQ ID NO: 36, a conservatively modified variant of SEQ ID NO: 36, or a variant of SEQ ID NO: 36 that comprises the canonical structure class of 6. In particular embodiments when bound to canine PD-1, the antibody or antigen binding fragment thereof binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104. In more particular embodiments when bound to canine PD-1, the antibody or antigen binding fragment thereof binds to at least one amino acid residue within SEQ ID NO: 102.

In yet other embodiments the CDRL1 comprises the amino acid sequence of SEQ ID NO: 13, a variant of SEQ ID NO: 13, a conservatively modified variant of SEQ ID NO: 13, or a variant of SEQ ID NO: 13 that comprises the canonical structure class of 3; the CDRL2 comprises the amino acid sequence of SEQ ID NO: 19, a variant of SEQ ID NO: 19, a conservatively modified variant of SEQ ID NO: 19, or a variant of SEQ ID NO: 19 that comprises the canonical structure class of 1; the CDRL3 comprises the amino acid sequence of SEQ ID NO: 25, a variant of SEQ ID NO: 25, a conservatively modified variant of SEQ ID NO: 25, or a variant of SEQ ID NO: 25 that comprises the canonical structure class of 1, the CDRH1 comprises the amino acid sequence of SEQ ID NO: 27, a variant of SEQ ID NO: 27, a conservatively modified variant of SEQ ID NO: 27, or a variant of SEQ ID NO: 27 that comprises the canonical structure class of 1; the CDRH2 comprises the amino acid sequence of SEQ ID NO: 31, a variant of SEQ ID NO: 31, a conservatively modified variant of SEQ ID NO: 31, and a variant of SEQ ID NO: 31 that comprises the canonical structure class of 1, the CDRH3 comprises the amino acid sequence of SEQ ID NO: 36, a variant of SEQ ID NO: 36, a conservatively modified variant of SEQ ID NO: 36, or a variant of SEQ ID NO: 36 that comprises the canonical structure class of 6. In particular embodiments when bound to canine PD-1, the antibody or antigen binding fragment thereof binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104. In more specific embodiments when bound to canine PD-1, the antibodies or antigen binding fragments thereof bind to one or both amino acid residues $R_{75}$, and $R_{90}$ of SEQ ID NO: 2

In still other embodiments the CDRL1 comprises the amino acid sequence of SEQ ID NO: 13, a variant of SEQ ID NO: 13, a conservatively modified variant of SEQ ID NO: 13, or a variant of SEQ ID NO: 13 that comprises the canonical structure class of 3; the CDRL2 comprises the amino acid sequence of SEQ ID NO: 20, a variant of SEQ ID NO: 20, a conservatively modified variant of SEQ ID NO: 20, or a variant of SEQ ID NO: 20 that comprises the canonical structure class of 1; the CDRL3 comprises the amino acid sequence of SEQ ID NO: 25, a variant of SEQ ID NO: 25, a conservatively modified variant of SEQ ID NO: 25, or a variant of SEQ ID NO: 25 that comprises the canonical structure class of 1, the CDRH1 comprises the amino acid sequence of SEQ ID NO: 27, a variant of SEQ ID NO: 27, a conservatively modified variant of SEQ ID NO: 27, or a variant of SEQ ID NO: 27 that comprises the canonical structure class of 1; the CDRH2 comprises the amino acid sequence of SEQ ID NO: 34, a variant of SEQ ID NO: 34, a conservatively modified variant of SEQ ID NO: 34, and a variant of SEQ ID NO: 34 that comprises the canonical structure class of 1, the CDRH3 comprises the amino acid sequence of SEQ ID NO: 36, a variant of SEQ ID NO: 36, a conservatively modified variant of SEQ ID NO: 36, or a variant of SEQ ID NO: 36 that comprises the canonical structure class of 6. In particular embodiments when bound to canine PD-1, the antibody or antigen binding fragment thereof binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104.

In yet other embodiments the CDRL1 comprises the amino acid sequence of SEQ ID NO: 13, a variant of SEQ ID NO: 13, a conservatively modified variant of SEQ ID NO: 13, or a variant of SEQ ID NO: 13 that comprises the canonical structure class of 3; the CDRL2 comprises the amino acid sequence of SEQ ID NO: 16, a variant of SEQ ID NO: 16, a conservatively modified variant of SEQ ID NO: 16, or a variant of SEQ ID NO: 16 that comprises the canonical structure class of 1; the CDRL3 comprises the amino acid sequence of SEQ ID NO: 22, a variant of SEQ ID NO: 22, a conservatively modified variant of SEQ ID NO: 22, or a variant of SEQ ID NO: 22 that comprises the canonical structure class of 1, the CDRH1 comprises the amino acid sequence of SEQ ID NO: 30, a variant of SEQ ID NO: 30, a conservatively modified variant of SEQ ID NO: 30, or a variant of SEQ ID NO: 30 that comprises the canonical structure class of 1; the CDRH2 comprises the amino acid sequence of SEQ ID NO: 31, a variant of SEQ ID NO: 31, a conservatively modified variant of SEQ ID NO: 31, and a variant of SEQ ID NO: 31 that comprises the canonical structure class of 1, the CDRH3 comprises the amino acid sequence of SEQ ID NO: 36, a variant of SEQ ID NO: 36, a conservatively modified variant of SEQ ID NO: 36, or a variant of SEQ ID NO: 36 that comprises the canonical structure class of 6. In particular embodiments when bound to canine PD-1, the antibody binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104.

In still other embodiments the CDRL1 comprises the amino acid sequence of SEQ ID NO: 15, a variant of SEQ ID NO: 15, a conservatively modified variant of SEQ ID NO: 15, or a variant of SEQ ID NO: 15 that comprises the canonical structure class of 2A; the CDRL2 comprises the amino acid sequence of SEQ ID NO: 18, a variant of SEQ ID NO: 18, a conservatively modified variant of SEQ ID NO: 18, or a variant of SEQ ID NO: 18 that comprises the canonical structure class of 1; the CDRL3 comprises the amino acid sequence of SEQ ID NO: 24, a variant of SEQ ID NO: 24, a conservatively modified variant of SEQ ID NO: 24, or a variant of SEQ ID NO: 24 that comprises the canonical structure class of 1, the CDRH1 comprises the amino acid sequence of SEQ ID NO: 29, a variant of SEQ ID NO: 29, a conservatively modified variant of SEQ ID NO: 29, or a variant of SEQ ID NO: 29 that comprises the canonical structure class of 1; the CDRH2 comprises the amino acid sequence of SEQ ID NO: 33, a variant of SEQ ID NO: 33, a conservatively modified variant of SEQ ID NO: 33, and a variant of SEQ ID NO: 33 that comprises the canonical structure class of 1, the CDRH3 comprises the amino acid sequence of SEQ ID NO: 38, a variant of SEQ ID NO: 38, a conservatively modified variant of SEQ ID NO: 38, or a variant of SEQ ID NO: 38 that comprises the canonical structure class of 11. In particular embodiments when bound to canine PD-1, the antibody or antigen binding fragment thereof binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104. In more particular embodiments when bound to canine PD-1, the antibody or antigen binding fragment thereof binds to at least one amino acid residue within SEQ ID NO: 84.

In yet other embodiments the CDRL1 comprises the amino acid sequence of SEQ ID NO: 15, a variant of SEQ ID NO: 15, a conservatively modified variant of SEQ ID NO: 15, or a variant of SEQ ID NO: 15 that comprises the canonical structure class of 2A; the CDRL2 comprises the amino acid sequence of SEQ ID NO: 21, a variant of SEQ ID NO: 21, a conservatively modified variant of SEQ ID NO: 21, or a variant of SEQ ID NO: 21 that comprises the canonical structure class of 1; the CDRL3 comprises the amino acid sequence of SEQ ID NO: 26, a variant of SEQ ID NO: 26, a conservatively modified variant of SEQ ID NO: 26, or a variant of SEQ ID NO: 26 that comprises the canonical structure class of 1, the CDRH1 comprises the amino acid sequence of SEQ ID NO: 29, a variant of SEQ ID NO: 29, a conservatively modified variant of SEQ ID NO: 29, or a variant of SEQ ID NO: 29 that comprises the canonical structure class of 1; the CDRH2 comprises the amino acid sequence of SEQ ID NO: 35, a variant of SEQ ID NO: 35, a conservatively modified variant of SEQ ID NO: 35, and a variant of SEQ ID NO: 35 that comprises the canonical structure class of 1, the CDRH3 comprises the amino acid sequence of SEQ ID NO: 114, a variant of SEQ ID NO: 114, a conservatively modified variant of SEQ ID NO: 114, or a variant of SEQ ID NO: 114 that comprises the canonical structure class of 11. In particular embodiments when bound to canine PD-1, the antibody or antigen binding fragment thereof binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104.

In still other embodiments the CDRL1 comprises the amino acid sequence of SEQ ID NO: 14, a variant of SEQ ID NO: 14, a conservatively modified variant of SEQ ID NO: 14, or a variant of SEQ ID NO: 14 that comprises the canonical structure class of 4; the CDRL2 comprises the amino acid sequence of SEQ ID NO: 17, a variant of SEQ ID NO: 17, a conservatively modified variant of SEQ ID NO: 17, or a variant of SEQ ID NO: 17 that comprises the canonical structure class of 1; the CDRL3 comprises the amino acid sequence of SEQ ID NO: 23, a variant of SEQ ID NO: 23, a conservatively modified variant of SEQ ID NO: 23, or a variant of SEQ ID NO: 23 that comprises the canonical structure class of 1, the CDRH1 comprises the amino acid sequence of SEQ ID NO: 28, a variant of SEQ ID NO: 28, a conservatively modified variant of SEQ ID NO: 28, or a variant of SEQ ID NO: 28 that comprises the canonical structure class of 1; the CDRH2 comprises the amino acid sequence of SEQ ID NO: 32, a variant of SEQ ID NO: 32, a conservatively modified variant of SEQ ID NO: 32, and a variant of SEQ ID NO: 32 that comprises the canonical structure class of 2A, the CDRH3 comprises the amino acid sequence of SEQ ID NO: 37, a variant of SEQ ID NO: 37, a conservatively modified variant of SEQ ID NO: 37, or a variant of SEQ ID NO: 37 that comprises the canonical structure class of 13. In particular embodiments when bound to canine PD-1, the antibody or antigen binding fragment thereof binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, SEQ ID NO: 103, and/or SEQ ID NO: 104. In more particular embodiments when bound to canine PD-1, the antibody or antigen binding fragment thereof binds to at least one amino acid residue within SEQ ID NO: 83, SEQ ID NO: 84 and/or SEQ ID NO: 100. In more specific embodiments when bound to canine PD-1, the antibodies or antigen binding fragments thereof bind to one or more amino acid residues of the following arginine residues: $R_{62}$, $R_{69}$, $R_{72}$, and $R_{75}$ of SEQ ID NO: 2.

The present invention includes antibodies and antigen binding fragments thereof that bind canine Programmed Death Receptor 1 (canine PD-1) with specificity, that when they are bound to canine PD-1, the antibody binds to at least one amino acid residue within SEQ ID NO: 103. In particular embodiments of this type, the antibodies and antigen binding fragments thereof bind canine PD-1 and block the binding of canine PD-1 to canine Programmed Death Ligand 1 (PD-L1). In more particular embodiments the antibodies and antigen binding fragments thereof bind canine PD-1 and also block the binding of canine PD-1 to canine Programmed Death Ligand 2 (PD-L2), Accordingly, in particular embodiments when bound to canine PD-1, the antibody (including the antibodies with one or more variant CDR, e.g., a variant including a conservatively modified variant and/or a variant that comprises a defined canonical structure class) binds to at least one amino acid residue within one or more amino acid sequences of the following: SEQ ID NO: 83, SEQ ID NO: 84, SEQ ID NO: 99, SEQ ID NO: 100, of SEQ ID NO: 101, SEQ ID NO: 102, and/or SEQ ID NO: 104. In even more particular embodiments when bound to canine PD-1, the antibodies or antigen binding fragments thereof bind to one or more amino acid residues of the following arginine residues: $R_{62}$, $R_{69}$, $R_{72}$, $R_{75}$, and $R_{90}$ of SEQ ID NO: 2. In specific embodiments when bound to canine PD-1, the antibodies or antigen binding fragments thereof bind to at least one amino acid residue within SEQ ID NO: 104. In more specific embodiments when bound to canine PD-1, the antibodies or antigen binding fragments thereof bind to one or more amino acid residues of the following arginine residues: $R_{62}$, $R_{69}$, $R_{72}$, and $R_{75}$ of SEQ ID NO: 2. In even more specific embodiments when bound to canine PD-1, the antibodies or antigen binding fragments thereof bind to $R_{75}$ of SEQ ID NO: 2.

The present invention further provides mammalian antibodies or antigen binding fragments thereof that bind to canine PD-1 with a dissociation constant (Kd) that is lower (e.g., $1\times10^{-13}$ M, or lower) than $1\times10^{-12}$ M. In particular embodiments the mammalian antibodies or antigen binding fragments thereof bind to canine PD-1 with a dissociation constant of $1\times10^{-5}$ M to $1\times10^{-12}$ M. In more particular embodiments the mammalian antibodies or antigen binding fragments thereof bind to canine PD-1 with a dissociation constant of $1\times10^{-7}$ M to $1\times10^{-11}$ M. In still more particular embodiments the mammalian antibodies or antigen binding fragments thereof bind to canine PD-1 with a dissociation constant of $1\times10^{-8}$ M to $1\times10^{-11}$ M. In yet more particular embodiments the mammalian antibodies or antigen binding fragments thereof bind to canine PD-1 with a dissociation constant of $1\times10^{-8}$ M to $1\times10^{-10}$ M.

The present invention also provides mammalian antibodies or antigen binding fragments thereof that bind to canine PD-1 with an on rate ($k_{on}$) that is greater than $1\times10^7$ $M^{-1}s^{-1}$. In particular embodiments the mammalian antibodies or antigen binding fragments thereof bind to canine PD-1 with an on rate of $1\times10^2$ $M^{-1}s^{-1}$ to $1\times10^7$ $M^{-1}s^{-1}$. In more particular embodiments the mammalian antibodies or antigen binding fragments thereof bind to canine PD-1 with an on rate of $1\times10^3$ $M^{-1}s^{-1}$ to $1\times10^6 M^{-1}s^{-1}$. In still more particular embodiments the mammalian antibodies or antigen binding fragments thereof bind to canine PD-1 with an on rate of $1\times10^3$ $M^{-1}s^{-1}$ to $1\times10^5 M^{-1}s^{-1}$. In yet more particular embodiments the mammalian antibodies or antigen binding fragments thereof bind to canine PD-1 on rate of $1\times10^4$ $M^{-1}s^{-1}$ to $1\times10^5 M^{-1}s^{-1}$.

The present invention further provides mammalian antibodies or antigen binding fragments thereof that bind to canine PD-1 with an off rate ($k_{off}$) slower than $1\times10^{-7}$ $s^{-1}$. In particular embodiments the mammalian antibodies or antigen binding fragments thereof bind to canine PD-1 with an off rate of $1\times10^{-3}$ $s^{-1}$ to $1\times10^{-8}$ $s^{-1}$. In more particular embodiments the mammalian antibodies or antigen binding fragments thereof bind to canine PD-1 with an off rate of $1\times10^{-4}$ $s^{-1}$ to $1\times10^{-7}$ $s^{-1}$. In still more particular embodiments the mammalian antibodies or antigen binding fragments thereof bind to canine PD-1 with an off rate of $1\times10^{-5}$ $s^{-1}$ to $1\times10^{-7}$ $s^{-1}$.

In related embodiments, the mammalian antibodies or antigen binding fragments thereof stimulate antigen-specific memory responses to a tumor or pathogen. In particular embodiments, the mammalian antibodies or antigen binding fragments thereof stimulate an antibody response in vivo. In other particular embodiments, the mammalian antibodies or antigen binding fragments thereof stimulate an immune response in an animal subject. In more specific embodiments the animal subject is a canine. In a related embodiment, the animal subject is a feline.

Accordingly, any of the antibodies of the present invention can exhibit one, two, three, four, five, or all these properties, i.e., the aforesaid dissociation constants with canine PD-1, the aforesaid on rates for binding with canine PD-1, the aforesaid off rates for dissociating from the antibody-canine PD-1 binding complex, stimulating an antigen-specific memory responses to a tumor or pathogen, stimulating an antibody response in vivo, and/or stimulating an immune response in an animal subject As indicated above, the antibodies (and antigen binding fragments thereof) of the present invention, including the aforesaid antibodies (and antigen binding fragments thereof), can be monoclonal antibodies (and antigen binding fragments thereof), mammalian antibodies (and antigen binding fragments thereof), e.g., murine (mouse) antibodies (and antigen binding fragments thereof), caninized antibodies (and antigen binding fragments thereof) including caninized murine antibodies (and antigen binding fragments thereof), and in certain embodiments the antibodies (and antigen binding fragments thereof) are isolated.

The present invention further provides nucleic acids (including isolated nucleic acids) that encode any one of the light chains of the caninized antibody of the present invention. Similarly, the present invention provides isolated nucleic acids that encode any one of the heavy chains of the caninized antibody of the present invention. Examples of specific nucleotide sequences are provided herein.

The present invention further provides expression vectors that comprise one or more of the nucleic acids (including isolated nucleic acids) of the present invention. The present invention further provides host cells that comprise one or more expression vectors of the present invention.

In particular embodiments, the antibody is a recombinant antibody or an antigen binding fragment thereof. In related embodiments, the variable heavy chain domain and variable light chain domain are connected by a flexible linker to form a single-chain antibody.

In particular embodiments, the antibody or antigen binding fragment is a Fab fragment. In other embodiments, the antibody or antigen binding fragment is a Fab' fragment. In other embodiments, the antibody or antigen binding fragment is a (Fab')₂ fragment. In still other embodiments, the antibody or antigen binding fragment is a diabody. In particular embodiments, the antibody or antigen binding fragment is a domain antibody. In particular embodiments, the antibody or antigen binding fragment is a camelized single domain antibody.

In particular embodiments, a caninized murine anti-canine PD-1 antibody or antigen binding fragment increases the immune response of the canine subject being treated.

The present invention further provides isolated nucleic acids that encode caninized murine anti-canine PD-1 antibodies or portions thereof. In related embodiments such antibodies or antigen binding fragments can be used for the preparation of a medicament to treat cancer in a canine subject. Alternatively, or in conjunction, the present invention provides for the use of any of the antibodies or antibody fragments of the present invention for diagnostic use. In yet additional embodiments, a kit is provided comprising any of the caninized antibodies or antigen binding fragments disclosed herein.

In yet additional embodiments, an expression vector is provided comprising an isolated nucleic acid encoding any of the caninized murine anti-canine PD-1 antibodies or antigen binding fragments of the invention. The invention also relates to a host cell comprising any of the expression vectors described herein. In particular embodiments, these nucleic acids, expression vectors or polypeptides of the invention are useful in methods of making an antibody.

The present invention further provides antigenic peptides (including isolated antigenic peptides) that consist of 80 or fewer amino acid residues that comprise the amino acid sequence of SEQ ID NO: 103, and/or SEQ ID NO: 83, and/or SEQ ID NO: 84, and/or SEQ ID NO: 99, and/or SEQ ID NO: 100, and/or SEQ ID NO: 101, and/or SEQ ID NO: 102, and/or SEQ ID NO: 104. In related embodiments, the antigenic peptides (including isolated peptides) consist of 60 or fewer amino acid residues that comprise the amino acid sequence of SEQ ID NO: 103, and/or SEQ ID NO: 83, and/or SEQ ID NO: 84, and/or SEQ ID NO: 99, and/or SEQ ID NO: 100, and/or SEQ ID NO: 101, and/or SEQ ID NO: 102, and/or SEQ ID NO: 104. In other embodiments the antigenic peptides consist of 10 to 44 amino acid residues from the amino acid sequence of SEQ ID NO: 103. In still other embodiments the antigenic peptides consist of 15 to 45 amino acid residues from the amino acid sequence of SEQ ID NO: 103.

The present invention further provides antigenic peptides (including isolated peptides) that consist of 80 or fewer amino acid residues that comprise an amino acid sequence that is 80%, 85%, 90%, 95% or 100% identical with SEQ ID NO: 103, and/or SEQ ID NO: 83, and/or SEQ ID NO: 84, and/or SEQ ID NO: 99, and/or SEQ ID NO: 100, and/or SEQ ID NO: 101, and/or SEQ ID NO: 102, and/or SEQ ID NO: 104 and binds to an isolated mammalian antibody or antigen binding fragment thereof of the present invention. In related embodiments, the antigenic peptides (including isolated antigenic peptides) consist of 60 or fewer amino acid residues that comprise an amino acid sequence that is 80%, 85%, 90%, 95% or 100% identical with SEQ ID NO: 103 and/or SEQ ID NO: 83, and/or SEQ ID NO: 84, and/or SEQ ID NO: 9, and/or SEQ ID NO: 100, and/or SEQ ID NO: 101, and/or SEQ ID NO: 102, and/or SEQ ID NO: 104 and binds to an isolated mammalian antibody or antigen binding fragment thereof. In other embodiments the peptides consist of 10 to 44 amino acid residues from an amino acid sequence that is 80%, 85%, 90%, 95% or 100% identical with SEQ ID NO: 103 and/or SEQ ID NO: 83, and/or SEQ ID NO: 84, and/or SEQ ID NO: 99, and/or SEQ ID NO: 100, and/or SEQ ID NO: 101, and/or SEQ ID NO: 102, and/or SEQ ID NO: 104 and binds to an isolated mammalian antibody or antigen binding fragment thereof. In particular embodiments the antibody is 1B5. In other embodiments the antibody is 3B6. In other particular embodiments the antibody is 2H9. In still other embodiments, the antibody is 2G9. In yet other embodiments the antibody is 1A1. In still other embodiments, the antibody is 1E4.

The present invention further provides fusion proteins that comprise any of the aforesaid antigenic peptides. In a particular embodiment, the fusion protein comprises such an antigenic peptide and an Fc region of a non-canine mammalian IgG antibody. In a more particular embodiment the fusion protein comprises an Fc region of a non-canine mammalian IgG antibody. In certain embodiments the non-canine mammalian IgG antibody is a murine IgG. In alternative embodiments the non-canine mammalian IgG antibody is a human IgG. In other embodiments the non-canine mammalian IgG antibody is an equine IgG. In still other embodiments the non-canine mammalian IgG antibody is a porcine IgG. In yet other embodiments the non-canine mammalian IgG antibody is a bovine IgG.

In particular embodiments the non-canine mammalian IgG antibody is an IgG1. In other embodiments the non-canine mammalian IgG antibody is an IgG2a. In still other embodiments the non-canine mammalian IgG antibody is an IgG3. In yet other embodiments the non-canine mammalian IgG antibody is an IgG4.

In other embodiments the fusion protein comprises any of the aforesaid antigenic peptides and maltose-binding protein. In yet other embodiments, the fusion protein comprises any of the aforesaid antigenic peptides and beta-galactosidase. In still other embodiments the fusion protein comprises any of the aforesaid antigenic peptides and glutathione S-transferase. In yet other embodiments, the fusion protein comprises any of the aforesaid antigenic peptides and thioredoxin. In still other embodiments the fusion protein comprises any of the aforesaid antigenic peptides and Gro EL. In yet other embodiments the fusion protein comprises any of the aforesaid antigenic peptides and NusA.

The present invention further provides nucleic acids (including isolated nucleic acids) that encode the antigenic peptides and the corresponding fusion proteins of the present invention. The present invention also provides expression vectors that comprise these nucleic acids.

In addition, the present invention includes pharmaceutical compositions comprising anti-canine PD-1 antibodies or antigen binding fragments thereof of the present invention, antigenic peptides (including isolated antigenic peptides) from canine PD-1, fusion proteins comprising the antigenic peptides from canine PD-1 of the present invention, nucleic acids (including isolated nucleic acids) encoding the antigenic fragments and/or fusion proteins of the present invention, the expression vectors comprising such nucleic acids, or any combination thereof, and a pharmaceutically acceptable carrier or diluent.

In addition, the present invention provides methods of increasing the activity of an immune cell, comprising administering to a subject in need thereof a therapeutically effective amount of such pharmaceutical compositions. In certain embodiments the method is used for the treatment of cancer. In other embodiments, the method is used in the treatment of an infection or infectious disease. In still other embodiments, a caninized antibody of the present invention or antigen binding fragment thereof is used as a vaccine adjuvant.

These and other aspects of the present invention will be better appreciated by reference to the following Brief Description of the Drawings and the Detailed Description.

BRIEF DESCRIPTION OF THE DRAWINGS

FIGS. 8A-8B provide the alignment of canine IgGB constant heavy chains (CHs) lacking ADCC function. The canine wild type IgB [cIgGB wt], Canine IgGB(+)A-hinge [cIgGB(+) A-hinge], Canine IgGB(+) D-hinge [cIgGB(+) D-hinge], and Canine IgGB (–) ADCC [cIgGB(–) ADCC] are depicted. The (+) A-hinge is the replacement with IgG-A hingep/us an aspartic acid and asparagine amino acid replacement as shown; the (+) D-hinge is the replacement with IgG-D hinge plus the aspartic acid and the asparagine amino acid replacement as shown. The (–)ADCC is the aspartic acid and asparagine amino acid replacement.

DETAILED DESCRIPTION

Abbreviations

Figure 1:
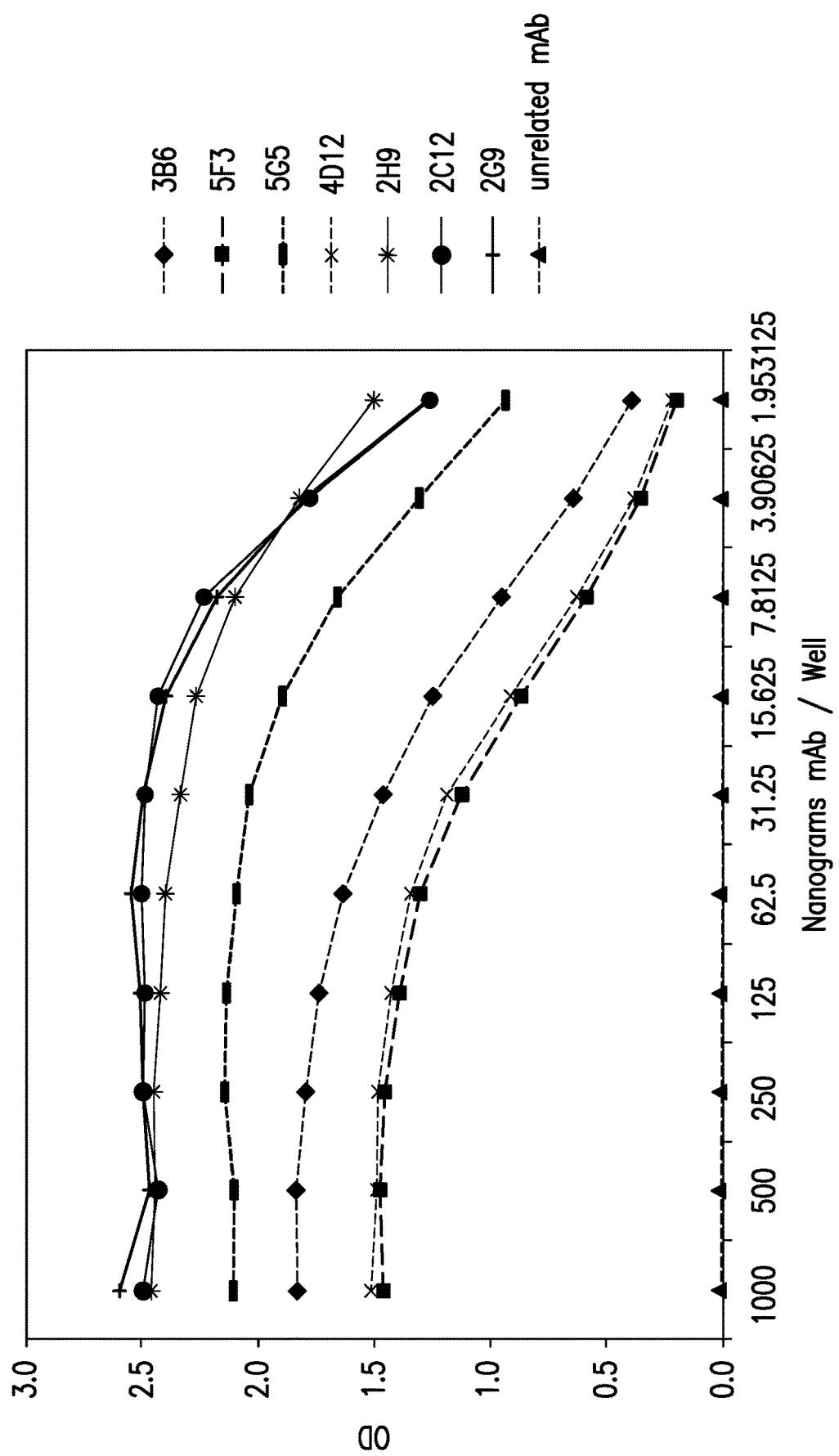
FIG. 1 shows the reactivity of mouse mAbs against extracellular domain of canine PD-1. Various mouse mAbs were tested for their binding to extracellular domain of canine PD-1 by ELISA. Tested mAbs are designated as ♦ 3B6, ■ 5F3, – 5G5, X 4D12, ✱ 2H9, • 2C12, + 2G9, ▲ unrelated mAb.
Figure 2:
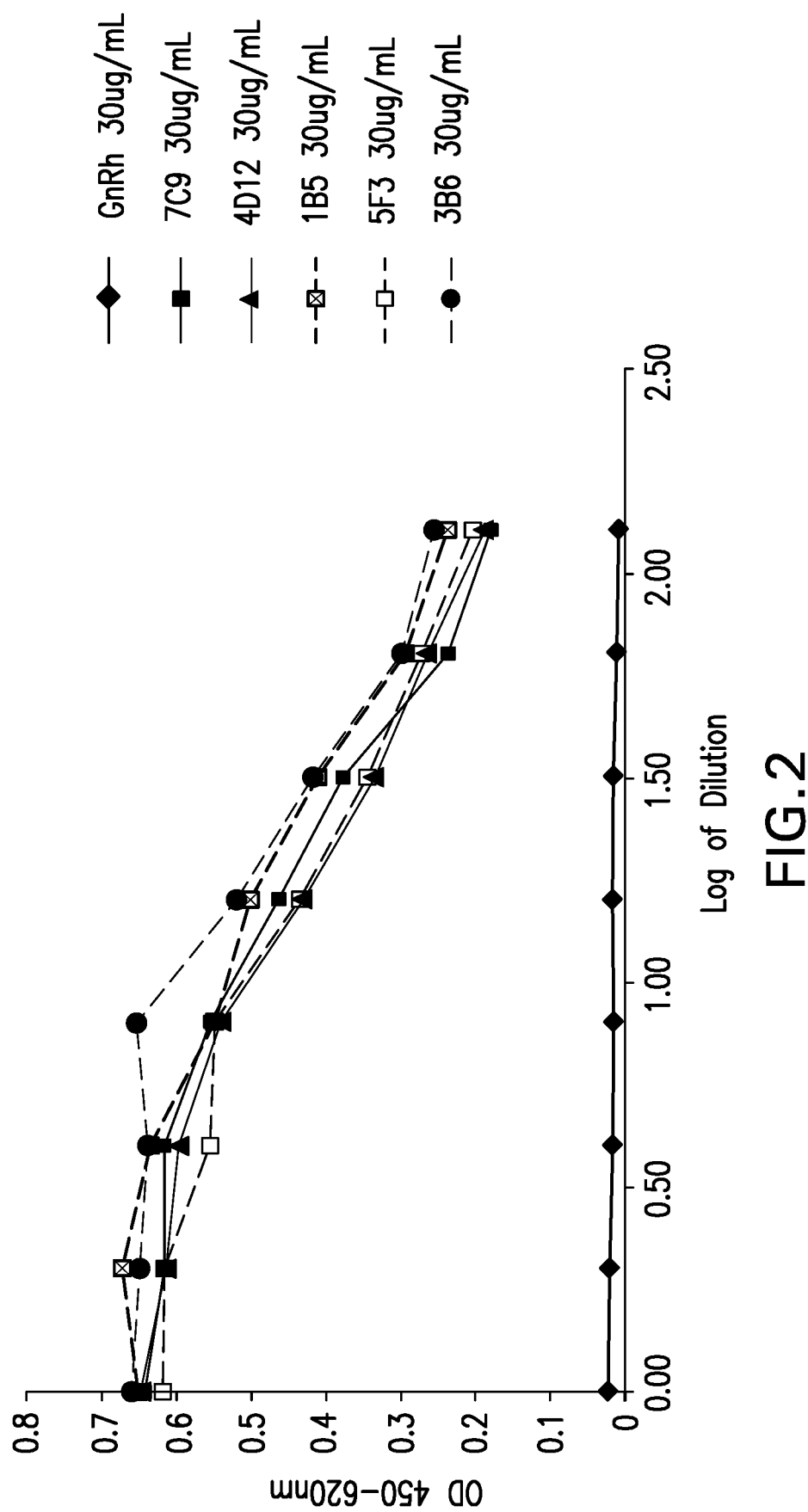
FIG. 2 shows the reactivity of mouse mAbs against cell surface-expressed canine PD-1. Various mouse mAbs were tested for their binding to canine PD-1 expressed on CHO cells by CELISA. Antibodies are designated as: ━◆━ Gn8h 30 ug/mL; ━▒━ 7C9 30 ug/mL; ━▲━ 4D12 30 ug/mL; ━■━ I85 30 ug/mL; ━▒━ 5 F2 30 ug/mL and ━●━ 386 30 ug/mL.
Figure 3A:
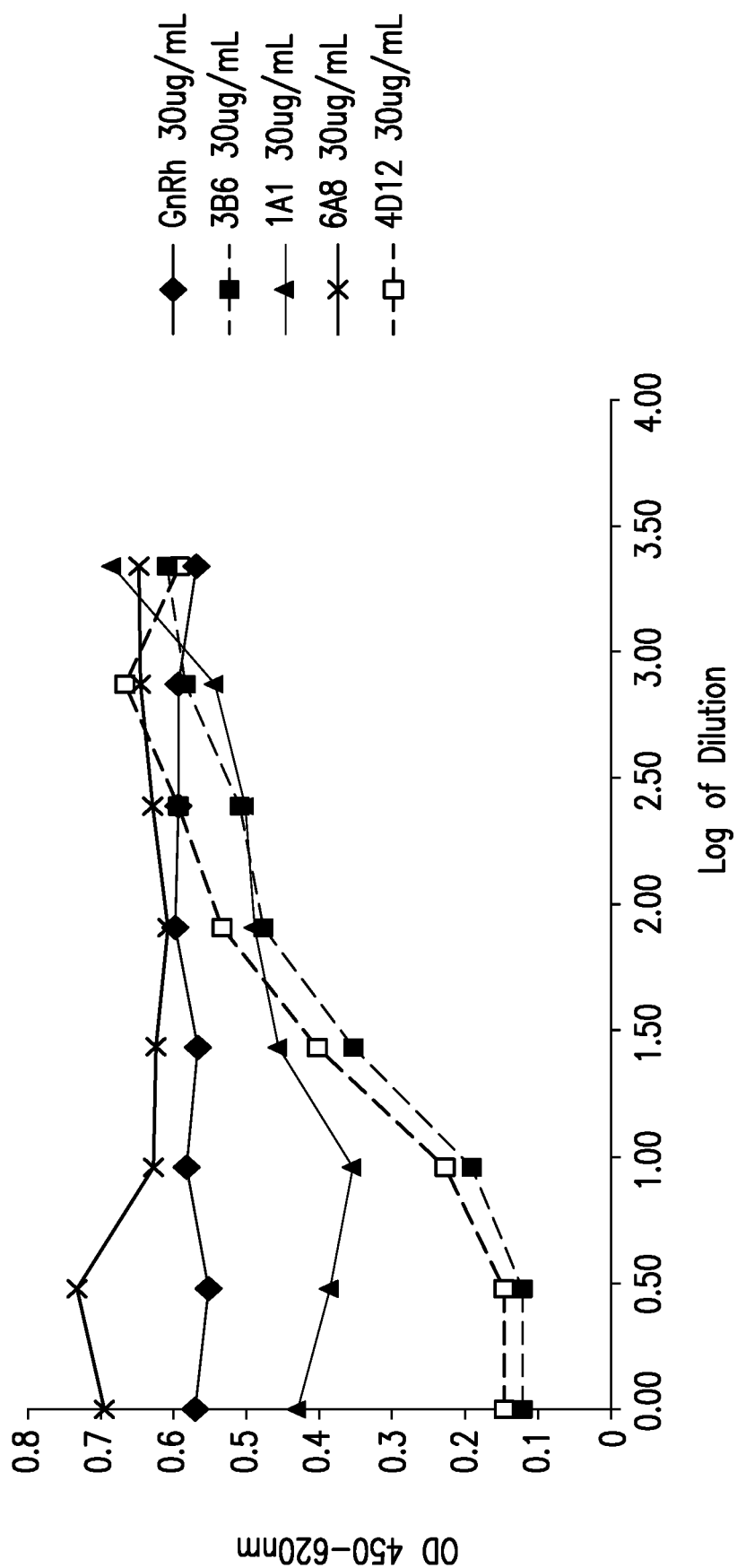
FIG. 3A shows ligand blockade with mouse mAbs against canine PD-1. Various mouse mAbs were tested for their ability to inhibit binding of PD-1 expressed on CHO cells to PD-L1. Antibodies are designated as: ━◆━ GnRh 30 ug/mL; ━■━ 386 30 ug/mL; ━▲━ 1 A1 30 ug/mL; ━✕━ 6A8 30 ug/mL and ━▒━ 4D12 30 ug/mL.
Figure 3B:
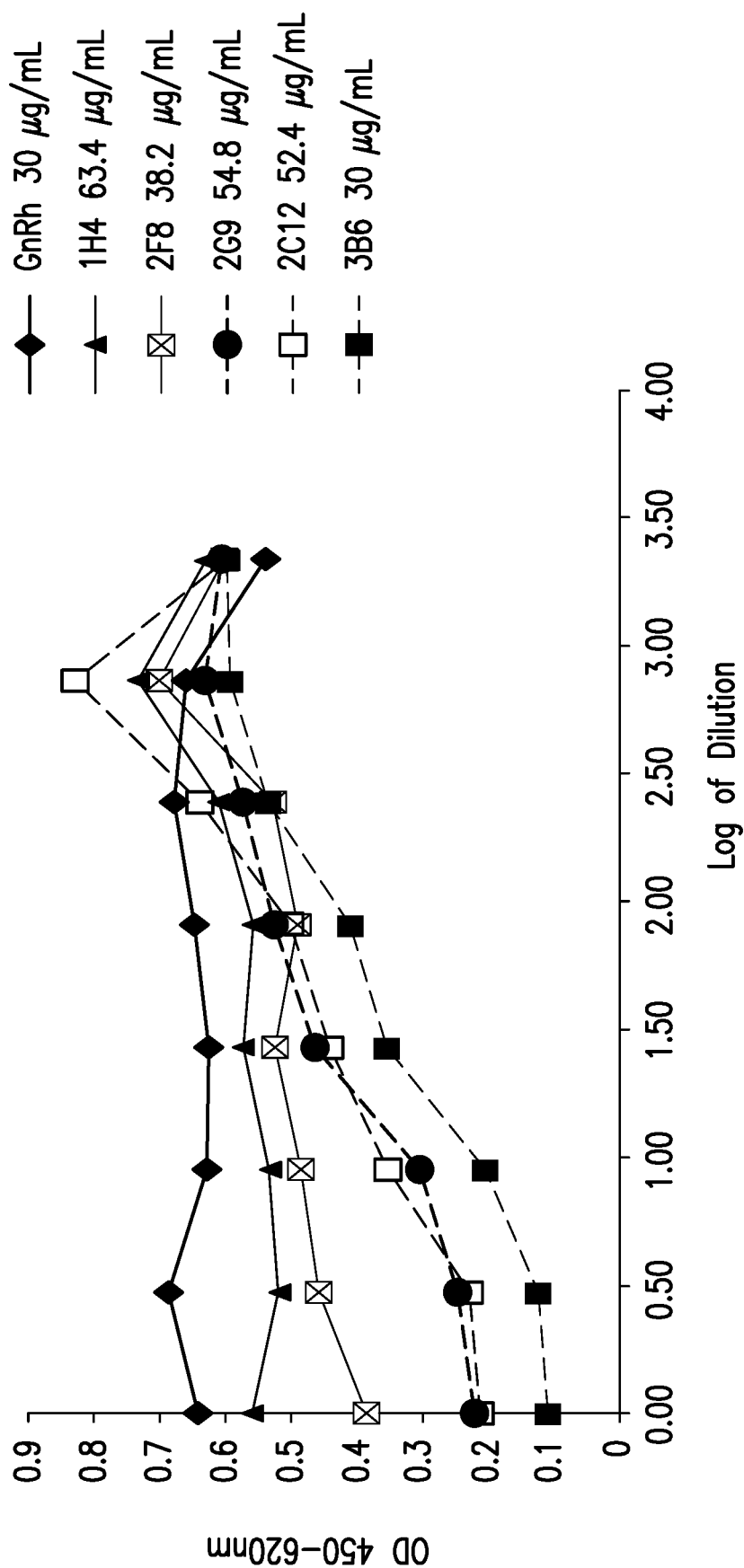
FIG. 3B shows ligand blockade with mouse mAbs against canine PD-1. Various mouse mAbs were tested for their ability to inhibit binding of PD-1 expressed on CHO cells to PD-L1. Antibodies are designated as: ━◆━ GnRh 30 ug/mL; ━■━ 386 30 ug/mL; ━▲━ 1H63.4 ug/mL; ━▒━ 2C12 52.4 ug/mL; ━■━ 2F8 38.2 ug/mL and ━●━ 2G9 54.8 ug/mL.
Figure 3C:
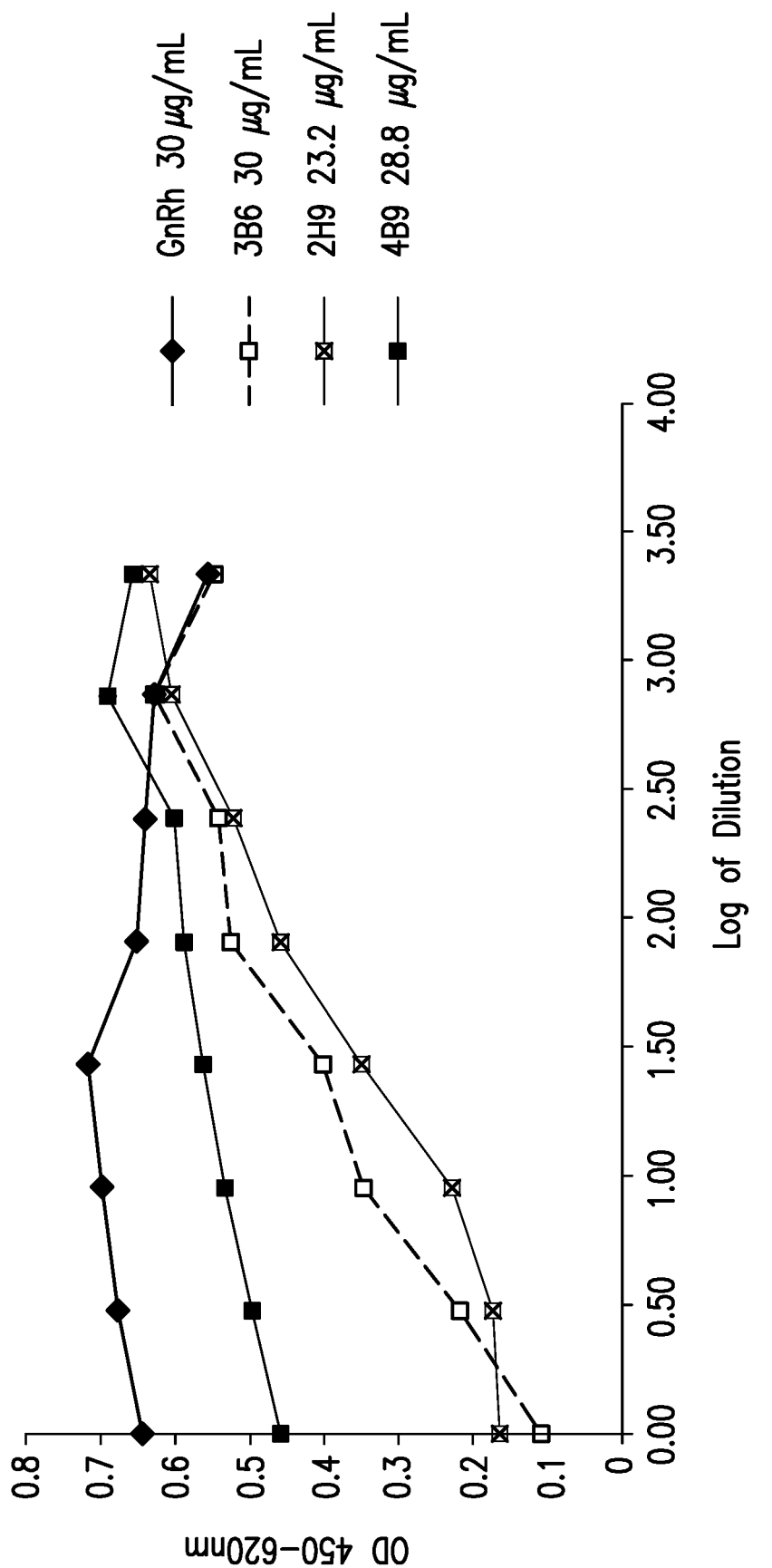
FIG. 3C shows ligand blockade with mouse mAbs against canine PD-1. Various mouse mAbs were tested for their ability to inhibit binding of PD-1 expressed on CHO cells to PD-L1. Antibodies are designated as: ━◆━ GnRh 30 ug/mL; ━▒━ 3B6 30 ug/mL; ━✕━ 2H9 23.2 ug/mL and ━■━ 4B9 28.8 ug/mL.
Figure 4:
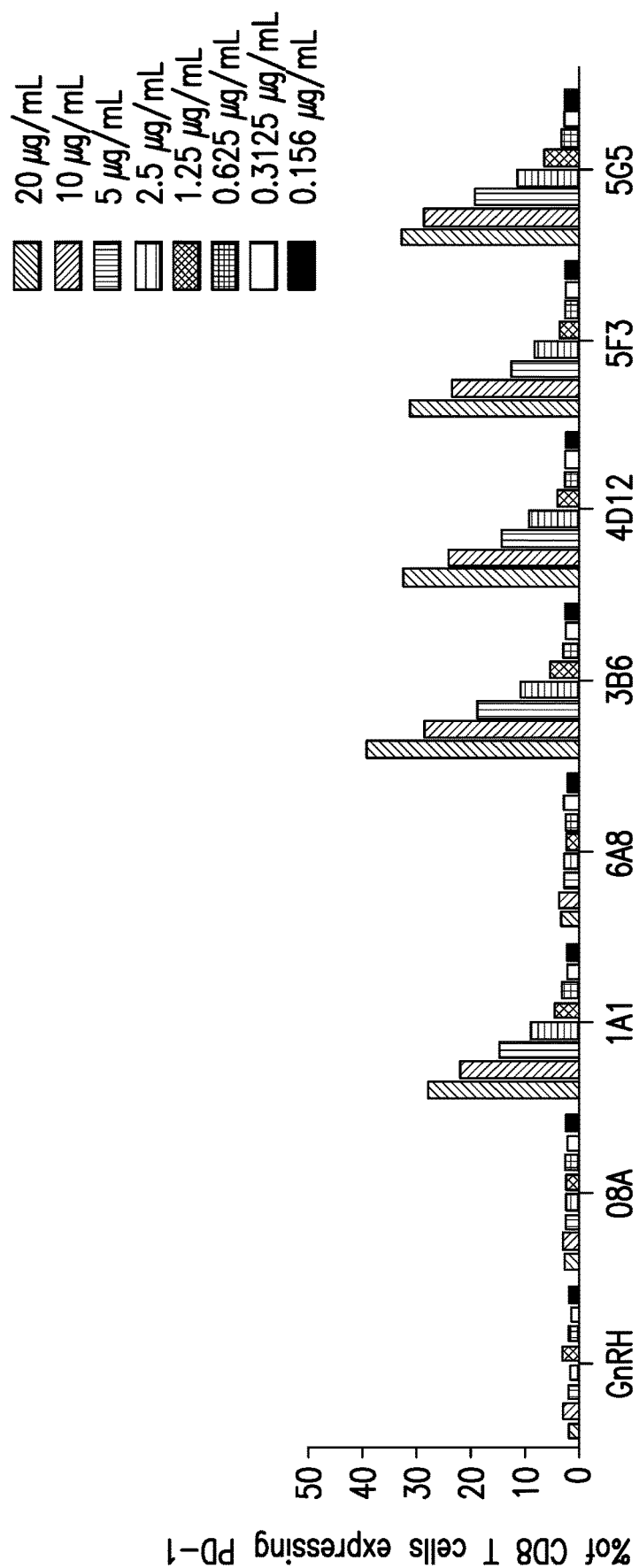
FIG. 4 shows the binding of mouse mAbs to canine PD-1 on CD+ T cells in PBMC from healthy dogs. Various mouse mAbs were tested for their ability to bind to canine PD-1 expressed on CD+ T cells from PBMC from healthy dogs. Antibodies were tested at 2 fold dilutions covering starting with 0.156-20 µg/ml range.
Figure 5:
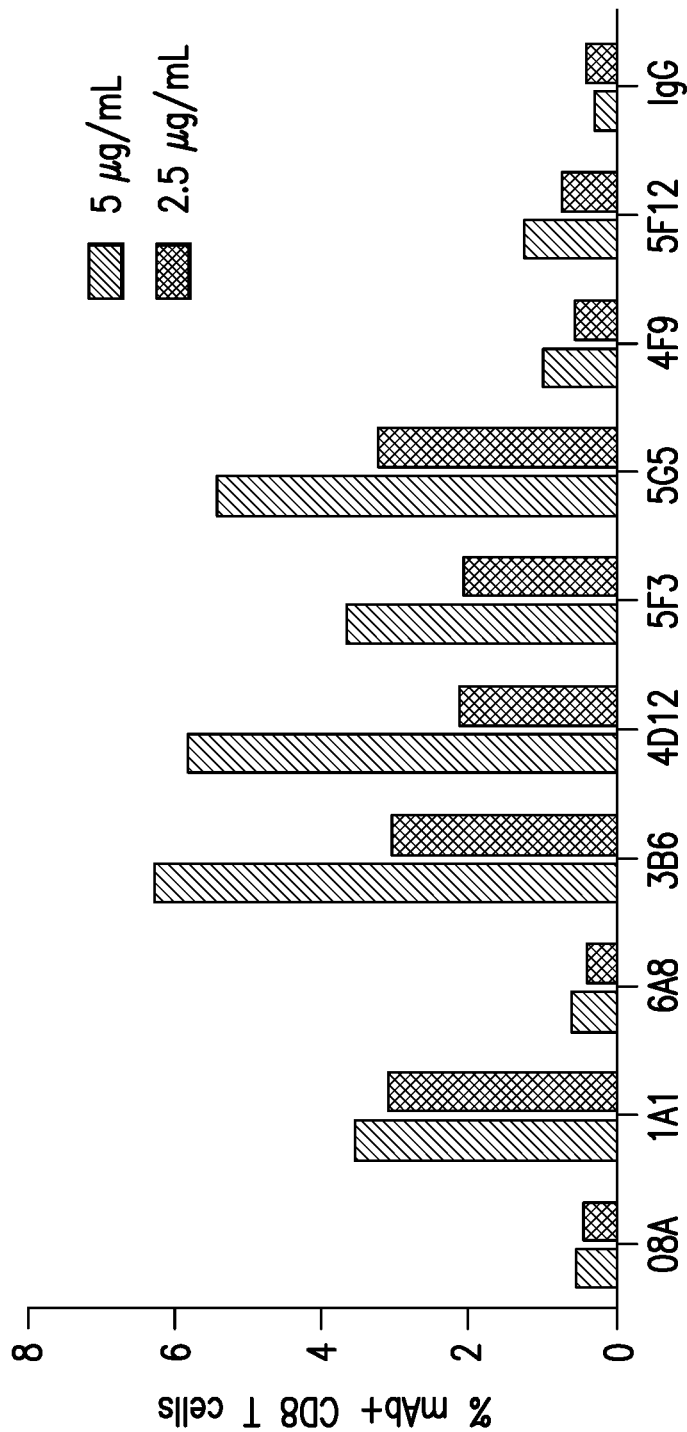
FIG. 5 shows the binding of mouse mAbs to canine PD-1 on CD8+ T cells in PBMC from dogs with cancer. Indicated mouse mAbs were tested for their ability to bind to canine PD-1 expressed on CD8+ T cells from dogs with cancer (sarcoma). Antibodies were tested at 2.5 and 5 µg/ml.
Figure 6:
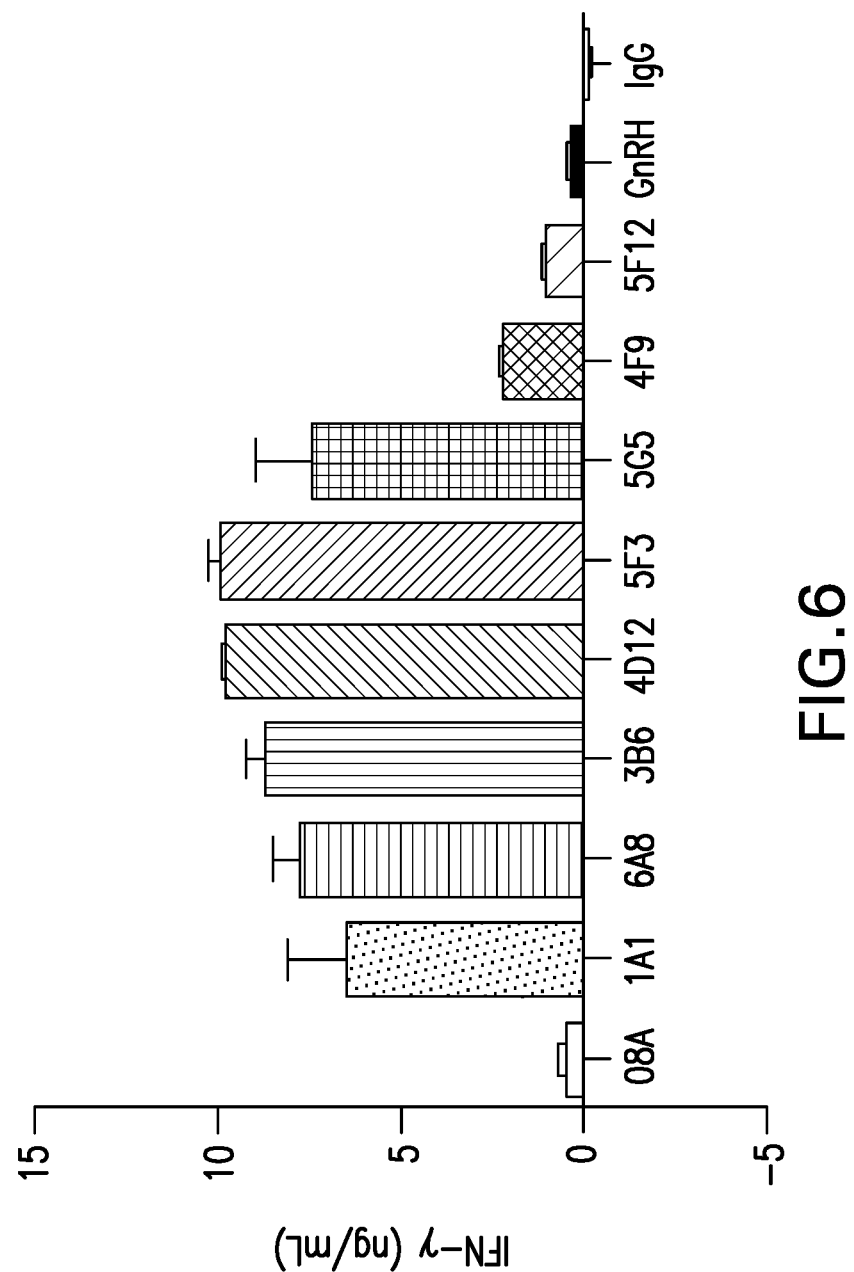
FIG. 6 shows the cytokine secretion induced by mouse mAbs to canine PD-1. Various mouse mAbs were tested for their ability to induce cytokine secretion from PBMC from healthy dogs.
Figure 7:
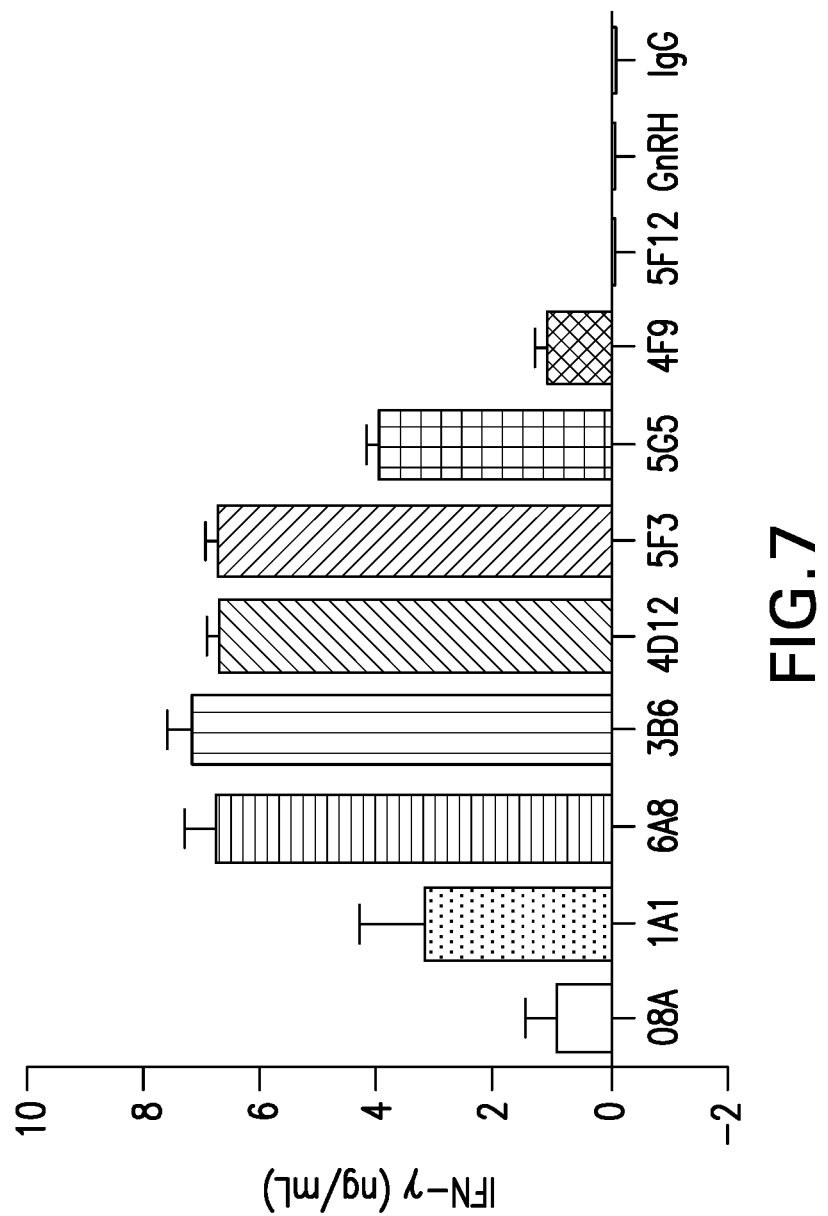
FIG. 7 shows the cytokine secretion induced by mouse mAbs to canine PD-1. Various mouse mAbs were tested for their ability to induce cytokine secretion from PBMC from dogs with cancer (hemangiosarcoma).

Throughout the detailed description and examples of the invention the following abbreviations will be used:
ADCC Antibody-dependent cellular cytotoxicity
CDC Complement-dependent cyotoxicity
CDR Complementarity determining region in the immunoglobulin variable regions, defined using the Kabat numbering system
CHO Chinese hamster ovary
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat [*Sequences of Proteins of Immunological Interest,* 5th Ed. Public Health Service, National Institutes of Health, Bethesda, Md. (1991)]
mAb Monoclonal antibody (also Mab or MAb)
MES 2-(N-morpholino)ethanesulfonic acid
MOA Mechanism of action
NHS Normal human serum
PCR Polymerase chain reaction
PK Pharmacokinetics
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, e.g., a canine experimental subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., canine, feline, or human) and most preferably a canine.

As used herein, a "substitution of an amino acid residue" with another amino acid residue in an amino acid sequence of an antibody for example, is equivalent to "replacing an amino acid residue" with another amino acid residue and denotes that a particular amino acid residue at a specific position in the amino acid sequence has been replaced by (or substituted for) by a different amino acid residue. Such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies.

"Treat" or "treating" means to administer a therapeutic agent, such as a composition containing any of the antibodies or antigen binding fragments of the present invention, internally or externally to a canine subject or patient having one or more disease symptoms, or being suspected of having a disease, for which the agent has therapeutic activity.

Typically, the agent is administered in an amount effective to alleviate and/or ameliorate one or more disease symptoms in the treated subject or population, whether by inducing the regression of or inhibiting the progression of such symptom (s) by any clinically measurable degree. The amount of a therapeutic agent that is effective to alleviate any particular disease symptom (also referred to as the "therapeutically effective amount") may vary according to factors such as the disease state, age, and weight of the patient (e.g., canine), and the ability of the pharmaceutical composition to elicit a desired response in the subject. Whether a disease symptom has been alleviated or ameliorated can be assessed by any clinical measurement typically used by veteranarians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary (e.g., canine) or research subject, refers to therapeutic treatment, as well as research and diagnostic applications. "Treatment" as it applies to a human, veterinary (e.g., canine), or research subject, or cell, tissue, or organ, encompasses contact of the antibodies or antigen binding fragments of the present invention to a canine or other animal subject, a cell, tissue, physiological compartment, or physiological fluid.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats, and wild or feral cats.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a mouse antibody) in both chains. Optionally the heavy and/or light chains of the canine antibody may contain some foreign non-CDR residues, e.g., so as to preserve the conformation of the foreign CDRs within the canine antibody, and/or to modify the Fc function, as exemplified below.

Canine PD-1 has been found to comprise the amino acid sequence of SEQ ID NO: 2. In a specific embodiment canine PD-1 is encoded by a nucleic acid that comprises the nucleotide sequence of SEQ ID NO: 1. Canine PD-1 sequences may differ by having, for example, conserved variations in non-conserved regions, but the canine PD-1 will have substantially the same biological function as the canine PD-1 comprising the amino acid sequence of SEQ ID NO: 2. For example, a biological function of PD-1 is to attenuate T-cell responses when bound to PD-L1 and/or PD-L2. That is, PD-1 may be considered a negative regulator. Notably, the cytoplasmic tail of PD-1 contains two tyrosine-based signaling motifs, an ITIM (immunoreceptor tyrosine-based inhibition motif) and an ITSM (immunoreceptor tyrosine-based switch motif). In addition, a biological function of canine PD-1 may be having, for example, an epitope in the extracellular domain that is specifically bound by an antibody of the instant disclosure.

Canine PD-L1 has been found to comprise the amino acid sequence of SEQ ID NO: 8. In a specific embodiment canine PD-L1 is encoded by a nucleotide sequence comprising SEQ ID NO: 7. Canine PD-L1 sequences may differ by having, for example, conserved variations in non-conserved regions, but the canine PD-L1 will have substantially the same biological function as the canine PD-L1 comprising the amino acid sequence of SEQ ID NO: 8. For example, one biological function of PD-L1 is to attenuate T-cell responses when bound to PD-1.

A particular canine PD-1 or PD-L1 amino acid sequence respectively, will generally be at least 90% identical to the canine PD-1 comprising the amino acid sequence of SEQ ID NO: 2, or canine PD-L1 comprising the amino acid sequence of SEQ ID NO: 8, respectively. In certain cases, a canine PD-1 or PD-L1 respectively, may be at least 95%, or even at least 96%, 97%, 98% or 99% identical to the canine PD-1 comprising the amino acid sequence of SEQ ID NO: 2, or the canine PD-L1 comprising the amino acid sequence of SEQ ID NO: 8, respectively. In certain embodiments, a canine PD-1 or a PD-L1 amino acid sequence respectively, will display no more than 10 amino acid differences from the canine PD-1 comprising the amino acid sequence of SEQ ID NO: 2, or the canine PD-L1 comprising the amino acid sequence of SEQ ID NO: 8, respectively. In certain embodiments, the canine PD-1 or the PD-L1 amino acid sequence respectively, may display no more than 5, or even no more than 4, 3, 2, or 1 amino acid difference from the canine PD-1 comprising the amino acid sequence of SEQ ID NO: 2, or the canine PD-L1 comprising the amino acid sequence of SEQ ID NO: 8, respectively. Percent identity can be determined as described herein below.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the mammalian body (e.g., canine body) of cancerous cells, cells or tissues infected with pathogens, or invading pathogens.

Anti-Canine PD-1 Antibodies

The present invention provides isolated antibodies (particularly murine anti-canine PD-1 antibodies and caninized antibodies thereof) or antigen binding fragments thereof that bind canine PD-1 and uses of such antibodies or fragments thereof. In specific embodiments murine anti-canine PD-1 CDRs from murine anti-canine PD-1 antibodies are provided that have been shown to both bind canine PD-1 and to block the binding of canine PD-1 to its ligand, canine PD-L1. These CDRs can be inserted into a modified canine frame of a canine antibody to generate a caninized murine anti-canine PD-1 antibody.

As used herein, an "anti-canine PD-1 antibody" refers to an antibody that was raised against canine PD-1 (e.g., in a mammal such as a mouse or rabbit) and that specifically binds to canine PD-1. An antibody that "specifically binds to canine PD-1," and in particular canine PD-1, or an antibody that "specifically binds to a polypeptide comprising the amino acid sequence of canine PD-1", is an antibody that exhibits preferential binding to canine PD-1 as compared to other antigens, but this specificity does not require absolute binding specificity. An anti-canine PD-1 antibody is considered "specific" for canine PD-1 if its binding is determinative of the presence of canine PD-1 in a sample, or if it is capable of altering the activity of canine PD-1 without unduly interfering with the activity of other molecules in a canine sample, e.g. without producing undesired results such as false positives in a diagnostic context or side effects in a therapeutic context. The degree of specificity necessary for an anti-canine PD-1 antibody may depend on the intended use of the antibody, and at any rate is defined by its suitability for use for an intended purpose. The antibody, or binding compound derived from the antigen-binding site of an antibody, of the contemplated method binds to its antigen, or a variant or mutein thereof, with an affinity that is at least two-fold greater, preferably at least ten-times greater, more preferably at least 20-times greater, and most preferably at least 100-times greater than the affinity with any other antigen.

As used herein, an antibody is said to bind specifically to a polypeptide comprising a given antigen sequence (in this case a portion of the amino acid sequence of canine PD-1) if it binds to polypeptides comprising the portion of the amino acid sequence of canine PD-1, but does not bind to other canine proteins lacking that portion of the sequence of canine PD-1. For example, an antibody that specifically binds to a polypeptide comprising canine PD-1 may bind to a FLAG®-tagged form of canine PD-1, but will not bind to other FLAG®-tagged canine proteins. An antibody, or binding compound derived from the antigen-binding site of an antibody, binds to its canine antigen, or a variant or mutein thereof, "with specificity" when it has an affinity for that canine antigen or a variant or mutein thereof which is at least ten-times greater, more preferably at least 20-times greater, and even more preferably at least 100-times greater than its affinity for any other canine antigen tested.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), canonized antibodies, fully canine antibodies, chimeric antibodies and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antigen binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

A "fragment crystallizable" ("Fc") region contains two heavy chain fragments comprising the CH3 and CH2 domains of an antibody. The two heavy chain fragments are held together by two or more disulfide bonds and by hydrophobic interactions of the CH3 domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. [See, Pluckthun, THE PHARMACOLOGY OF MONOCLONAL ANTIBODIES, vol. 113 Rosenburg and Moore eds., Springer-Verlag, New York, pp. 269-315 (1994); WO 88/01649; and U.S. Pat. Nos. 4,946,778 and 5,260,203.]

As used herein, the term "canonical structure" refers to the local conformation that can be adopted by each of the hypervariable regions of the heavy and light chain of an antibody within the framework that they reside. For each hypervariable region, there are a small number of canonical structures (generally denoted by simple integers such as 1 or 2 etc.), which can be predicted with great accuracy from the amino acid sequences of the corresponding hypervariable region (particularly within the context of the amino acid sequence of its framework, as provided below for the corresponding anti-canine PD-1 variable domains). These canonical structures can be determinative regarding whether a modification of the amino acid sequence of a given CDR will result in the retention or loss of the ability to bind to its antigen binding partner [See, Chothia and Lesk, *Canonical Structures for the hypervariable regions of immunoglobulins, J. Mol. Biol.* 196:901-917(1987); Chothia et al., *Conformation of immunoglobulin hypervaribale regions, Nature,* 34:877-883(1989); and Al-Lazikani et al., *Standard Conformations for the canonical structures of immunoglobulins, J. Mol. Biol.* 273:927-948 (1997)].

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. [See, e.g., Muyldermans et al., *Trends Biochem. Sci.* 26:230 (2001); Reichmann et al., *J. Immunol. Methods* 231:25 (1999); WO 94/04678; WO 94/25591; U.S. Pat. No. 6,005,079]. In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. [See, EP 0 404 097 B1; WO 93/11161; and Holliger et al., *Proc. Natl. Acad. Sci. USA* 90: 6444-6448 (1993)]. For a review of engineered antibody variants [generally see Holliger and Hudson *Nat. Biotechnol.* 23:1126-1136 (2005)].

Typically, an antibody or antigen binding fragment of the invention retains at least 10% of its canine PD-1 binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine PD-1 binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, a "chimeric antibody" is an antibody having the variable domain from a first antibody and the constant domain from a second antibody, where the first and second antibodies are from different species. [U.S. Pat. No. 4,816,567; and Morrison et al., *Proc. Natl. Acad. Sci. USA* 81: 6851-6855 (1984)]. Typically the variable domains are obtained from an antibody from an experimental animal (the "parental antibody"), such as a rodent, and the constant domain sequences are obtained from the animal subject antibodies, e.g., human or canine so that the resulting chimeric antibody will be less likely to elicit an adverse immune response in a canine or human subject respectively, than the parental (e.g., rodent) antibody.

As used herein, the term "caninized antibody" refers to forms of antibodies that contain sequences from both canine and non-canine (e.g., murine) antibodies. In general, the caninized antibody will comprise substantially all of at least one or more typically, two variable domains in which all or substantially all of the hypervariable loops correspond to those of a non-canine immunoglobulin (e.g., comprising 6 murine anti-canine PD-1 CDRs as exemplified below), and all or substantially all of the framework (FR) regions (and typically all or substantially all of the remaining frame) are those of a canine immunoglobulin sequence. As exemplified herein, a caninized antibody comprises both the three heavy chain CDRs and the three light chain CDRS from a murine anti-canine PD-1 antibody together with a canine frame or a modified canine frame. A modified canine frame comprises one or more amino acids changes as exemplified herein that further optimize the effectiveness of the caninized antibody, e.g., to increase its binding to canine PD-1 and/or its ability to block the binding of canine PD-1 to canine PD-L1.

The term "fully canine antibody" refers to an antibody that comprises canine immunoglobulin protein sequences only. A fully canine antibody may contain murine carbohydrate chains if produced in a mouse, in a mouse cell, or in a hybridoma derived from a mouse cell. Similarly, "mouse antibody" refers to an antibody that comprises mouse immunoglobulin sequences only.

Alternatively, a fully canine antibody may contain rat carbohydrate chains if produced in a rat, in a rat cell, or in a hybridoma derived from a rat cell. Similarly, "rat antibody" refers to an antibody that comprises rat immunoglobulin sequences only.

There are four known IgG heavy chain subtypes of dog IgG and they are referred to as IgG-A, IgG-B, IgG-C, and IgG-D. The two known light chain subtypes are referred to as lambda and kappa.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). [See Kabat et al. *Sequences of Proteins of Immunological Interest*, 5th Ed. Public Health Service, National Institutes of Health, Bethesda, Md. (1991), definining the CDR regions of an antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

Besides binding and activating of canine immune cells, a canine or caninized antibody against PD-1 optimally has two attributes:
1. Lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has high level of ADCC activity. On the other hand, IgG-A binds weakly to protein A, but displays undesirable ADCC activity. Moreover, neither IgG-C nor IgG-D can be purified on protein A columns, although IgG-D display no ADCC activity. (IgG-C has considerable ADCC activity). The present invention overcomes this difficulty by providing mutant canine IgG-B antibodies specific to PD-1; such antibodies lack effector functions such as ADCC and can be easily of purified using industry standard protein A chromatography.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. [*Nucleic Acids Res.* 33:D256-D261 (2005)].

Properties of Murine Anti-Canine PD-1 and Caninized Murine Anti-Canine PD-1 Antibodies The present invention provides isolated murine anti-canine PD-1 antibodies and caninized antibodies thereof, methods of use of the antibodies or antigen binding fragments thereof in the treatment of disease e.g., the treatment of cancer in canines. In canine, there are four IgG heavy chains referred to as A, B, C, and D. These heavy chains represent four different subclasses of dog IgG, which are referred to as IgGA, IgGB, IgGC and IgGD. The DNA and amino acid sequences of these four heavy chains were first identified by Tang et al. [*Vet. Immunol. Immunopathol.* 80: 259-270 (2001)]. The amino acid and DNA sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from Gen-Bank Databases. For example the kappa light chain amino acid sequence has accession number ABY 57289.1 and the lambda light chain has accession number ABY 55569.1. In the present invention, the amino acid sequence for each of the four canine IgG Fc fragments is based on the identified boundary of CH1 and CH2 domains as determined by Tang et al, supra. Caninized murine anti-canine PD-1 antibodies that bind canine PD-1 include, but are not limited to: antibodies that comprise canine IgG-A, IgG-B, and IgG-D heavy chains and/or canine kappa light chains together with murine anti-canine PD-1 CDRs. Accordingly, the present invention provides isolated murine anti-canine PD-1 and/or caninized murine anti-canine PD-1 antibodies or antigen binding fragments thereof that bind to canine PD-1 and block the binding of canine PD-1 to canine PD-L1.

The present invention further provides full length canine heavy chains that can be matched with corresponding light chains to make a caninized antibody. Accordingly, the present invention further provides caninized murine anti-canine antigen antibodies (including isolated caninized murine anti-canine PD-1 antibodies) and methods of use of the antibodies or antigen binding fragments thereof in the treatment of disease e.g., the treatment of cancer in canines.

The isolated antibody or antigen binding fragment thereof that binds canine PD-1 can comprise one, two, three, four, five, or six of the complementarity determining regions (CDRs) of the murine anti-canine antibody as described herein. The one, two, three, four, five, or six CDRs may be independently selected from the CDR sequences of those provided below. In a further embodiment, the isolated antibody or antigen-binding fragment thereof that binds canine PD-1 comprises a canine antibody kappa light chain comprising a murine light chain CDR-1, CDR-2 and/or CDR-3 and a canine antibody heavy chain IgG comprising a murine heavy chain CDR-1, CDR-2 and/or CDR-3.

In other embodiments, the invention provides antibodies or antigen binding fragments thereof that specifically binds PD-1 and have canine antibody kappa light chains comprising one to six different CDRs comprising at least 80%, 85%, 90%, 95%, 98% or 99% sequence identity with the amino acid sequences of SEQ ID NOs: 13, 14, 15, 16, 17, 18, 19, 20, 21, 22, 23, 24, 25, and/or 26 and canine antibody heavy chain IgG comprising one to six different CDRs comprising at least 80%, 85%, 90%, 95%, 98% or 99% sequence identity with the amino acid sequences of SEQ ID NOs: 27, 28, 29, 30, 31, 32, 33, 34, 35, 36, 37, 38, and/or 114, while still exhibiting the desired binding and functional properties. In another embodiment the antibody or antigen binding fragment of the present invention comprises a canine frame comprising of a combination of IgG heavy chain sequence with a kappa light chain having one or more of the above-mentioned CDR amino acid sequences with 0, 1, 2, 3, 4, or 5 conservative or non-conservative amino acid substitutions, while still exhibiting the desired binding and functional properties.

Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

Sequence similarity includes identical residues and non-identical, biochemically related amino acids. Biochemically related amino acids that share similar properties and may be interchangeable are discussed "Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Exemplary conservative substitutions are set forth in Table 3 directly below.

TABLE 3

Exemplary Conservative Amino Acid Substitutions

| Original residue | Conservative substitution |
|---|---|
| Ala (A) | Gly; Ser; |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 3 above.

Nucleic Acids

The present invention further comprises the nucleic acids encoding the immunoglobulin chains of murine anti-canine PD-1 and/or caninized murine anti-canine PD-1 antibodies and antigen binding fragments thereof disclosed herein (see Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the CDRs and antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); *Natl. Biomed. Res. Found.*, Washington, D.C.; Schwartz, R. M., et al., "Matrices for detecting distant relationships." in Atlas of Protein Sequence and Structure, vol. 5, suppl. 3." (1978), M. O. Dayhoff (ed.), pp. 353-358 (1978), *Natl. Biomed. Res. Found.*, Washington, D.C.; Altschul, S. F., *J. Mol. Biol.* 219:555-565 (1991); States, D. J., et al., *Methods* 3:66-70(1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, N.Y. (1997).

This present invention also provides expression vectors comprising the isolated nucleic acids of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

Epitope Binding and Binding Affinity

The present invention further provides antibodies or antigen binding fragments thereof that bind to amino acid residues of the same epitope of canine PD-1 as the murine anti-canine PD-1 antibodies disclosed herein. In particular embodiments the murine anti-canine PD-1 antibodies or antigen binding fragments thereof are also capable of inhibiting/blocking the binding of canine PD-1 to canine PD-L1.

A caninized murine anti-canine PD-1 antibody can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines.

Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

The present invention further includes antibody fragments of the murine anti-canine PD-1 antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$-$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_v$ fragment is a $V_L$ or $V_H$ region.

In one embodiment, the antibody or antigen binding fragment comprises a heavy chain constant region, e.g., a canine constant region, such as IgG-A, IgG-B, IgG-C and IgG-D canine heavy chain constant region or a variant thereof. In another embodiment, the antibody or antigen binding fragment comprises a light chain constant region, e.g., a canine light chain constant region, such as lambda or kappa canine light chain region or variant thereof. By way of example, and not limitation, the canine heavy chain constant region can be from IgG-B and the canine light chain constant region can be from kappa.

Antibody Engineering

Caninized murine anti-canine PD-1 antibodies of the present invention can be engineered to include modifications to canine framework and/or canine frame residues within the variable domains of a parental (i.e., canine) monoclonal antibody, e.g. to improve the properties of the antibody.

Experimental and Diagnostic Uses

Murine anti-canine PD-1 and/or caninized murine anti-canine PD-1 antibodies or antigen-binding fragments thereof of the present invention may also be useful in diagnostic assays for canine PD-1 protein, e.g., detecting its expression in specific tumor cells, tissues, or serum. Such diagnostic methods may be useful in various disease diagnoses, particularly certain cancers in canines.

For example, such a method comprises the following steps:
  (a) coat a substrate (e.g., surface of a microtiter plate well, e.g., a plastic plate) with a murine anti-canine PD-1 antibody or an antigen-binding fragment thereof;
  (b) apply a sample to be tested for the presence of canine PD-1 to the substrate;
  (c) wash the plate, so that unbound material in the sample is removed;
  (d) apply detectably labeled antibodies (e.g., enzyme-linked antibodies) which are also specific to the PD-1 antigen;
  (e) wash the substrate, so that the unbound, labeled antibodies are removed;
  (f) if the labeled antibodies are enzyme linked, apply a chemical which is converted by the enzyme into a fluorescent signal; and
  (g) detect the presence of the labeled antibody.

In a further embodiment, the labeled antibody is labeled with peroxidase which react with ABTS [e.g., 2,2'-azino-bis (3-ethylbenzthiazoline-6-sulphonic acid)] or 3,3',5,5'-Tetramethylbenzidine to produce a color change which is detectable. Alternatively, the labeled antibody is labeled with a detectable radioisotope (e.g., $^3$H) which can be detected by scintillation counter in the presence of a scintillant. Murine anti-canine PD-1 antibodies of the invention may be used in a Western blot or immuno protein blot procedure.

Such a procedure forms part of the present invention and includes for example:
  (i) contacting a membrane or other solid substrate to be tested for the presence of bound canine PD-1 or a fragment thereof with a murine anti-canine PD-1 antibody or antigen-binding fragment thereof of the present invention. Such a membrane may take the form of a nitrocellulose or vinyl-based [e.g., polyvinylidene fluoride (PVDF)] membrane to which the proteins to be tested for the presence of canine PD-1 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the murine anti-canine PD-1 antibody or antigen-binding fragment thereof, the membrane is optionally blocked, e.g., with non-fat dry milk or the like so as to bind non-specific protein binding sites on the membrane.
  (ii) washing the membrane one or more times to remove unbound murine anti-canine PD-1 antibody or an antigen-binding fragment thereof and other unbound substances; and
  (iii) detecting the bound murine anti-canine PD-1 antibody or antigen-binding fragment thereof.

Detection of the bound antibody or antigen-binding fragment may be by binding the antibody or antigen-binding fragment with a secondary antibody (an anti-immunoglobulin antibody) which is detectably labeled and, then, detecting the presence of the secondary antibody.

The murine anti-canine PD-1 antibodies and antigen-binding fragments thereof disclosed herein may also be used for immunohistochemistry. Such a method forms part of the present invention and comprises, e.g., (1) contacting a cell to be tested for the presence of canine PD-1 with a murine anti-canine PD-1 antibody or antigen-binding fragment thereof of the present invention; and (2) detecting the antibody or fragment on or in the cell. If the antibody or antigen-binding fragment itself is detectably labeled, it can be detected directly. Alternatively, the antibody or antigen-binding fragment may be bound by a detectably labeled secondary antibody which is detected.

Certain murine anti-canine PD-1 antibodies and antigen-binding fragments thereof disclosed herein may also be used for in vivo tumor imaging. Such a method may include injection of a radiolabeled murine anti-canine PD-1 antibodies or antigen-binding fragment thereof into the body of a canine to be tested for the presence of a tumor associated with canine PD-1 expression followed by nuclear imaging of the body of the patient to detect the presence of the labeled antibody or antigen-binding fragment e.g., at loci comprising a high concentration of the antibody or antigen-binding fragment which are bound to the tumor.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 [See e.g., Gordon et al., *International Rev. Neurobiol.* 67:385-440 (2005)].

Cross-Blocking Antibodies

Furthermore, an anti-canine PD-1 antibody or antigen-binding fragment thereof of the present invention includes any antibody or antigen-binding fragment thereof that binds to the same epitope in canine PD-1 to which the antibodies and fragments discussed herein bind and any antibody or antigen-binding fragment that cross-blocks (partially or fully) or is cross-blocked (partially or fully) by an antibody or fragment discussed herein for canine PD-1 binding; as well as any variant thereof.

The cross-blocking antibodies and antigen-binding fragments thereof discussed herein can be identified based on their ability to cross-compete with any of IB5, 3B6, 4D12, 7C9, 2H9, 5G5, and/or 2G9 in standard binding assays (e.g., BIACore®, ELISA, as exemplified below, or flow cytometry). For example, standard ELISA assays can be used in which a recombinant canine PD-1 protein is immobilized on the plate, one of the antibodies is fluorescently labeled and the ability of non-labeled antibodies to compete off the binding of the labeled antibody is evaluated. Additionally or alternatively, BIAcore® analysis can be used to assess the ability of the antibodies to cross-compete. The ability of a test antibody to inhibit the binding of, for example, IB5, 3B6, 4D12, 7C9, 2H9, 5G5, and/or 2G9, to canine PD-1 demonstrates that the test antibody can compete with IB5, 3B6, 4D12, 7C9, 2H9, 5G5, and/or 2G9 for binding to canine PD-1 and thus, may, in some cases, bind to the same epitope on canine PD-1 as IB5, 3B6, 4D12, 7C9, 2H9, 5G5, and/or 2G9. As stated above, antibodies and fragments that bind to the same epitope as any of the anti-canine PD-1 antibodies or fragments of the present invention also form part of the present invention.

Pharmaceutical Compositions and Administration

To prepare pharmaceutical or sterile compositions of a caninized murine anti-canine PD-1 antibody or antigen binding fragment thereof it can be admixed with a pharmaceutically acceptable carrier or excipient. [See, e.g., *Remington's Pharmaceutical Sciences and U.S. Pharmacopeia: National Formulary*, Mack Publishing Company, Easton, Pa. (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, N.Y.; Lieberman, et al. (eds.) (1990) *Pharmaceutical Dosage Forms: Tablets*, Marcel Dekker, N.Y.; Lieberman, et al. (eds.) (1990) *Pharmaceutical Dosage Forms: Disperse Systems*, Marcel Dekker, N.Y.; Weiner and Kotkoskie (2000) *Excipient Toxicity and Safety*, Marcel Dekker, Inc., New York, N.Y.]. In one embodiment, anti-PD-1 antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the murine anti-canine PD-1 antibody or antigen binding fragment thereof can be administered by an invasive route such as by injection. In further embodiments of the invention, a murine anti-canine PD-1 antibody or antigen binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer a murine anti-canine or a caninized murine anti-canine PD-1 antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis*, Marcel Dekker, New York, N.Y. (1991); Bach (ed.) *Monoclonal Antibodies and Peptide Therapy in Autoimmune Diseases*, Marcel Dekker, New York, N.Y. (1993); Baert, et al. *New Engl. J Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J Med.* 343:1594-1602 (2000)].

Determination of the appropriate dose is made by the veteranarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Antibodies or antigen binding fragments thereof disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of a caninized murine anti-canine PD-1 antibody in the subject's serum, such as 0.1, 0.3, 1, 3, 10, 30, 100, 300 µg/ml or more. In other embodiments, a caninized murine anti-canine PD-1 antibody of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

The antigenic peptides recognized by anti-canine PD-1 and PDL-1 mAbs also may be used as vaccines to elicit antibodies that block the binding of PD-1 to PDL-1 and result in T cell activation and enhancement of the immune response. Such vaccines may be useful as therapeutic vaccines for diseases such as cancer or to act as enhancers of the immune response to other vaccines. In order to use these antigenic peptides as vaccines, one or more of these peptides may be coupled chemically or through the techniques of recombinant DNA technology to another carrier protein in order to enhance the immunogenicity of these peptides and elicit peptide-specific antibodies. Techniques for coupling peptides to carrier proteins are known to those skilled in the art. Peptide vaccines may be used to vaccinate animals by IM, S/C, oral, spray or in ovo routes. Peptide vaccines may be used as subunit proteins expressed from bacterial, viral, yeast or baculovirus virus systems. Alternatively such peptide vaccines may be delivered following administration of a variety of viral or bacterial vectors that express such peptide vaccines as can be practiced by methods known to those skilled in the art. The peptide vaccines may be administered in doses from 1-1000 µg and may optionally contain an adjuvant and an acceptable pharmaceutical carrier.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of a caninized murine anti-canine PD-1 antibody or antigen binding fragment thereof of the present invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Other Combination Therapies

As previously described, a caninized murine anti-canine PD-1 antibody or antigen binding fragment thereof and/or an antigenic peptide of the present invention may be coadministered with one or other more therapeutic agents (such as a chemotherapeutic agent). The antibody may be linked to the agent (as an immunocomplex) or can be administered separately from the agent. In the latter case (separate administration), the antibody can be administered before, after or concurrently with the agent or can be co-administered with other known therapies.

Kits

Further provided are kits comprising one or more components that include, but are not limited to, an antibody or antigen binding fragment, as discussed herein, which specifically binds PD-1 (e.g., a caninized murine anti-canine PD-1 antibody or antigen binding fragment thereof) in association with one or more additional components including, but not limited to a pharmaceutically acceptable carrier and/or a chemotherapeutic agent, as discussed herein. The binding composition and/or the chemotherapeutic agent can be formulated as a pure composition or in combination with a pharmaceutically acceptable carrier, in a pharmaceutical composition.

In one embodiment, the kit includes a binding composition of the present invention (e.g., a caninized murine anti-canine PD-1 or a pharmaceutical composition thereof in one container (e.g., in a sterile glass or plastic vial) and a pharmaceutical composition thereof and/or a chemotherapeutic agent in another container (e.g., in a sterile glass or plastic vial).

If the kit includes a pharmaceutical composition for parenteral administration to a subject, the kit can also include a device for performing such administration. For example, the kit can include one or more hypodermic needles or other injection devices as discussed above. The kit can also include a package insert including information concerning the pharmaceutical compositions and dosage forms in the kit. Generally, such information aids pet owners and veterinarians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

Example 1

Canine PD-1 and PD-L1

Identification and Cloning of Canine PD-1:

A nucleic acid encoding a full length canine PD-1 (cPD-1) was identified through a search of the NCBI gene bank data bases (accession number XM_543338.4, SEQ ID NO: 1). The translated amino acid sequence SEQ ID NO: 2 (accession number XP-543338.3) corresponds to putative canine PD-1 protein which was further identified through searching the gene bank (NCBI) protein databases and aligning the identified amino acid sequence with murine, feline, and human PD-1 amino acid sequences. The DNA sequence corresponding to the full length canine PD-1 gene that was codon optimized for CHO cells was synthesized and cloned into a plasmid designated p96793. Comparison of DNA and protein sequences of predicted canine PD-1 with known PD-1 DNA and protein sequences led to the identification of the DNA sequences encoding the extra-cellular domain (ECD) of canine PD-1 (SEQ ID NO: 3) and the amino acid sequence of the ECD of canine PD-1 (SEQ ID NO: 4).

A DNA sequence encoding the ECD of canine PD-1 in addition to a GT linker and 8 histidine residues was synthesized and cloned into a plasmid designated LPD2726. A nucleic acid sequence (SEQ ID NO: 5) corresponding to the canine PD-1 ECD plus a GT linker and the Fc part of human IgG1 Fc gene was chemically synthesized and cloned into a plasmid designated LPD2727. Canine PD-1 ECD and the Fc part of human IgG1 Fc comprises the amino acid sequence of SEQ ID NO: 6.

Identification and Cloning of Canine PD-L1.

A nucleic acid encoding a full length canine PD-L1 was identified through a search of the NCBI gene bank data bases (accession number XM_541302.4; SEQ ID NO: 7). The translated amino acid sequence (accession number XP-541302.4; SEQ ID NO: 8) corresponding to the putative canine PD-L1 protein was identified by searching the gene bank (NCBI) protein databases and alignment of the identified sequence with known PD-L1 mouse and human sequences.

Comparison of DNA encoding canine PD-L1 with known PD-L1 sequences identified the DNA sequence corresponding to the ECD domain of canine PD-L1 (SEQ ID NO: 9; which was codon optimized for CHO cells). The predicted amino acid sequence of the ECD of canine PD-L1 is SEQ ID NO: 10. DNA encoding PD-L1 ECD plus GT linker and 8 histidine residues was synthesized and cloned into a plasmid designated LPD2695.

A DNA sequence encoding the amino acid sequence of canine PD-L1 ECD plus GT linker and the Fc part of human IgG1 Fc (SEQ ID NO: 11) was chemically synthesized and cloned into a plasmid designated LPD2697. Canine PD-L1 ECD plus GT linker and the Fc part of human IgG1 comprises the amino acid sequence of SEQ ID NO: 12. Table 4 contains a description of the expression plasmids mentioned above.

TABLE 4

PLASMIDS COMPRISING DNA ENCODING PD-1 or PD-L1

| PLASMID NAME | EXPRESSED GENE |
| --- | --- |
| P96793 | Canine PD-1 |
| LPD2726 | Canine PD-1 ECD-8HIS |
| LPD2727 | Canine PD-1 ECD-/Human IgG1 Fc |
| LPD2695 | Canine PD-L1 ECD-8HIS |
| LPD2697 | Canine PD-L1 ECD-/Human IgG1 Fc |

Expression of PD-1 and PD-L1 Proteins:

Expression plasmids encoding the PD-1ECD-HIS, PD-1ECD-Fc, PDL-1 ECD-HIS, and PD-L1ECD-Fc proteins were transfected into HEK 293 cells and the proteins were purified from the supernatant of transfected cells using Protein A for Fc fusion proteins or Nickel ($Ni^{2+}$) column chromatography for HIS-tagged proteins. Purified proteins were used for: ELISA or binding assays as detailed below. Expressed proteins were analyzed by SDS-PAGE gels.

```
Full length canine PD-1 DNA sequence: signal
sequence underlined and in bold
SEQ ID NO: 1 is without the signal sequence;
SEQ ID NO: 105 is with the signal sequence.
atggggagccggcgggggcccctggccgctcgtctgggccgtgctgcagct gggctggtggccaggatggctcctagactcccctgacaggccctggagcc cgctcaccttctccccggcgcagctcacggtgcaggagggagagaacgcc acgttcacctgcagcctggccgacatccccgacagcttcgtgctcaactg gtaccgcctgagcccccgcaaccagacggacaagctggccgcctccagg aggaccgcatcgagccgggccgggacaggcgcttccgcgtcatgcggctg cccaacgggcgggacttccacatgagcatcgtcgctgcgcgcctcaacga cagcggcatctacctgtgcggggccatctacctgccccccaacacacaga tcaacgagagtccccgcgcagagctctccgtgacggagagaaccctggag ccccccacacagagcccagcccccacccagactcagcggccagttgca ggggctggtcatcggcgtcacgagcgtgctggtgggtgtcctgctactgc tgctgctgacctgggtcctggccgctgtcttccccagggccacccgaggt gcctgtgtgtgcgggagcgaggacgagcctctgaaggagggccccgatgc agcgcccgtcttcaccctggactacggggagctggacttccagtggcgag agaagacgccggagccccggcgccctgtgccccggagcagaccgagtat gccaccatcgtcttcccgggcaggccggcgtccccgggccgcagggcctc ggccagcagcctgcaggagcccagcctccgagcccgaggacggacccg gcctgtggcccctctga Full length canine PD-1 Amino acid sequence:
signal sequence underlined and
in bold
SEQ ID NO: 2 is without the signal sequence;
SEQ ID NO: 106 is with the signal sequence.
MGSRRGPWPLVWAVLQLGWWPGWLLDSPDRPWSPLTFSPAQLTVQEGENA

TFTCSLADIPDSFVLNWYRLSPRNQTDKLAAFQEDRIEPGRDRRERVMRL

PNGRDFHMSIVAARLNDSGIYLCGAIYLPPNTQINESPRAELSVTERTLE

PPTQSPSPPPRLSGQLQGLVIGVTSVLVGVLLLLLLTWVLAAVFPRATRG

ACVCGSEDEPLKEGPDAAPVFTLDYGELDFQWREKTPEPPAPCAPEQTEY

ATIVFPGRPASPGRRASASSLQGAQPPSPEDGPGLWPL

Canine PD-1 extracellular domain_DNA sequence:
SEQ ID NO: 3 (Codon optimized for expression in
CHO cells)
ctggattccccgacagaccctggagccctctcaccttctccctgccca gctgaccgtccaggaaggcgagaatgccaccttcacctgcagcctcgccg acatccccgacagcttcgtgctgaactggtacagactgagcccaggaac cagaccgacaagctggccgctttccaggaggacaggatcgaacccggcag ggacaggagtttagggtcatgaggctgcccaacggcagggacttccaca tgtccatcgtggccgccagactgaacgactccggcatctacctgtgcggc gctatctacctgccccccaacacccagatcaacgagagcccagggccga actgagcgtgacagagagaaccctggaacctcccacccagagcccttccc ctcctcctagactgagcggacagctgcagggcctggtg Canine PD-1 extracellular domain: SEQ ID NO: 4:
LDSPDRPWSPLTFSPAQLTVQEGENATFTCSLADIPDSFVLNWYRLSPRN

QTDKLAAFQEDRIEPGRDRRFRVMRLPNGRDFHMSIVAARLNDSGIYLCG

AIYLPPNTQINESPRAELSVTERTLEPPTQSPSPPPRLSGQLQGLV

Canine PD-1 extracellular domain - human IgG1
Fc DNA sequence: SEQ ID NO: 5 (Codon optimized
for expression in HEK-293 cells)
ctggattccccgacagaccctggagccctctcaccttctccctgccca gctgaccgtccaggaaggcgagaatgccaccttcacctgcagcctcgccg acatccccgacagcttcgtgctgaactggtacagactgagcccaggaac cagaccgacaagctggccgctttccaggaggacaggatcgaacccggcag ggacaggagtttagggtcatgaggctgcccaacggcagggacttccaca tgtccatcgtggccgccagactgaacgactccggcatctacctgtgcggc gctatctacctgccccccaacacccagatcaacgagagcccagggccga actgagcgtgacagagagaaccctggaacctcccacccagagcccttccc ctcctcctagactgagcggacagctgcagggcctggtgggtaccgacaaa actcacacatgcccaccgtgcccagcacctgaactcctggggggaccgtc agtcttcctcttccccccaaaacccaaggacaccctcatgatctcccga cccctgaggtcacatgcgtggtggtggacgtgagccacgaagaccctgag gtcaagttcaactggtacgtggacggcgtggaggtgcataatgccaagac aaagccgcgggaggagcagtacaacagcacgtaccgtgtggtcagcgtcc tcaccgtcctgcaccaggactggctgaatggcaaggagtacaagtgcaag gtctccaacaaagccctcccagcccccatcgagaaaaccatctccaaagc caaagggcagccccgagaaccacaggtgtacaccctgccccatcccggg atgagctgaccaagaaccaggtcagcctgacctgcctggtcaaaggcttc
```

-continued

```
tatcccagcgacatcgccgtggagtgggagagcaatgggcagccggagaa caactacaagaccacgcctcccgtgctggactccgacggctccttcttcc tctacagcaagctcaccgtggacaagagcaggtggcagcaggggaacgtc ttctcatgctccgtgatgcatgaggctctgcacaaccactacacgcagaa gagcctctccctgtctccgggtaaatga
```

Canine PD-1 extracellular domain - human IgG1 Fc fusion protein: signal sequence underlined and in bold:
SEQ ID NO: 6 is without the signal sequence; SEQ ID NO: 113 is with the signal sequence

MNFLLSWVHWSLALLLYLHHAKWSQALDSPDRPWSPLTFSPAQLTVQEGE

NATFTCSLADIPDSFVLNWYRLSPRNQTDKLAAFQEDRIEPGRDRRERVM

RLPNGRDFHMSIVAARLNDSGIYLCGAIYLPPNTQINESPRAELSVTERT

LEPPTQSPSPPPRLSGQLQGLVGTDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Full length canine PD-L1 DNA sequence: signal sequence underlined and in bold
SEQ ID NO: 7 is without the signal sequence;
SEQ ID NO: 107 is with the signal sequence.

<u>atgagaatgtttagtgtctttacattcatggcctactgccatttgctaaa</u>

<u>agcattt</u>acgatcacagtttctaaggacctgtatgtggtagagtatggtg gcaatgtgacaatggaatgcaaattcccgtggaaaaacagttaaacttg tttgcactaatcgtctactgggaaatggaggataaaaaaattatacaatt tgtgaatggaaaggaagacctgaaagttcagcacagcagctacagccaga gggctcagctattgaaggaccagctcttcttggggaaggctgcgcttcag atcacagatgtgagattgcaggatgcaggggtttactgctgcttgatcgg ctatggcggtgctgactacaagcggattactttgaaagttcatgccccgt accgcaacatcagccaaagaatttctgtggatcctgtcacctctgaacat gaactaatgtgtcaggctgagggttaccctgaggctgaagtcatctggac aagcagtgaccaccgagtcctgagtggcaaaaccaccatcactaattcca ataggggaagagaagcttttcaatgtgaccagcacgctgaacatcaatgca acagctaatgagattttctactgcacttttcaaagatcaggtcctgagga aaacaatactgccgagttggtcatcccagaacgactgcccgttccagcaa gtgagaggactcatttcatgattctgggacctttcctgttgcttcttggt gtagtcctggcagtcactttctgtctaaaaaacatgggagaatgatgga tgtgaaaatgttgcacccgagataggaactcaaagaaacgaaatgata tacaatttgaagagacataa
```

Full length canine PD-L1: signal sequence underlined and in bold
SEQ ID NO: 8 is without the signal sequence;
SEQ ID NO: 108 is with the signal sequence.

MRMESVFTFMAYCHLLKAFTITVSKDLYVVEYGGNVTMECKFPVEKQLNL

FALIVYWEMEDKKIIQFVNGKEDLKVQHSSYSQRAQLLKDQLFLGKAALQ

ITDVRLQDAGVYCCLIGYGGADYKRITLKVHAPYRNISQRISVDPVTSEH

ELMCQAEGYPEAEVIWTSSDHRVLSGKTTITNSNREEKLFNVTSTLNINA

TANEIFYCTFQRSGPEENNTAELVIPERLPVPASERTHFMILGPFLLLLG

VVLAVTFCLKKHGRMMDVEKCCTRDRNSKKRNDIQFEET

Canine PD-L1 extracellular domain DNA sequence:
SEQ ID NO: 9 (Codon optimized for expression in CHO cells)

```
tttaccataccgtgtccaaggacctgtacgtggtcgagtacggcggcaa tgtgaccatggagtgcaagttccccgtggagaagcagctgaacctgttcg ccctcatcgtgtactgggagatggaggacaagaagatcatccagttcgtg aacggcaaggaggacctgaaggtgcagcactccagctactcccagagagc ccagctgctgaaggaccagctgttcctgggcaaggccgccctgcagatca ccgacgtgagactgcaggacgccggcgtgtattgctgcctgatcggctac ggaggcgccgactacaagaggatcaccctgaaggtgcatgcaccctacag gaacatcagccagaggatcagcgtcgatcccgtgaccagcgagcacgagc tgatgtgccaagccgagggctatcccgaggccgaagtgatctggaccagc agcgaccacagggtcctgagcggcaagaccaccatcaccaacagcaacag ggaggagaagctgttcaacgtgaccagcaccctcaacatcaacgccaccg ccaacgagatcttctactgcaccttccagagagcggccccgaagagaac aacaccgccgagctggtgatccccgagagactgcctgtgcctgccagcga gaggacccac
```

Canine PD-L1 extracellular domain protein:
SEQ ID NO: 10

FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYCCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTH

Canine PD-L1 extracellular domain - human IgG1 Fc DNA sequence: SEQ ID NO: 11 (Codon optimized for expression in HEK-293 cells)

```
tttaccataccgtgtccaaggacctgtacgtggtcgagtacggcggcaa tgtgaccatggagtgcaagttccccgtggagaagcagctgaacctgttcg ccctcatcgtgtactgggagatggaggacaagaagatcatccagttcgtg aacggcaaggaggacctgaaggtgcagcactccagctactcccagagagc ccagctgctgaaggaccagctgttcctgggcaaggccgccctgcagatca ccgacgtgagactgcaggacgccggcgtgtattgctgcctgatcggctac ggaggcgccgactacaagaggatcaccctgaaggtgcatgcaccctacag gaacatcagccagaggatcagcgtcgatcccgtgaccagcgagcacgagc tgatgtgccaagccgagggctatcccgaggccgaagtgatctggaccagc agcgaccacagggtcctgagcggcaagaccaccatcaccaacagcaacag ggaggagaagctgttcaacgtgaccagcaccctcaacatcaacgccaccg ccaacgagatcttctactgcaccttccagagagcggccccgaagagaac aacaccgccgagctggtgatccccgagagactgcctgtgcctgccagcga gaggacccacggtaccgacaaaactcacacatgcccaccgtgcccagcac
```

-continued

```
ctgaactcctgggggaccgtcagtcttcctcttcccccaaaacccaag gacaccctcatgatctcccggacccctgaggtcacatgcgtggtggtgga cgtgagccacgaagaccctgaggtcaagttcaactggtacgtggacggcg tggaggtgcataatgccaagacaaagccgcgggaggagcagtacaacagc acgtaccgtgtggtcagcgtcctcaccgtcctgcaccaggactggctgaa tggcaaggagtacaagtgcaaggtctccaacaaagccctcccagccccca tcgagaaaaccatctccaaagccaaagggcagccccgagaaccacaggtg tacaccctgcccccatcccgggatgagctgaccaagaaccaggtcagcct gacctgcctggtcaaaggcttctatcccagcgacatcgccgtggagtggg agagcaatgggcagccggagaacaactacaagaccacgcctcccgtgctg gactccgacggctccttcttcctctacagcaagctcaccgtggacaagag caggtggcagcaggggaacgtcttctcatgctccgtgatgcatgaggctc tgcacaaccactacacgcagaagagcctctccctgtctccgggtaaatga
```

Canine PD-L1 extracellular domain - human IgG1
Fc fusion protein: SEQ ID NO: 12

FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYCCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHGTDKTHTCPPCPAPELLGGPSVFLEPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

Example 2

Anti-Canine PD-1 Antibodies

Generation of Anti-Canine PD1 Monoclonal Antibodies:

A total of three Balb/c mice were immunized multiple times (with 10 µg each time) over a 17 day period. The immunizing antigen was the canine PD-1 ECD-Fc fusion protein. Following immunization, serum was collected from each mouse and tested for reactivity with canine PD-1 ECD-HIS tagged protein. The spleen cells of the mouse with the highest serum anti-PD-1 ECD-HIS titer were fused to the myeloma P3X63Ag8.653 cell line. Approximately 2 weeks following fusion, supernatant from putative hybridoma cells were tested by ELISA for their reactivity to the PD-1 ECD-HIS tagged protein. Hybridomas producing strong positive signals in the ELISA were subcloned by limiting dilution and tested again for reactivity to canine PD-1 ECD-HIS tagged protein.

Confirmation of Monoclonal Murine Antibodies Reactivity Against Canine PD-1:

The reactivity of antibodies secreted by hybridomas to ECD of canine PD-1 was confirmed by ELISA. Hybridoma cells were cultured using CELLine bioreactors (Integrabiosciences) for 10-30 days. Cells were initially maintained in DMEM supplemented with 4 mM L-glutamine and 10% Ultra Low IgG fetal bovine serum (FBS) from Gibco. Hybridoma cells were seeded in CELLine bioreactor cell chambers at a cell density of approximately $2 \times 10^6$ cells/mL in 15 mL of the same medium with the FBS concentration increased to 20%. The outer chamber was filled with 1 L of nutrient medium (DMEM with 4 mM L-glutamine and 2% standard FBS). Hybridoma cells in the cell chamber were expanded to approximately $2.5 \times 10^7$ cells/mL over 3-7 days. Then, 10 mL of cell suspension was harvested from the cell chamber and replaced with fresh media to allow for re-expansion of cells and subsequent harvests. This procedure was repeated as necessary to obtain adequate amounts of mAb from each hybridoma clone. Harvested cell suspensions were centrifuged and the supernatants were filtered through 0.2 micron filter membranes. For antibody purification, each clone's supernatant was purified using a Protein G Sepharose 4 Fast flow 5 mL column (GE Healthcare) by gravity flow. After washing with Tris-EDTA (TE) buffer pH 8.0, bound antibodies were eluted using 0.1 M glycine buffer, pH 2.7, followed by pH neutralization using 1 M Tris, pH 8.0. Antibodies were concentrated and buffer exchanged into phosphate-buffered saline (PBS) using Centriprep YM-10.10 kDa NMWL centrifugal filter units (Millipore). Antibody concentrations were quantified using spectrophotometry.

Purified anti-canine PD-1 mAbs were tested for reactivity with the HIS-tagged ECD domain of canine PD-1 by ELISA as follows: HIS-tagged canine PD-1 ECD protein is diluted to 10 µg/mL in coating buffer (Carbonate/Bicarbonate pH 9.0) and dispensed at 100 µl/well in 96-well flat bottomed ELISA plates (NUNC). The plates are incubated at 4° C. overnight. The plates are then washed three times with phosphate buffered saline containing 0.05% Tween-20 (PBST). Next, 200 µl of blocking buffer (5% skim milk in PBST) is added to each well and the plates are incubated at 37° C. for 60 minutes. The plates are then washed three times with PBST. Next, 100 µl of test mAbs diluted in blocking buffer is added to the first wells of the appropriate columns. Test mAbs are then diluted two-fold to the appropriate plate position. Following incubation of the plates at 37° C. for 60 minutes, the plates are washed three times with PBST. Next, 100 µl per well of a 1:2,000 dilution of a horseradish peroxidase conjugated goat anti-mouse IgG (KPL) is added to the plates, which are then incubated at 37° C. for 60 minutes. Then the plates are washed three times with PBST, and 100 µl/well of 3,3',5,5' tetramethyl benzidine, (TMB) substrate (from KPL) is added to the plates. The color reaction is allowed to develop for 5-20 minutes at 37° C. prior to measuring absorbance at 650 nm.

CHO Cells Expressing Canine PD-1 Protein:

The full length canine PD-1 gene was cloned into plasmid p96793. In this plasmid the expression of the PD-1 protein is driven by an hCMV promoter. CHO DXB 11 cells (dhfr−) were maintained in MEM-alpha (Gibco) supplemented with 10% fetal bovine serum. Transfection of CHO cells with plasmid p96793 was carried out in 75 cm² flasks containing approximately $6 \times 10^6$ cells by liposome-mediated gene delivery using Lipofectamine (Invitrogen). After 48 hours, cells were passaged into MEM-alpha medium without nucleosides, supplemented with 10% FBS and 400 µg/mL hygromycin B (selective medium). Limited-dilution cloning was performed on the pool of dhfr+, hygromycin resistant cells. Clones were assessed for expression of canine PD-1 by immunofluorescence assay. Briefly, cell monolayers were fixed in 96 well plates with 80% acetone. Fixed and dried cell monolayers were then incubated for 1 hour with a polyclonal goat anti-human PD-1 antibody (R&D Systems). Plates were washed with PBS, then incubated for 1 hour with a fluorescein-labeled rabbit anti-goat IgG antibody (KPL). Plates were washed with PBS. Clones exhibiting fluorescence were expanded and cell stocks were established.

Reactivity of Mouse mAbs Against Canine PD-1 Proteins Expressed on CHO Cells:

The reactivity of mouse anti-canine PD-1 mAbs with canine PD-1 on CHO cells was determined by a cell-based assay using CHO cells that express PD-1. Briefly, the CHO cells expressing canine PD-1 were cultured to 80-100% confluency in 50 µl media (DMEM/HAM's F12, 10% FBS). Next, 50 µl of media containing various concentrations of purified mAbs were added for 1 hour at 37° C. Following three washes with PBS-Tween, 100 µl of goat anti-mouse horse raddish peroxidase (HRP) diluted 1:1000 in culture media was added for one hour at 37° C. After three additional washes with PBS-Tween, bound mAbs were visualized with a peroxidase substrate (TMB). The absorbance increase due to peroxidase activity at 450 nm was measured in a microplate reader.

Binding Studies of Mouse Anti-Canine PD-1 mAbs and Caninized Mouse Anti-Canine PD-1 mAbs with Canine PD-1

Approximately 70 resonance units (RU) of the canine PD-1 antigen was immobilized directly by amine coupling. Affinity measurements were made via label-free surface plasmon resonance based technology (e.g., Biacore® T200) with an association time of 300 seconds, a dissociation time of 1200 seconds, and at concentrations of 50, 100, 200 (×2) 400, and 800 nanomolar (nM). A fitting model of 1:1 binding was used. The antigen (canine PD-1) was immobilized on the sensor chip through amine coupling and the four antibodies as indicated in Table 5 below, were used as analytes that flowed through the antigen surface. The results demonstrated that the binding affinities of the anti-canine PD-1 antibodies of the present invention for the canine PD-1 antigen were strong, having nanomolar and even subnanomolar dissociation constants (Kd). Moreover, the mouse anti-canine PD-1 monoclonal antibody and the corresponding caninized mouse anti-canine PD-1 monoclonal antibody from the same clone yielded strikingly similar Kd values (see Table 5 below).

TABLE 5

Binding Constant Determinations

| Antibody | $k_{on}$ ($k^1$) $M^{-1}s^{-1}$ | $k_{off}$ ($k^{-1}$) $s^{-1}$ | Kd M | Chi$^2$ (RU$^2$) | Rmax (RU) |
|---|---|---|---|---|---|
| Murine 2H9 | $2.3 \times 10^4$ | $\leq 5 \times 10^{-6\#}$ | $\leq 2.0 \times 10^{-10\#}$ | 0.19 | 25.6 |
| Caninized 2H9 | $1.0 \times 10^4$ | $5.9 \times 10^{-6}$ | $5.9 \times 10^{-10}$ | 0.10 | 27.7 |
| Murine 3B6 | $1.8 \times 10^4$ | $3.4 \times 10^{-5}$ | $2.0 \times 10^{-9}$ | 0.13 | 48.7 |
| Caninized 3B6 | $1.6 \times 10^4$ | $4.7 \times 10^{-5}$ | $2.9 \times 10^{-9}$ | 0.07 | 49.9 |

The off-rate was so slow that it was below the detection limit of the instrument used.

Ligand Blockade by Mouse Anti-Canine PD1 mAbs:

A cell-based ELISA (CELISA) assay based on the CHO cell line expressing canine PD-1 was used for mouse mAbs which react with canine PD-1 (cPD-1). Ligand blockade was confirmed using this assay in conjunction with biotinylated cPD-L1/Fc protein. Briefly, seed cPD-1 CHO cells were placed in 96-well plates at 4×10$^4$ cells per well and the cells were incubated at 37° C. for 18-24 hours till they are 95-100% confluent. The cell culture media was aspirated off, and the plates were washed 3× with PBS+0.05% Tween20 and 1×CHO media. Three-fold serial dilutions were made of anti-cPD1 mAbs in CHO media, starting at 30 µg/mL, and 50 µL/well of each antibody dilution were added down the plate. The incubation was performed at 37° C., 5% $CO_2$ with shaking for 30 min. 50 µL/well of cPD-L1-Fc-biotin (2 µg/ml in CHO media stock) was added and the incubation at 37° C., 5% $CO_2$ was continued with shaking for 45 min. The plates were washed 6 times with PBS+0.05% Tween 20. 100 ul/well of Streptavidin-HRP (1:2000) in CHO media was added followed by a incubation for 30-60 min at 37° C./5% $CO_2$. The plates were washed 5 times with PBS+0.05% Tween20 and then 100 µl/well of TMB color developing substrate was added. The color development was stopped by adding 50 µl/well of 1M phosphoric acid. The optical density (O.D.) at A450-A620 was measured using an ELISA plate reader.

Reactivity of Mouse mAbs with PD-1 Expressed on PBMC from Healthy and Cancer-Ridden Dogs:

PBMC were prepared from EDTA blood samples obtained from healthy dogs and dogs with cancer, using Ficoll separation. PBMC were resuspended in FACS buffer (PBS, 1% FBS, and 0.1% sodium azide) added at a concentration of 2.5×10$^5$ cells per well, and incubated with test monoclonal antibodies (mAb) at various concentrations. Cells were incubated for 30 min at room temp, then washed twice. Cells were then resuspended and incubated with Alexa-488 conjugated donkey anti-mouse IgG (H+L chain) for 30 min at room temp, then washed twice. Cells were then incubated with PB and PE conjugated antibodies to canine CD4 and CD8 for 30 min, and then washed. Cells were then resuspended in FACS buffer and analyzed by flow cytometry to determine the percentage of CD4 or CD8 T cells positive for binding of the PD-1 mAbs. Controls included cells incubated with secondary antibody only, or with irrelevant isotype matched mAbs.

Cytokine Release from PBMC Obtained from Healthy and Cancer-Ridden Dogs:

PBMC were prepared from EDTA blood samples obtained from healthy dogs and dogs with cancer, using Ficoll separation. Cells were washed 3 times, and resuspended in complete tissue culture medium at a concentration of 2.5×10$^5$ cells per well in triplicate wells in 96-well plates. Cells were activated with concanavalin A at 1 µg/ml. Test antibodies were added at various concentrations and the cultures were incubated for 96 hours. Controls included cells incubated with conA and no antibody, or conA and irrelevant isotype-matched antibodies. After 96 hours in culture, supernatants were collected and assayed for IFN-gamma release, using a commercial canine IFN-gamma ELISA kit (R & D Systems).

Cloning and Identification of DNA Sequences Corresponding to Mouse mAbs Variable Regions:

The DNA sequence of mouse VH and VL chains and the DNA sequences encoding their CDRs are identified following isolation of mRNA from each hybridoma using standard molecular biology methods. The SEQ ID NOs. of predicted amino acid sequences of the CDRs from these hybridomas are listed below:

Notably, there is substantial homology between the amino acid sequences of the CDRs for each of the seven mouse anti-Canine PD-1 antibodies exemplified.

| CDR AMINO ACID SEQUENCES | | SEQ ID NO. |
|---|---|---|
| VL CDR1 | | |
| 1B5 | Lys Ser Ser Gln Ser Leu Leu Asn Ser Val Asn Gln Lys Asn Tyr Leu Ala | 13 |
| 2G9 | Arg Ser Ser Gln Asn Ile Val His Ser Asn Gly Asn Thr Tyr Leu Glu | 14 |
| 2H9 | His Ala Ser Gln Asn Ile Asn Val Trp Leu Ser | 15 |
| 3B6 | Lys Ser Ser Gln Ser Leu Leu Asn Ser Val Asn Gln Lys Asn Tyr Leu Ala | 13 |
| 4D12 | Lys Ser Ser Gln Ser Leu Leu Asn Ser Val Asn Gln Lys Asn Tyr Leu Ala | 13 |
| 5G5 | His Ala Ser Gln Asn Ile Asn Val Trp Leu Ser | 15 |
| 7C9 | Lys Ser Ser Gln Ser Leu Leu Asn Ser Val Asn Gln Lys Asn Tyr Leu Ala | 13 |
| VL CDR2 | | |
| 1B5 | Phe Ala Ser Thr Arg Val Ser | 16 |
| 2G9 | Lys Val Ser Asn Arg Phe Ser | 17 |
| 2H9 | Lys Ala Ser His Leu His Thr | 18 |
| 3B6 | Phe Ala Ser Ala Arg Val Ser | 19 |
| 4D12 | Phe Ala Ser Thr Arg Ile Ser | 20 |
| 5G5 | Lys Ala Ser Asn Leu His Thr | 21 |
| 7C9 | Phe Ala Ser Thr Arg Val Ser | 16 |
| VL CDR3 | | |
| 1B5 | Gln Gln Tyr Phe Ser Thr Pro Leu Thr | 22 |
| 2G9 | Phe Gln Gly Ser His Val Pro Tyr Thr | 23 |
| 2H9 | Gln Gln Gly Gln Ser Trp Pro Leu Thr | 24 |
| 3B6 | Gln Gln Tyr Phe Ser Thr Pro Leu Thr | 25 |
| 4D12 | Gln Gln Tyr Phe Ser Thr Pro Leu Thr | 25 |
| 5G5 | Gln Gln Gly Gln Ser Tyr Pro Leu Thr | 26 |
| 7C9 | Gln Gln Tyr Phe Ser Thr Pro Leu Thr | 22 |
| VH CDR1 | | |
| 1B5 | Gly Tyr Thr Phe Thr Thr Tyr Gly Met Ser | 27 |
| 2G9 | Gly Tyr Thr Phe Thr Arg Tyr Asn Met His | 28 |
| 2H9 | Gly Phe Asn Ile Lys Asn Thr Tyr Met His | 29 |
| 3B6 | Gly Tyr Thr Phe Thr Thr Tyr Gly Met Ser | 27 |
| 4D12 | Gly Tyr Thr Phe Thr Thr Tyr Gly Met Ser | 27 |
| 5G5 | Gly Phe Asn Ile Lys Asn Thr Tyr Met His | 29 |
| 7C9 | Gly Phe Ser Leu Thr Ser Tyr Gly Val His | 30 |
| VH CDR2 | | |
| 1B5 | Trp Ile Asn Ile Tyr Ser Gly Ile Pro Thr Tyr Ala Asp Asp Phe Lys Gly | 31 |
| 2G9 | Thr Ile Tyr Pro Gly Tyr Gly Asp Thr Ser Tyr Asn Gln Lys Phe Lys Gly | 32 |
| 2H9 | Arg Ile Ala Pro Ala Asn Val Asp Thr Lys Tyr Ala Pro Lys Phe Gln Gly | 33 |
| 3B6 | Trp Ile Asn Ile Tyr Ser Gly Ile Pro Thr Tyr Ala Asp Asp Phe Lys Gly | 31 |
| 4D12 | Trp Ile Asn Ile Tyr Ser Gly Met Pro Thr Tyr Ala Asp Asp Phe Lys Gly | 34 |

CDR AMINO ACID SEQUENCES

| | | SEQ ID NO. |
|---|---|---|
| 5G5 | Arg Ile Asp Pro Ala Asn Val Asn Thr Lys Tyr Ala Pro Lys Phe Gln Gly | 35 |
| 7C9 | Trp Ile Asn Ile Tyr Ser Gly Ile Pro Thr Tyr Ala Asp Asp Phe Lys Gly | 31 |

VH CDR3

| | | |
|---|---|---|
| 1B5 | Phe Asp Gly Pro Asp Tyr | 36 |
| 2G9 | Glu Phe Ala Asp Asp Tyr Pro Ile Pro Pro Phe Asp Tyr | 37 |
| 2H9 | Ile Tyr Tyr Asp Tyr Asp Gly Asp Ile Asp Val | 38 |
| 3B6 | Phe Asp Gly Pro Asp Tyr | 36 |
| 4D12 | Phe Asp Gly Pro Asp Tyr | 36 |
| 5G5 | Ile Phe Tyr Asp Tyr Asp Gly Asp Ile Asp Val | 114 |
| 7C9 | Phe Asp Gly Pro Asp Tyr | 36 |

| Canonical structures (classes) for VH chain CDRs | |
|---|---|
| mAbs: 4D12, 3B6, 7C9, and 1B5: | CDR: H1-1; CDR2: H2-1; CDR3: H3-6 |
| mAb: 5G5: | CDR: H1-1; CDR2: H2-1; CDR3: H3-11 |
| mAb: 2H9 | CDR: H1-1; CDR2: H2-2A; CDR3: H3-11 |
| mAb: 2G9 | CDR: H1-1; CDR2: H2-2A; CDR3: H3-13 |

| Canonical structures (classes) for VL chain CDRs | |
|---|---|
| mAbs: 4D12, 3B6, 7C9, IB5: | CDRL: L1-3; CDR2: L2-1; CDR3: L3-1 |
| mAb: 5G5: | CDR: L1-2A; CDR2: L2-1; CDR3: L3-1 |
| mAb: 2H9 | CDR: L1-2A; CDR2: L2-1; CDR3: L3-1 |
| mAb: 2G9 | CDR: L1-4; CDR2: L2-1; CDR3: L3-1 |

Example 3

Mutant Canine IgG-B Antibodies Specific to PD-1

There are four known IgG heavy chain subtypes of dog IgG and they are referred to as IgG-A, IgG-B, IgG-C, and IgG-D. The two known light chain subtypes are referred to as lambda and kappa. However, besides binding and activating of canine immune cells, a canine or caninized antibody against PD-1 optimally has two attributes:

1. lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has a high level of ADCC activity. IgG-C also has considerable ADCC activity. On the other hand, IgG-A binds weakly to protein A, but displays undesirable ADCC activity. Moreover, neither IgG-C nor IgG-D can be purified on protein A columns, although IgG-D display no ADCC activity. The present invention overcomes this difficulty by providing mutant canine IgG-B antibodies specific to PD-1; such antibodies lack effector functions such as ADCC and can be easily of purified using industry standard protein A chromatography. The exact modifications are shown in FIGS. 8A-8B.

The IgG-B variants with reduced effector functions described encompass a first IgG-B variant in which an aspartic acid (D 277) and an asparagine (N 325) residue is each mutated to an alanine residue [cIgGB(−) ADCC], a second variant in which the hinge region of IgG-B is replaced by the hinge region of IgG-D [cIgGB(+) D-hinge], and a third variant in which the hinge region of IgG-B is replaced with the hinge region of IgG-A [cIgGB(+) A-hinge]. Additionally, the second and third variants also include replacement of the same aspartic acid and asparagine residues of the first variant with an alanine residue. The numbering of the aspartic acid and asparagine residues mutated in this invention is based on the numbering scheme described for canine IgG heavy chains in Tang et al., [*Vet Immunol and Immunopathol*, 80:259-270 (2001)].

Canine IgGB wt
SEQ ID NO: 39
SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVP

KRENGRVPRPPDCPKCPAPEMLGGPSVFIFPPKPKDTLLIARTPEVTCVV

VDLDPEDPEVQISWFVDGKQMQTAKTQPREEQFNGTYRVVSVLPIGHQDW

LKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLS

VDKSRWQRGDTFICAVMHEALHNHYTQESLSHSPGK

Canine IgGB(+)A-hinge
SEQ ID NO: 40
SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVF

NECRCTDTPPCPAPEMLGGPSVFIFPPKPKATLLIARTPEVTCVVVDLDP

EDPEVQISWFVDGKQMQTAKTQPREEQFAGTYRVVSVLPIGHQDWLKGKQ

FTCKVNNKALPSPIERTISKARGQAHQPSVYVLPPSREELSKNTVSLTCL

IKDFFPPDIDVEWQSNGQQEPESKYRTTPPQLDEDGSYFLYSKLSVDKSR

WQRGDTFICAVMHEALHNHYTQESLSHSPGK

Canine IgGB(+)D-hinge

SEQ ID NO: 41

SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVP

KESTCKCISPCPAPEMLGGPSVFIFPPKPKATLLIARTPEVTCVVVDLDP

EDPEVQISWFVDGKQMQTAKTQPREEQFAGTYRVVSVLPIGHQDWLKGKQ

FTCKVNNKALPSPIERTISKARGQAHQPSVYVLPPSREELSKNTVSLTCL

IKDFFPPDIDVEWQSNGQQEPESKYRTTPPQLDEDGSYFLYSKLSVDKSR

WQRGDTFICAVMHEALHNHYTQESLSHSPGK

Canine IgGB(-)ADCC

SEQ ID NO: 42

SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVP

KRENGRVPRPPDCPKCPAPEMLGGPSVFIFPPKPKATLLIARTPEVTCVV

VDLDPEDPEVQISWFVDGKQMQTAKTQPREEQFAGTYRVVSVLPIGHQDW

LKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLS

VDKSRWQRGDTFICAVMHEALHNHYTQESLSHSPGK

Example 4

Antibody Sequence Information (from Example 2 Above)

The Leader sequence is underlined; the CDR sequences are in bold; and the Framework sequence are neither underlined nor in bold.

```
mAb 1B5: Heavy chain variable region, DNA
FR1-CDR1-FR2-CDR2-FR3-CDR3-FR4
                                                    (SEQ ID NO: 43)
cagatccagttggtacagtctggacctgaactgaagaagcctggagagacagtcaagatctcc tgcaaggcttctgggtataccttcacaacctatggaatgagctgggtgaaacaggctccagga aagggtttaaagtggatgggctggattaatatctactctggaatcccaacatatgctgatgac ttcaagggacggtttgccttctctttggaaacctctgccagcactgcctatttgcagatcgac aacctcaaaaatgaggacacggctacatatttctgtgcaagatttgatggtcccgactactgg ggccaaggcaccactctcaccgtctcccca mAb 1B5: Heavy chain variable region, protein
FR1-CDR1-FR2-CDR2-FR3-CDR3-FR4
                                                    (SEQ ID NO: 44)
QIQLVQSGPELKKPGETVKISCKASGYTFTTYGMSWVKQAPGKGLKWMGWINIYSGIPTYADD

FKGRFAFSLETSASTAYLQIDNLKNEDTATYFCARFDGPDYWGQGTTLTVSP

Gln Ile Gln Leu Val Gln Ser Gly Pro Glu Leu Lys Lys Pro Gly Glu

Thr Val Lys Ile Ser Cys Lys Ala Ser Gly Tyr Thr Phe Thr Thr Tyr

Gly Met Ser Trp Val Lys Gln Ala Pro Gly Lys Gly Leu Lys Trp Met

Gly Trp Ile Asn Ile Tyr Ser Gly Ile Pro Thr Tyr Ala Asp Phe

Lys Gly Arg Phe Ala Phe Ser Leu Glu Thr Ser Ala Ser Thr Ala

Tyr Leu Gln Ile Asp Asn Leu Lys Asn Glu Asp Thr Ala Thr Tyr Phe

Cys Ala Arg Phe Asp Gly Pro Asp Tyr Trp Gly Gln Gly Thr Thr Leu

Thr Val Ser Pro mAb 1B5: Light chain variable region, DNA
FR1-CDR1-FR2-CDR2-FR3-CDR3-FR4
                                                    (SEQ ID NO: 45)
gacattgtgatgacacagtctccatcctccctggctatgtcagtaggacagaaggtcactatg agctgcaagtccagtcagagccttttaaatagtgtcaatcaaaagaactatttggcctggtac cagcagaaaccaggacagtctcctaaagttctggtatactttgcatccactagggtatctggg gtccctgatcgcttcataggcagtggatctgggacagatttcactcttaccatcaccagtgtg caggctgaagacctgacaacttacctctgtcagcaatattttagcactcctctcacgttcggt gctgggaccaagctggaaataaaa
``` mAb 1B5: Light chain variable region, protein
FR1-CDR1-FR2-CDR2-FR3-CDR3-FR4

(SEQ ID NO: 46)

DIVMTQSPSSLAMSVGQKVTMSCKSSQSLLNSVNQKNYLAWYQQKPGQSPKVLVYFASTRVSG

VPDRFIGSGSGTDFTLTITSVQAEDLTTYLCQQYFSTPLTFGAGTKLEIK

Asp Ile Val Met Thr Gln Ser Pro Ser Ser Leu Ala Met Ser Val Gly

Gln Lys Val Thr Met Ser Cys Lys Ser Ser Gln Ser Leu Leu Asn Ser

Val Asn Gln Lys Asn Tyr Leu Ala Trp Tyr Gln Gln Lys Pro Gly Gln

Ser Pro Lys Val Leu Val Tyr Phe Ala Ser Thr Arg Val Ser Gly Val

Pro Asp Arg Phe Ile Gly Ser Gly Ser Gly Thr Asp Phe Thr Leu Thr

Ile Thr Ser Val Gln Ala Glu Asp Leu Thr Thr Tyr Leu Cys Gln Gln

Tyr Phe Ser Thr Pro Leu Thr Phe Gly Ala Gly Thr Lys Leu Glu Ile

Lys mAb 2G9: Heavy chain variable region, DNA
Leader sequence-FR1-CDR1-FR2-CDR2-FR3-CDR3-FR4

(SEQ ID NO: 47)

<u>atgggattcagcaggatctttctcttcctcctgtcagtaactacaggtgtccactccc</u>aggct tatctacagcagtctggggctgagctggtgaggcctggggcctcagtgaagatctcctgcaag gcttctggctacacatttaccagatacaatatgcactgggtaaagcagacacctagacagggc ctggaatggattggaactatttatcccggatatggtgatacttcttacaatcagaaattcaag ggcaaggccacactgactgtagacatatcctccagcacagcctacatgcagctcaccagcctg acatctgaggactctgcggtctatttctgttcaagggagtttgccgatgattaccccattccc ccctttgactactggggccaaggcaccactctcacagtctcctca mAb 2G9: Heavy chain variable region, protein
Leader sequence-FR1-CDR1-FR2-CDR2-FR3-CDR3-FR4

(SEQ ID NO: 48)

<u>MGFSRIFLFLLSVTTGVHS</u>QAYLQQSGAELVRPGASVKISCKASGYTFTRYNMHWVKQTPRQG

LEWIGTIYPGYGDTSYNQKFKGKATLTVDISSSTAYMQLTSLTSEDSAVYFCSREFADDYPIP

PFDYWGQGTTLTVSS

<u>Met Gly Phe Ser Arg Ile Phe Leu Phe Leu Leu Ser Val Thr Thr Gly</u>

<u>Val His Ser</u> Gln Ala Tyr Leu Gln Gln Ser Gly Ala Glu Leu Val Arg

Pro Gly Ala Ser Val Lys Ile Ser Cys Lys Ala Ser Gly Tyr Thr Phe

Thr Arg Tyr Asn Met His Trp Val Lys Gln Thr Pro Arg Gln Gly Leu

Glu Trp Ile Gly Thr Ile Tyr Pro Gly Tyr Gly Asp Thr Ser Tyr Asn

Gln Lys Phe Lys Gly Lys Ala Thr Leu Thr Val Asp Ile Ser Ser Ser

Thr Ala Tyr Met Gln Leu Thr Ser Leu Thr Ser Glu Asp Ser Ala Val

Tyr Phe Cys Ser Arg Glu Phe Ala Asp Asp Tyr Pro Ile Pro Pro Phe

Asp Tyr Trp Gly Gln Gly Thr Thr Leu Thr Val Ser Ser mAb 2G9: Light chain variable region, DNA
Leader sequence-FR1-CDR1-FR2-CDR2-FR3-CDR3-FR4

(SEQ ID NO: 49)

atgaagttgcctgttaggctgttggtgctgatgttctggattcctgcttccagcagtgatgtt ttgatgacccaaactccactctccctgcctgtcagtcttggagatcaagcctccatctcttgt agatctagtcagaacattgtacatagtaatggaaacacctacttagaatggtacctgcagaaa ccaggccagtctccaaagctcctgatctacaaagtttccaaccgattttctggggtcccagac aggttcagtggcagtggatcagggacagatttcacactcaagatcagcagagtggaggctgag -continued gatctgggaatttattactgctttcaaggttcacatgttccgtacacgttcggagggggacc aagctggaaataaaa mAb 2G9: Light chain variable region, protein
Leader sequence-FR1-CDR1-FR2-CDR2-FR3-CDR3-FR4

(SEQ ID NO: 50)

<u>MKLPVRLLVLMFWIPASSS</u>DVLMTQTPLSLPVSLGDQASISCRSSQNIVHSNGNTYLEWYLQK

PGQSPKLLIYKVSNRFSGVPDRFSGSGSGTDFTLKISRVEAEDLGIYYCFQGSHVPYTFGGGT

KLEIK

<u>Met Lys Leu Pro Val Arg Leu Leu Val Leu Met Phe Trp Ile Pro Ala</u>

<u>Ser Ser Ser</u> Asp Val Leu Met Thr Gln Thr Pro Leu Ser Leu Pro Val

Ser Leu Gly Asp Gln Ala Ser Ile Ser Cys Arg Ser Ser Gln Asn Ile

Val His Ser Asn Gly Asn Thr Tyr Leu Glu Trp Tyr Leu Gln Lys Pro

Gly Gln Ser Pro Lys Leu Leu Ile Tyr Lys Val Ser Asn Arg Phe Ser

Gly Val Pro Asp Arg Phe Ser Gly Ser Gly Ser Gly Thr Asp Phe Thr

Leu Lys Ile Ser Arg Val Glu Ala Glu Asp Leu Gly Ile Tyr Tyr Cys

Phe Gln Gly Ser His Val Pro Tyr Thr Phe Gly Gly Gly Thr Lys Leu

Glu Ile Lys mAb 2H9: Heavy chain variable region, DNA
Leader sequence-FR1-CDR1-FR2-CDR2-FR3-CDR3-FR4

(SEQ ID NO: 51)

<u>atgaaattcagctgggtcatcttcttcctgatggcagtggttacaggggtcaattca</u>gaggtt cagctgcagcagtctgtggcagagcttgtgaggccagggggcctcagtcaagttgtcctgcaca gcttctggcttcaacattaaaaacacctatatgcactggataaaacagaggcctgaacagggc ctggagtggattggaaggattgctcctgcgaatgttgatactaaatatgccccgaagttccag ggcaaggccactataactgcagacacatcctccaacacagcctacatgcagctcagcaccctg acatcggaggacactgccatctattactgtgtcctgatctactatgattacgacggggacatc gatgtctggggcacagggaccacggtcaccgtctcctca mAb 2H9: Heavy chain variable region, protein
Leader sequence-FR1-CDR1-FR2-CDR2-FR3-CDR3-FR4

(SEQ ID NO: 52)

<u>MKFSWVIFFLMAVVTGVNS</u>EVQLQQSVAELVRPGASVKLSCTASGFNIKNTYMHWIKQRPEQG

LEWIGRIAPANVDTKYAPKFQGKATITADTSSNTAYMQLSTLTSEDTAIYYCVLIYYDYDGDI

DVWGTGTTVTVSS

<u>Met Lys Phe Ser Trp Val Ile Phe Phe Leu Met Ala Val Val Thr Gly</u>

<u>Val Asn Ser</u> Glu Val Gln Leu Gln Gln Ser Val Ala Glu Leu Val Arg

Pro Gly Ala Ser Val Lys Leu Ser Cys Thr Ala Ser Gly Phe Asn Ile

Lys Asn Thr Tyr Met His Trp Ile Lys Gln Arg Pro Glu Gln Gly Leu

Glu Trp Ile Gly Arg Ile Ala Pro Ala Asn Val Asp Thr Lys Tyr Ala

Pro Lys Phe Gln Gly Lys Ala Thr Ile Thr Ala Asp Thr Ser Ser Asn

Thr Ala Tyr Met Gln Leu Ser Thr Leu Thr Ser Glu Asp Thr Ala Ile

Tyr Tyr Cys Val Leu Ile Tyr Tyr Asp Tyr Asp Gly Asp Ile Asp Val

Trp Gly Thr Gly Thr Thr Val Thr Val Ser Ser mAb 2H9: Light chain variable region, DNA
Leader sequence-FR1-CDR1-FR2-CDR2-FR3-CDR3-FR4

(SEQ ID NO: 53)

<u>atgagggtccttgctgagctcctggggctgctgctgttctgcttttt</u>aggtgtgagatgtgac atccagatgaaccagtctctccatccagtctgtctgcatcccttggagacacaattaccatcact -continued

```
tgccatgccagtcagaacattaatgtttggttaagttggtaccagcagagaccaggaaatatt cctaaactattgatctataaggcttctcacttacacacaggcgtcccatcaaggtttagtggc agtggatctggaacaggtttcacattaaccatcagcagcctgcagcctgaagacattgccact tactactgtcaacagggtcaaagttggccgctcacgttcggtgctgggaccaaactggagctg aaa
``` mAb 2H9: Light chain variable region, protein
Leader sequence-FR1-CDR1-FR2-CDR2-FR3-CDR3-FR4
(SEQ ID NO: 54)

<u>MRVLAELLGLLLFCFLGVRC</u>DIQMNQSPSSLSASLGDTITITCHASQNINVWLSWYQQRPGNI

PKLLIYKASHLHTGVPSRFSGSGSGTGFTLTISSLQPEDIATYYCQQGQSWPLTFGAGTKLEL

K

<u>Met Arg Val Leu Ala Glu Leu Leu Gly Leu Leu Leu Phe Cys Phe Leu</u>

<u>Gly Val Arg Cys</u> Asp Ile Gln Met Asn Gln Ser Pro Ser Ser Leu Ser

Ala Ser Leu Gly Asp Thr Ile Thr Ile Thr Cys His Ala Ser Gln Asn

Ile Asn Val Trp Leu Ser Trp Tyr Gln Gln Arg Pro Gly Asn Ile Pro

Lys Leu Leu Ile Tyr Lys Ala Ser His Leu His Thr Gly Val Pro Ser

Arg Phe Ser Gly Ser Gly Ser Gly Thr Gly Phe Thr Leu Thr Ile Ser

Ser Leu Gln Pro Glu Asp Ile Ala Thr Tyr Tyr Cys Gln Gln Gly Gln

Ser Trp Pro Leu Thr Phe Gly Ala Gly Thr Lys Leu Glu Leu Lys mAb 3B6: Heavy chain variable region, DNA
Leader sequence-FR1-CDR1-FR2-CDR2-FR3-CDR3-FR4
(SEQ ID NO: 55)

```
atgggttggctgtggaacttgctattcctgatggcagctgcccaaagtgcccaaacacagatc cagttggtacagtctggacctgaactgaagaagcctggagagacagtcaagatctcctgcaag gcttctgggtataccttcacaacctatggaatgagctgggtgaaacaggctccaggaaaggt ttaaagtggatgggctggattaatatctactctggaatcccaacatatgctgatgacttcaag ggacgatttgccttctcttggaaaccctctgccagcactgcctatttgcagatcgacaacctc aaaaatgaggacacggctacatatttctgtgcaagatttgatggtcccgactactggggccaa ggcaccactctcacagtctcctca
``` mAb 3B6: Heavy chain variable region, protein
(SEQ ID NO: 56)

<u>MGWLWNLLFLMAAAQSAQT</u>QIQLVQSGPELKKPGETVKISCKASGYTFTTYGMSWVKQAPGKG

LKWMGWINIYSGIPTYADDFKGRFAFSLETSASTAYLQIDNLKNEDTATYFCARFDGPDYWGQ

GTTLTVSS

<u>Met Gly Trp Leu Trp Asn Leu Leu Phe Leu Met Ala Ala Ala Gln Ser</u>

<u>Ala Gln Thr</u> Gln Ile Gln Leu Val Gln Ser Gly Pro Glu Leu Lys Lys

Pro Gly Glu Thr Val Lys Ile Ser Cys Lys Ala Ser Gly Tyr Thr Phe

Thr Thr Tyr Gly Met Ser Trp Val Lys Gln Ala Pro Gly Lys Gly Leu

Lys Trp Met Gly Trp Ile Asn Ile Tyr Ser Gly Ile Pro Thr Tyr Ala

Asp Asp Phe Lys Gly Arg Phe Ala Phe Ser Leu Glu Thr Ser Ala Ser

Thr Ala Tyr Leu Gln Ile Asp Asn Leu Lys Asn Glu Asp Thr Ala Thr

Tyr Phe Cys Ala Arg Phe Asp Gly Pro Asp Tyr Trp Gly Gln Gly Thr

Thr Leu Thr Val Ser Ser mAb 3B6: Light chain variable region, DNA
Leader sequence-FR1-CDR1-FR2-CDR2-FR3-CDR3-FR4

-continued (SEQ ID NO: 57)
<u>atggaatcacagacccaggtcctcatgtttcttctgctctgggtatctggtgcctgtgcagac</u> attgtgatgacacagtctccatcctccctggctgtgtcagtaggacggaaggtcactatgagc tgcaagtccagtcagagccttttaaatagtgtcaatcaaaagaactatttggcctggtaccag cagaaaccaggacagtctcctaaagttctggtatactttgcatccgctagggtatctggggtc cctgatcgcttcataggcagtggatctgggacagatttcactcttgccatcagcagtgtgcag gctgaagacctgacaacttacttctgtcagcaatattttagcactcctctcacgttcggtgct gggaccaagctggaactgaaa mAb 3B6: Light chain variable region, protein
Leader sequence-FR1-CDR1-FR2-CDR2-FR3-CDR3-FR4

(SEQ ID NO: 58)
<u>MESQTQVLMFLLLWVSGACAD</u>IVMTQSPSSLAVSVGRKVTMSCKSSQSLLNSVNQKNYLAWYQ

QKPGQSPKVLVYFASARVSGVPDRFIGSGSGTDFTLAISSVQAEDLTTYFCQQYFSTPLTFGA

GTKLELK

<u>Met Glu Ser Gln Thr Gln Val Leu Met Phe Leu Leu Leu Trp Val Ser</u>

<u>Gly Ala Cys Ala</u> Asp Ile Val Met Thr Gln Ser Pro Ser Ser Leu Ala

Val Ser Val Gly Arg Lys Val Thr Met Ser Cys Lys Ser Ser Gln Ser

Leu Leu Asn Ser Val Asn Gln Lys Asn Tyr Leu Ala Trp Tyr Gln Gln

Lys Pro Gly Gln Ser Pro Lys Val Leu Val Tyr Phe Ala Ser Ala Arg

Val Ser Gly Val Pro Asp Arg Phe Ile Gly Ser Gly Ser Gly Thr Asp

Phe Thr Leu Ala Ile Ser Ser Val Gln Ala Glu Asp Leu Thr Thr Tyr

Phe Cys Gln Gln Tyr Phe Ser Thr Pro Leu Thr Phe Gly Ala Gly Thr

Lys Leu Glu Leu Lys mAb 4D12: Heavy chain variable region, DNA
Leader sequence-FR1-CDR1-FR2-CDR2-FR3-CDR3-FR4

(SEQ ID NO: 59)
<u>atgggttggctgtggaacttgctattcctgatggcagctgcccaaagtgcccaagca</u>cagatc cagttggtacagtctggacctgaactgaagaagcctggagagacagtcaagatctcctgcaag gcttctgggtataccttcacaacctatggaatgagctgggtgaaacaggcgccaggaaagggt ttaaagtggatgggctggataaatatctactctggaatgccaacatatgctgatgacttcaag ggacggtttgccttctctttggaaacctctgtcagcactgcctatttgcagatcaacaacctc aaaaatgaggacacggctacatatttctgtgcaagatttgatggtcccgactactggggccaa ggcaccactctcacagtctcctca mAb 4D12: Heavy chain variable region, protein
Leader sequence-FR1-CDR1-FR2-CDR2-FR3-CDR3-FR4

(SEQ ID NO: 60)
<u>MGWLWNLLFLMAAAQSAQA</u>QIQLVQSGPELKKPGETVKISCKASGYTFTTYGMSWVKQAPGKG

LKWMGWINIYSGMPTYADDFKGRFAFSLETSVSTAYLQINNLKNEDTATYFCARFDGPDYWGQ

GTTLTVSS

<u>Met Gly Trp Leu Trp Asn Leu Leu Phe Leu Met Ala Ala Ala Gln Ser</u>

<u>Ala Gln Ala</u> Gln Ile Gln Leu Val Gln Ser Gly Pro Glu Leu Lys Lys

Pro Gly Glu Thr Val Lys Ile Ser Cys Lys Ala Ser Gly Tyr Thr

Phe Thr Thr Tyr Gly Met Ser Trp Val Lys Gln Ala Pro Gly Lys

Gly Leu Lys Trp Met Gly Trp Ile Asn Ile Tyr Ser Gly Met Pro Thr

Tyr Ala Asp Asp Phe Lys Gly Arg Phe Ala Phe Ser Leu Glu Thr

Ser Val Ser Thr Ala Tyr Leu Gln Ile Asn Asn Leu Lys Asn Glu Asp

Thr Ala Thr Tyr Phe Cys Ala Arg Phe Asp Gly Pro Asp Tyr Trp Gly

Gln Gly Thr Thr Leu Thr Val Ser Ser mAb 4D12: Light chain variable region, DNA
Leader sequence-FR1-CDR1-FR2-CDR2-FR3-CDR3-FR4

(SEQ ID NO: 61)

<u>atggaatcacagacccaggtcctcatgtttcttctgctctgggtatctggtgcctgtgcagac</u> attgtgatgacacagtctccatcctccctggctatgtcagtaggacagaaggtcactatgagc tgcaagtccagtcagagccttttaaatagtgtcaatcaaaagaactatttggcctggtaccag cagaaaccaggacagtctcctaaagttctggtatactttgcatccactaggatatctggggtc cctgatcgcttcataggcagtggatctgggacagatttcactcttaccatcagcagtgtgcag gctgaagacctggcagattacttctgtcagcaatattttagcactcctctcacgttcggtgct gggaccaagctggagctgaaa mAb 4D12: Light chain variable region, protein
Leader sequence-FR1-CDR1-FR2-CDR2-FR3-CDR3-FR4

(SEQ ID NO: 62)

<u>MESQTQVLMFLLLWVSGACAD</u>IVMTQSPSSLAMSVGQKVTMSCKSSQSLLNSVNQKNYLAWYQ

QKPGQSPKVLVYFASTRISGVPDRFIGSGSGTDFTLTISSVQAEDLADYFCQQYFSTPLTFGA

GTKLELK

<u>Met Glu Ser Gln Thr Gln Val Leu Met Phe Leu Leu Leu Trp Val Ser</u>

<u>Gly Ala Cys Ala</u> Asp Ile Val Met Thr Gln Ser Pro Ser Ser Leu Ala

Met Ser Val Gly Gln Lys Val Thr Met Ser Cys Lys Ser Ser Gln Ser

Leu Leu Asn Ser Val Asn Gln Lys Asn Tyr Leu Ala Trp Tyr Gln Gln

Lys Pro Gly Gln Ser Pro Lys Val Leu Val Tyr Phe Ala Ser Thr Arg

Ile Ser Gly Val Pro Asp Arg Phe Ile Gly Ser Gly Ser Gly Thr Asp

Phe Thr Leu Thr Ile Ser Ser Val Gln Ala Glu Asp Leu Ala Asp Tyr

Phe Cys Gln Gln Tyr Phe Ser Thr Pro Leu Thr Phe Gly Ala Gly Thr

Lys Leu Glu Leu Lys mAb 5G5: Heavy chain variable region, DNA
Leader sequence-FR1-CDR1-FR2-CDR2-FR3-CDR3-FR4

(SEQ ID NO: 63)

<u>atgaaattcagctgggtcatcttcttcctgatggcagtggttacaggggtcaattcagaggtt</u> cagctgcagcagtctgtggcagagcttgtgaggccaggggcctcagtcaagttgtcctgcaca gtttctggcttcaacattaaaaacacctatatgcactgggtgaagcagaggcctgaacagggc ctggagtggattggaagaattgatcctgcgaatgttaatactaaatatgccccgaagttccag ggcaaggccactataactacagacacatcctccaacacagcctacatgcagctcagcagcctg acatcggaggacactgccatctattactgtgtcctgattttctatgattacgacggggacatc gatgtctggggcacagggaccaaggtcaccgtctcctca mAb 5G5: Heavy chain variable region, protein
Leader sequence-FR1-CDR1-FR2-CDR2-FR3-CDR3-FR4

(SEQ ID NO: 64)

<u>MKFSWVIFFLMAVVTGVNS</u>EVQLQQSVAELVRPGASVKLSCTVSGFNIKNTYMHWVKQRPEQG

LEWIGRIDPANVNTKYAPKFQGKATITTDTSSNTAYMQLSSLTSEDTAIYYCVLIFYDYDGDI

DVWGTGTKVTVSS

<u>Met Lys Phe Ser Trp Val Ile Phe Phe Leu Met Ala Val Val Thr Gly</u>

<u>Val Asn Ser</u> Glu Val Gln Leu Gln Gln Ser Val Ala Glu Leu Val Arg

Pro Gly Ala Ser Val Lys Leu Ser Cys Thr Val Ser Gly Phe Asn Ile

-continued

Lys Asn Thr Tyr Met His Trp Val Lys Gln Arg Pro Glu Gln Gly Leu
Glu Trp Ile Gly **Arg Ile Asp Pro Ala Asn Val Asn Thr Lys Tyr Ala
Pro Lys Phe Gln Gly** Lys Ala Thr Ile Thr Thr Asp Thr Ser Ser Asn
Thr Ala Tyr Met Gln Leu Ser Ser Leu Thr Ser Glu Asp Thr Ala Ile
Tyr Tyr Cys Val Leu Ile Phe Tyr Asp Tyr Asp Gly Asp Ile Asp Val
Trp Gly Thr Gly Thr Lys Val Thr Val Ser Ser mAb 5G5: Light chain variable region, DNA
Leader sequence-FR1-CDR1-FR2-CDR2-FR3-CDR3-FR4

(SEQ ID NO: 65)

<u>atgaqggtccttgctgagctcctggggctgctgctgttctgc</u>ttttaggtgtgagatgtgac atccagatgaaccagtctccatccagtctgtctgcatcccttggagacacaattaccatcact tgccatgccagtcagaacattaatgtttggttaagctggtaccagcagaaaccaggaaatatt cctaaactattgatctataaggcttccaacttacacacaggcgtcccatcaaggtttagtggc agtggatctggaacagatttcacattaaccatcagcagcctgcagcctgaagacattgccact tactactgtcaacagggtcaaagttatccgctcacgttcggtgctgggaccaagctggagctg aaa mAb 5G5: Light chain variable region, protein
Leader sequence-FR1-CDR1-FR2-CDR2-FR3-CDR3-FR4

(SEQ ID NO: 66)

<u>MRVLAELLGLLLLFC</u>FLGVRCDIQMNQSPSSLSASLGDTITITCHASQNINVWLSWYQQKPGNI

PKLLIYKASNLHTGVPSRFSGSGSGTDFTLTISSLQPEDIATYYCQQGQSYPLTFGAGTKLEL

K

<u>Met Arg Val Leu Ala Glu Leu Leu Gly Leu Leu Leu Phe Cys</u> Phe Leu
Gly Val Arg Cys Asp Ile Gln Met Asn Gln Ser Pro Ser Ser Leu Ser
Ala Ser Leu Gly Asp Thr Ile Thr Ile Thr Cys **His Ala Ser Gln Asn
Ile Asn Val Trp Leu Ser** Trp Tyr Gln Lys Pro Gly Asn Ile Pro
Lys Leu Leu Ile Tyr Lys Ala Ser Asn Leu His Thr Gly Val Pro Ser
Arg Phe Ser Gly Ser Gly Ser Gly Thr Asp Phe Thr Leu Thr Ile Ser
Ser Leu Gln Pro Glu Asp Ile Ala Thr Tyr Tyr Cys **Gln Gln Gly Gln
Ser Tyr Pro Leu Thr** Phe Gly Ala Gly Thr Lys Leu Glu Leu Lys mAb 7C9: Heavy chain variable region, DNA
FR1-CDR1-FR2-CDR2-FR3-CDR3-FR4

(SEQ ID NO: 67)

caggtgcagctgaagcagtcaggacctggcctagtgcagccctcacagagcctgtccataacc tgcacagtctctggtttctcattaactagctatggtgtacactgggttcgccagtctccagga aagggtttaaagtggatgggctggattaatatctactctggaatcccaacatatgctgatgac ttcaagggacggttttgccttctctttggaaacctctgccagcactgcctatttgcagatcgac aacctcaaaaatgaggacacggctacatatttctgtgcaagatttgatggtcccgactactgg ggccaaggcatcactctcactgtctccgca mAb 7C9: Heavy chain variable region, protein
FR1-CDR1-FR2-CDR2-FR3-CDR3-FR4

(SEQ ID NO: 68)

QVQLKQSGPGLVQPSQSLSITCTVSGFSLTSYGVHWVRQSPGKGLKWMG**WINIYSGIPTYADD

FKGRFAFSLETSASTAYLQIDNLKNEDTATYFCARFDGPDY**WGQGITLTVSA

Gln Val Gln Leu Lys Gln Ser Gly Pro Gly Leu Val Gln Pro Ser Gln
Ser Leu Ser Ile Thr Cys Thr Val Ser **Gly Phe Ser Leu Thr Ser Tyr
Gly Val His** Trp Val Arg Gln Ser Pro Gly Lys Gly Leu Lys Trp Met

```
Gly Trp Ile Asn Ile Tyr Ser Gly Ile Pro Thr Tyr Ala Asp Asp Phe

Lys Gly Arg Phe Ala Phe Ser Leu Glu Thr Ser Ala Ser Thr Ala Tyr

Leu Gln Ile Asp Asn Leu Lys Asn Glu Asp Thr Ala Thr Tyr Phe Cys

Ala Arg Phe Asp Gly Pro Asp Tyr Trp Gly Gln Gly Ile Thr Leu Thr

Val Ser Ala
``` mAb 7C9: Light chain variable region, DNA
FR1-CDR1-FR2-CDR2-FR3-CDR3-FR4
(SEQ ID NO: 69)

```
gacattgtgatgacacagtctccatcctccctggctatgtcagtaggacagaaggtcactatg agctgcaagtccagtcagagccttttaaatagtgtcaatcaaaagaactatttggcctggtac cagcagaaaccaggacagtctcctaaagttctggtatactttgcatccactagggtatctggg gtccctgatcgcttcataggcagtggatctgggacagatttcactcttaccatcaccagtgtg caggctgaagacctgacaacttacttctgtcagcaatattttagcactcctctcacgttcggt gctgggaccaagctggaactgaaa
``` mAb 7C9: Light chain variable region, protein
FR1-CDR1-FR2-CDR2-FR3-CDR3-FR4
(SEQ ID NO: 70)

```
DIVMTQSPSSLAMSVGQKVTMSCKSSQSLLNSVNQKNYLAWYQQKPGQSPKVLVYFASTRVSG

VPDRFIGSGSGTDFTLTITSVQAEDLTTYFCQQYFSTPLTFGAGTKLELK

Asp Ile Val Met Thr Gln Ser Pro Ser Ser Leu Ala Met Ser Val Gly

Gln Lys Val Thr Met Ser Cys Lys Ser Ser Gln Ser Leu Leu Asn Ser

Val Asn Gln Lys Asn Tyr Leu Ala Trp Tyr Gln Gln Lys Pro Gly Gln

Ser Pro Lys Val Leu Val Tyr Phe Ala Ser Thr Arg Val Ser Gly Val

Pro Asp Arg Phe Ile Gly Ser Gly Ser Gly Thr Asp Phe Thr Leu Thr

Ile Thr Ser Val Gln Ala Glu Asp Leu Thr Thr Tyr Phe Cys Gln Gln

Tyr Phe Ser Thr Pro Leu Thr Phe Gly Ala Gly Thr Lys Leu Glu Leu

Lys
``` mAb 1E4: Heavy chain variable region, DNA
Leader sequence-FR1-CDR1-FR2-CDR2-FR3-CDR3-FR4
(SEQ ID NO: 109)

```
atgggattcagcaggatctttctcttcctcctgtcagtaactacaggtgtccactcccaggct tatctacagcagtctggggctgagctggtgaggcctggggcctcagtgaagatgtcctgcaag gcttttggctacacatttaccagttacaatatgcactgggtgaagcagacacctagacaggc ctggaatggattggaaccatttatccaggagatggtgacgcttcctacaatcagaaattccag gacaaggccacactgactgttgacaaatcctccagcacagcctacatgcagctcagcagcctg acatctgaagactctgcggtctatttctgttcaagggagtttgccgatgcttacccattccc ccctttgactactggggccaaggcaccactctcacagtctcctca
``` mAb 1E4: Heavy chain variable region, protein
Leader sequence-FR1-CDR1-FR2-CDR2-FR3-CDR3-FR4
(SEQ ID NO: 110)

```
MGFSRIFLFLLSVTTGVHSQAYLQQSGAELVRPGASVKMSCKAFGYTFTSYNMHWVKQTPRQG

LEWIGTIYPGDGDASYNQKFQDKATLTVDKSSSTAYMQLSSLTSEDSAVYFCSREFADAYPIP

PFDYWGQGTTLTVSS
``` mAb 1E4: Light chain variable region, DNA
Leader sequence-FR1-CDR1-FR2-CDR2-FR3-CDR3-FR4
(SEQ ID NO: 111)

```
atgaagttgcctgttaggctgttggtgctgatttctggattcctgcttccagtagtgatgtt ttgatgacccaaactccactctccctggttgtcagtcttggagatcaggcctccatctcttgc
```

-continued

```
agatctagtcagagcattgtatatagtaatggaaacacctatttagaatggtacctgcaaaaa ccaggccagtctccaaagctcctgatttacaaagtttccaaccgattttctggggtcccagac aggttcagtggcagtggatcagggacagatttcacactcaagatcagcagagtggaggctgag gatctgggagtttattactgctttcaaggttcacatgttccgtacacgttcggaggggggacc aagctggaaataaaa
``` mAb 1E4: Light chain variable region, protein
Leader sequence-FR1-CDR1-FR2-CDR2-FR3-CDR3-FR4

(SEQ ID NO: 112)

MKLPVRLLVLIFWIPASSSDVLMTQTPLSLVVSLGDQASISCRSSQSIVYSNGNTYLEWYLQK

PGQSPKLLIYKVSNRFSGVPDRFSGSGSGTDFTLKISRVEAEDLGVYYCFQGSHVPYTFGGGT

KLEIK

Example 5

Epitope Mapping of Anti-Canine PD-1 Antibodies

Introduction

The interaction of antibodies with their cognate protein antigens is mediated through the binding of specific amino acids (paratopes) of the antibodies with specific amino acids (epitopes) of target antigens. An epitope is an antigenic determinant that causes a specific reaction by an immunoglobulin. It consists of a group of amino acids on the surface of the antigen. A protein of interest may contain several epitopes that are recognized by different antibodies. The epitopes recognized by antibodies are classified as linear or conformational epitopes. Linear epitopes are formed by a stretch of continuous sequence of amino acids in a protein, while conformational epitopes are composed of amino acids that are discontinuous (e.g, far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs and help elucidate their mechanisms of action. Epitope information can also elucidate unique cancer epitopes and define the protective or pathogenic effects of vaccines.

Epitope mapping can be carried out using polyclonal or monoclonal antibodies and several methods are employed for epitope identification depending on the suspected nature of the epitope (i.e., linear versus conformational). Mapping linear epitopes is more straightforward and relatively easy to perform. For this purpose, commercial services for linear epitope mapping often employ peptide scanning. In this case, an overlapping set of short peptide sequences of the target protein are chemically synthesized and tested for their ability to bind antibodies of interest. The strategy is rapid, high-throughput, and relatively inexpensive to perform. On the other hand, mapping of discontinuous epitope is more technically challenging and requires more specialized techniques such as x-ray co-crystallography of a monoclonal antibody together with its target protein, Hydrogen-Deuterium (H/D) exchange, and/or Mass Spectroscopy coupled with enzymatic digestion.

Mapping of PD-1 Epitopes Using a ProImmune® MicroArray:

In order to identify the amino acids that form the epitopes for anti-PD1 mAbs, a total of 28 peptides that are 15 amino acids long and overlapping by 10 amino acids were chemically synthesized. This library of overlapping peptides was designed to cover the full length canine PD-1 protein. The sequences of these peptides are listed in Table 6 below. The determination of peptide-antibody binding was performed by attachment of antibody samples to the ProArray Ultra® peptide microarray, followed by incubation with a fluorescent-labelled secondary antibody. All peptides are synthesized separately, and then bound to the ProArray Ultra® slide surface alongside ProImmune® murine IgG controls. This optimized process ensures that peptides are presented on the array in such a manner as to closely mimic the properties of the corresponding protein region, circumventing the inherent physiochemical variation of the free peptides themselves and making a compatible, combined peptide and protein array platform. The test analytes (peptides) are dispensed onto the ProArray Ultra® slide in discrete spots and appropriate gal-files enable exact alignment of the resulting array features back to the analyte deposited. ProArray Ultra® slides were blocked using a validated blocking buffer to reduce non-specific binding of the mAbs. They were then incubated with the mAb samples, followed by incubation with a specific fluorescent-labelled secondary antibody. After several washing steps, the ProArray Ultra® arrays were dried and scanned using a high-resolution fluorescence microarray scanning system. After scanning the fluorescent labelled ProArray Ultra® slides, the scanner recorded an image which was evaluated using image analysis software-enabling interpretation and quantification of the levels of fluorescent intensities associated with each fluorescent spot on the scanned microarray slide. The results of this experiment indicated some of the canine PD-1 peptides were recognized by some of the mAbs evaluated. The identity of the mAbs and the amino acid sequence recognized by these mAbs are listed in Table 7. This study indicates that mAb 2H9 recognizes an epitope located in the extracellular domain of canine PD-1 comprised of the amino acid sequence represented by SEQ ID NO: 84 and that mAb 1A1 recognizes an epitope comprising the amino acid sequence represented by SEQ ID NO: 84 and the overlapping amino acid sequence represented by the amino acid sequence represented by SEQ ID NO: 83.

Mapping of PD-1 Epitopes Using Mass Spectroscopy:

In order to identify potentially discontinuous epitopes recognized by anti-canine PD-1 a method based on chemical crosslinking and mass spectrometry detection was used (CovalX® Instrument Incorporated). The application of this technology to epitope mapping of canine PD-1 resulted in identification of at least portions of epitopes recognized by the indicated mAbs which are listed in Table 8. As can be seen from Table 8, mAb 3B6 recognizes at least a portion of an epitope located in the extracellular domain of canine PD-1 within the amino acid sequence represented by SEQ ID NO: 99 and that mAb 2G9 recognizes at least a portion of an epitope within the amino acid sequence represented by SEQ ID NO: 100. On the other hand, mAb 1E4 and mAb 1B5 recognize at least a portion of an epitope within the amino acid sequence represented by SEQ ID NO: 101 and acid sequence represented by SEQ ID NO: 102, respectively.

Figure 9A:
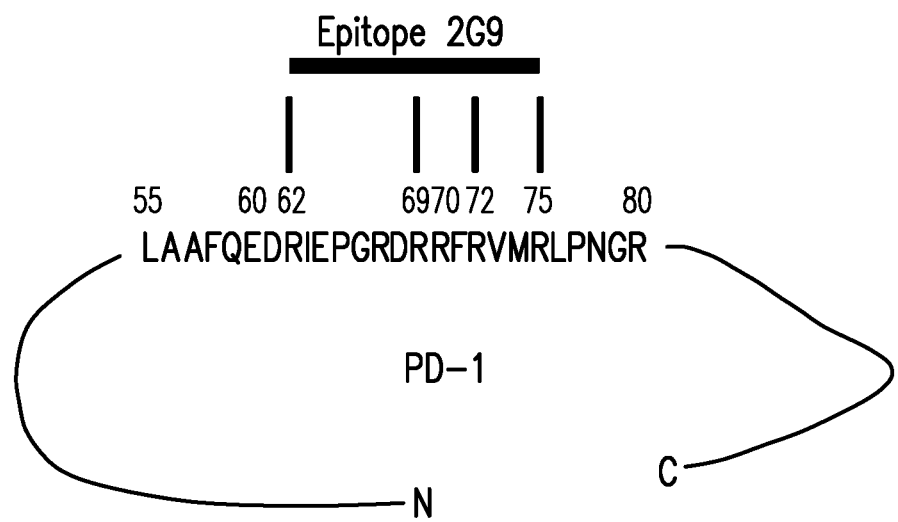
FIG. 9A shows the characterization of the interface between canine PD-1 and the caninized antibody 2G9. The amino acid positions are with respect to the PD-1 amino acid sequence without the signal sequence, i.e., SEQ ID NO: 2. The determination was performed by chemical cross-linking, High-Mass MALDI mass spectrometry and nLC-Orbitrap mass spectrometry.
Figure 9B:
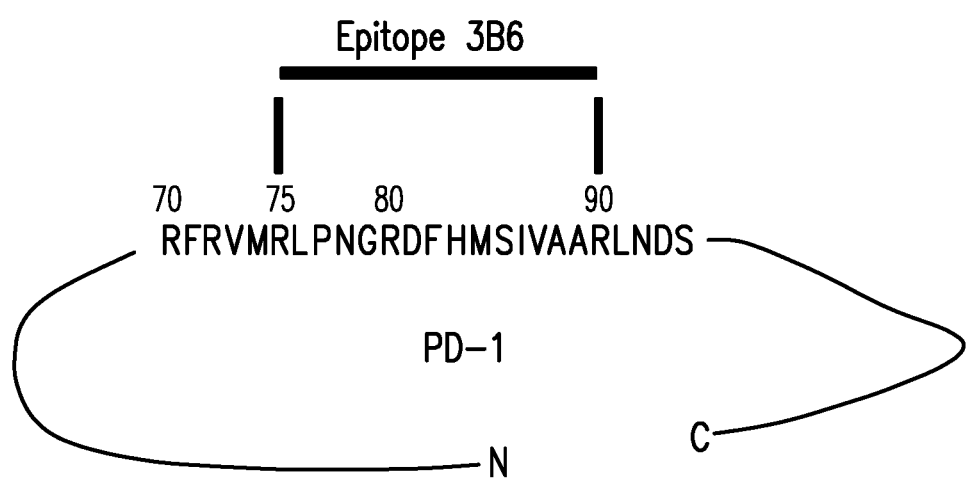
FIG. 9B shows the characterization of the interface between canine PD-1 and the caninized antibody 3B6. The amino acid positions are with respect to the PD-1 amino acid sequence without the signal sequence, i.e., SEQ ID NO: 2. The determination was performed by chemical cross-linking, High-Mass MALDI mass spectrometry and nLC-Orbitrap mass spectrometry.

As depicted in FIG. 9A a determination performed by chemical cross-linking, High-Mass MALDI mass spectrometry and nLC-Orbitrap mass spectrometry shows that the epitope on canine PD-1 recognized by caninized antibody 2G9 comprises $R_{62}$, $R_{69}$, $R_{72}$, and $R_{75}$ of SEQ ID NO: 2. The analogous determination for the epitope on canine PD-1 recognized by caninized antibody 3B6 comprises $R_{75}$ and $R_{90}$ of SEQ ID NO: 2. Accordingly, $R_{75}$ appears to be a particularly important amino acid residue in one or more epitopes of canine PD-1. Interestingly, after performing these analyses, the amino acid sequence for the CDRs of 1A1 were found to be identical to that of 2G9. The consistency between the region on PD-1 that 2G9 binds with that found for 1A1, which were obtained by these two very different methodologies, indicates that this region contains amino acid residues comprised by a PD-1 epitope that is recognized by the anti-caninine PD-1 antibodies (see, Tables 7 and 8 below).

Moreover, the region of the amino acid sequence of PD-1 that is recognized by the blocking antibodies of the present invention tested is within the extracellular domain of canine PD-1. The region recognized is comprised by the following peptide (see, Tables 7 and 8 below).

```
                                        (SEQ ID NO: 103)
NQTDKLAAFQEDRIEPGRDRRFRVM*RLPNGRDFHMSIVAARLNDS
```

Within this peptide, is a shorter peptide that is in bold. This shorter peptide was recognized with the ProImmune® MicroArray (see, Table 7).

```
DRIEPGRDRRFRVM'RLPNGR                    (SEQ ID NO:104)
```

Notably, $R_{62}$, $R_{69}$, $R_{72}$, and $R_{75}$ of SEQ ID NO: 2 are all comprised by both the longer peptide (SEQ ID NO: 103) and the shorter peptide (SEQ ID NO: 104), whereas $R_{90}$ of SEQ ID NO: 2 is in the longer peptide. These five arginine residues appear to be important amino acid residues in one or more epitopes of canine PD-1. As indicated in the Tables 6-8, the starred methionine residue (*) has also been reported as being a threonine residue.

TABLE 6

PEPTIDES USED FOR EPITOPE MAPPING BY PROIMMUNE ® MICROARRAY

| SEQ ID NO: | ANTIGEN PEPTIDE |
|---|---|
| 71 | LDSPDRPWSPLTFSP |
| 72 | RPWSPLTFSPAQLTV |
| 73 | LTFSPAQLTVQEGEN |

TABLE 6-continued

PEPTIDES USED FOR EPITOPE MAPPING BY PROIMMUNE ® MICROARRAY

| SEQ ID NO: | ANTIGEN PEPTIDE |
|---|---|
| 74 | AQLTVQEGENATFTC |
| 75 | QEGENATFTCSLADI |
| 76 | ATFTCSLADIPDSFV |
| 77 | SLADIPDSFVLNWYR |
| 78 | PDSFVLNWYRLSPRN |
| 79 | LNWYRLSPRNQTDKL |
| 80 | LSPRNQTDKLAAFQE |
| 81 | QTDKLAAFQEDRIEP |
| 82 | AAFQEDRIEPGRDRR |
| 83 | DRIEPGRDRRFRVM*R |
| 84 | GRDRRFRVM*RLPNGR |
| 85 | FRVM*RLPNGRDFHMS |
| 86 | LPNGRDFHMSIVAAR |
| 87 | DFHMSIVAARLNDSG |
| 88 | IVAARLNDSGIYLCG |
| 89 | LNDSGIYLCGAIYLP |
| 90 | IYLCGAIYLPPNTQI |
| 91 | AIYLPPNTQINESPR |
| 92 | PNTQINESPRAELSV |
| 93 | NESPRAELSVTERTL |
| 94 | AELSVTERTLEPPTQ |
| 95 | TERTLEPPTQSPSPP |
| 96 | EPPTQSPSPPPRLSG |
| 97 | SPSPPPRLSGQLQGL |
| 98 | PSPPPRLSGQLQGLV |

*This methionine residue has also been reported as being a threonine residue.

TABLE 7

PD-1 EPITOPES RECOGNIZED BY ANTI-CANINE PD-1 MAABS USING PROIMMUNE ® MICROARRAY

| ANTIBODY | ANTIGEN PEPTIDE | SEQ ID NO: |
|---|---|---|
| 2H9 | GRDRRFRVM*RLPNGR | 84 |
| 1A1# | DRIEPGRDRRFRVM*R | 83 |
| 1A1 | GRDRRFRVM*RLPNGR | 84 |

*This methionine residue has also been reported as being a threonine residue.
The CDRs of 1A1 are identical to those of 2G9.

TABLE 8

PD-1 EPITOPES RECOGNIZED BY ANTI-CANINE PD-1 MAABS USING MASS SPECTROMETRY

| ANTIBODY | PEPTIDE ANTIGEN | SEQ ID NO: |
|---|---|---|
| 3B6 | RFRVM*RLPNGRDFHMSIVAARLNDS | 99 |
| 2G9 | LAAFQEDRIEPGRDRRFRVM*RLPNGR | 100 |
| 1E4 | EDRIEPGRDRRFRVM*RLPNGRDFHMSIVAAR | 101 |
| 1B5 | NQTDKLAAFQEDRIEPGRDRRFRVM*RLPNGR | 102 |

*This methionine residue has also been reported as being a threonine residue.

TABLE 9

SEQUENCE LISTING FOR CANINE PD-1 AND PD-L1

| SEQ ID | N.A. | A.A. | Description | SEQ ID | N.A. | A.A. | Description |
|---|---|---|---|---|---|---|---|
| 1 | ✓ | | Canine PD-1 Full Length | 7 | ✓ | | Canine PD-L1 Full Length |
| 2 | | ✓ | Canine PD-1 Full Length | 8 | | ✓ | Canine PD-L1 Full Length |
| 3 | ✓ | | Canine PD-1 ECD | 9 | ✓ | | Canine PD-L1 ECD |
| 4 | | ✓ | Canine PD-1 ECD | 10 | | ✓ | Canine PD-L1 ECD |
| 5 | ✓ | | Canine PD-1 - Human IgG1 | 11 | ✓ | | Canine PD-L1 - Human IgG1 |
| 6 | | ✓ | Canine PD-1 - Human IgG1 | 12 | | ✓ | Canine PD-L1 - Human IgG1 |
| 105 | ✓ | | Full Length Canine PD-1 + signal sequence | 107 | ✓ | | Full Length Canine PD-L1 + signal sequence |
| 106 | | ✓ | Full Length Canine PD-1 + signal sequence | 108 | | ✓ | Full Length Canine PD-L1 + signal sequence |
| 113 | | ✓ | Canine PD-1 - Hum. IgG1 + sig. seq | | | | |

TABLE 10

SEQUENCE LISTING TABLE FOR CANINE IgGB MODIFICATIONS

| ID | N.A. | A.A. | Description |
|---|---|---|---|
| 39 | | ✓ | cIgGB wt |
| 40 | | ✓ | cIgGB(+)A-hinge |
| 41 | | ✓ | cIgGB(+)D-hinge |
| 42 | | ✓ | cIgGB(−)ADCC |

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

SEQUENCE LISTING

<160> NUMBER OF SEQ ID NOS: 114

<210> SEQ ID NO 1
<211> LENGTH: 795
<212> TYPE: DNA
<213> ORGANISM: Canis familiaris

<400> SEQUENCE: 1

```
ctagactccc ctgacaggcc ctggagcccg ctcaccttct ccccggcgca gctcacggtg      60
caggagggag agaacgccac gttcacctgc agcctggccg acatcccga cagcttcgtg      120 ctcaactggt accgcctgag cccccgcaac cagacggaca agctggccgc cttccaggag     180
gaccgcatcg agccgggccg ggacaggcgc ttccgcgtca tgcggctgcc caacgggcgg     240
gacttccaca tgagcatcgt cgctgcgcgc ctcaacgaca cggcatcta cctgtgcggg      300 gccatctacc tgcccccaa cacacagatc aacgagagtc ccgcgcaga gctctccgtg       360 acggagagaa ccctggagcc ccccacacag agccccagcc cccacccag actcagcggc     420 cagttgcagg ggctggtcat cggcgtcacg agcgtgctgg tgggtgtcct gctactgctg     480
ctgctgacct gggtcctggc cgctgtcttc cccaggccca cccgaggtgc ctgtgtgtgc    540
gggagcgagg acgagcctct gaaggagggc cccgatgcag cgcccgtctt caccctggac    600
tacggggagc tggacttcca gtggcgagag aagacgccgg agcccccggc gcctgtgcc     660 ccggagcaga ccgagtatgc caccatcgtc ttcccgggca ggccggcgtc cccgggccgc   720
agggcctcgg ccagcagcct gcagggagcc cagcctccga gccccgagga cggacccggc   780
ctgtggcccc tctga                                                      795
```

<210> SEQ ID NO 2
<211> LENGTH: 264
<212> TYPE: PRT
<213> ORGANISM: Canis familiaris

<400> SEQUENCE: 2

```
Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val Ile Gly Val Thr Ser Val Leu Val Gly Val Leu Leu Leu Leu
145                 150                 155                 160

Leu Leu Thr Trp Val Leu Ala Ala Val Phe Pro Arg Ala Thr Arg Gly
                165                 170                 175
```

```
Ala Cys Val Cys Gly Ser Glu Asp Glu Pro Leu Lys Glu Gly Pro Asp
            180                 185                 190

Ala Ala Pro Val Phe Thr Leu Asp Tyr Gly Glu Leu Asp Phe Gln Trp
            195                 200                 205

Arg Glu Lys Thr Pro Glu Pro Pro Ala Pro Cys Ala Pro Glu Gln Thr
    210                 215                 220

Glu Tyr Ala Thr Ile Val Phe Pro Gly Arg Pro Ala Ser Pro Gly Arg
225                 230                 235                 240

Arg Ala Ser Ala Ser Ser Leu Gln Gly Ala Gln Pro Pro Ser Pro Glu
            245                 250                 255

Asp Gly Pro Gly Leu Trp Pro Leu
            260
```

<210> SEQ ID NO 3
<211> LENGTH: 438
<212> TYPE: DNA
<213> ORGANISM: Artificial Sequence
<220> FEATURE:
<223> OTHER INFORMATION: Codon optimized

<400> SEQUENCE: 3

```
ctggattccc ccgacagacc ctggagccct ctcaccttct cccctgccca gctgaccgtc      60
caggaaggcg agaatgccac cttcacctgc agcctcgccg acatccccga cagcttcgtg     120
ctgaactggt acagactgag ccccaggaac cagaccgaca gctggccgc tttccaggag      180
gacaggatcg aacccggcag ggacaggagg tttagggtca tgaggctgcc aacggcagg     240
gacttccaca tgtccatcgt ggccgccaga ctgaacgact ccggcatcta cctgtgcggc     300
gctatctacc tgcccccaa cacccagatc aacgagagcc caggccga actgagcgtg       360
acagagagaa ccctggaacc tcccacccag agcccttccc ctcctcctag actgagcgga    420
cagctgcagg gcctggtg                                                   438
```

<210> SEQ ID NO 4
<211> LENGTH: 438
<212> TYPE: PRT
<213> ORGANISM: Canis familiaris

<400> SEQUENCE: 4

```
Cys Thr Gly Gly Ala Thr Thr Cys Cys Cys Cys Gly Ala Cys Ala
1               5                   10                  15

Gly Ala Cys Cys Cys Thr Gly Gly Ala Gly Cys Cys Cys Thr Cys Thr
                20                  25                  30

Cys Ala Cys Cys Thr Thr Cys Thr Cys Cys Cys Cys Thr Gly Cys Cys
            35                  40                  45

Cys Ala Gly Cys Thr Gly Ala Cys Cys Gly Thr Cys Cys Ala Gly Gly
        50                  55                  60

Ala Ala Gly Gly Cys Gly Ala Gly Ala Ala Thr Gly Cys Cys Ala Cys
65                  70                  75                  80

Cys Thr Thr Cys Ala Cys Cys Thr Gly Cys Ala Gly Cys Cys Thr Cys
                85                  90                  95

Gly Cys Cys Gly Ala Cys Ala Thr Cys Cys Cys Cys Gly Ala Cys Ala
                100                 105                 110

Gly Cys Thr Thr Cys Gly Thr Gly Cys Thr Gly Ala Ala Cys Thr Gly
            115                 120                 125

Gly Thr Ala Cys Ala Gly Ala Cys Thr Gly Ala Gly Cys Cys Cys Cys
        130                 135                 140
```

Ala Gly Gly Ala Ala Cys Cys Ala Gly Ala Cys Gly Ala Cys Ala
145                 150                 155                 160

Ala Gly Cys Thr Gly Gly Cys Cys Gly Cys Thr Thr Cys Cys Ala
        165                 170                 175

Gly Gly Ala Gly Gly Ala Cys Ala Gly Gly Ala Thr Cys Gly Ala Ala
            180                 185                 190

Cys Cys Cys Gly Gly Cys Ala Gly Gly Ala Cys Ala Gly Gly Ala
        195                 200                 205

Gly Gly Thr Thr Thr Ala Gly Gly Thr Cys Ala Thr Gly Ala Gly
    210                 215                 220

Gly Cys Thr Gly Cys Cys Ala Ala Cys Gly Gly Cys Ala Gly Gly
225                 230                 235                 240

Gly Ala Cys Thr Thr Cys Cys Ala Cys Ala Thr Gly Thr Cys Cys Ala
            245                 250                 255

Thr Cys Gly Thr Gly Gly Cys Cys Gly Cys Cys Ala Gly Ala Cys Thr
        260                 265                 270

Gly Ala Ala Cys Gly Ala Cys Thr Cys Cys Gly Gly Cys Ala Thr Cys
    275                 280                 285

Thr Ala Cys Cys Thr Gly Thr Gly Cys Gly Gly Cys Gly Cys Thr Ala
290                 295                 300

Thr Cys Thr Ala Cys Cys Thr Gly Cys Cys Cys Cys Cys Ala Ala
305                 310                 315                 320

Cys Ala Cys Cys Cys Ala Gly Ala Thr Cys Ala Ala Cys Gly Ala Gly
            325                 330                 335

Ala Gly Cys Cys Cys Cys Ala Gly Gly Gly Cys Cys Gly Ala Ala Cys
        340                 345                 350

Thr Gly Ala Gly Cys Gly Thr Gly Ala Cys Ala Gly Ala Gly Ala Gly
    355                 360                 365

Ala Ala Cys Cys Cys Thr Gly Gly Ala Ala Cys Cys Thr Cys Cys Cys
370                 375                 380

Ala Cys Cys Cys Ala Gly Ala Cys Cys Cys Thr Thr Cys Cys Cys
385                 390                 395                 400

Cys Thr Cys Cys Thr Cys Cys Thr Ala Gly Ala Cys Thr Gly Ala Gly
        405                 410                 415

Cys Gly Gly Ala Cys Ala Gly Cys Thr Gly Cys Ala Gly Gly Cys
    420                 425                 430

Cys Thr Gly Gly Thr Gly
        435

<210> SEQ ID NO 5
<211> LENGTH: 1128
<212> TYPE: DNA
<213> ORGANISM: Artificial Sequence
<220> FEATURE:
<223> OTHER INFORMATION: codon optimized canine and human

<400> SEQUENCE: 5
ctggattccc ccgacagacc ctggagccct ctcaccttct ccctgccca gctgaccgtc     60 caggaaggcg agaatgccac cttcacctgc agcctcgccg acatccccga cagcttcgtg    120
ctgaactggt acagactgag ccccaggaac cagaccgaca gctggccgc tttccaggag    180 gacaggatcg aacccggcag ggacaggagg tttagggtca tgaggctgcc caacggcagg    240
gacttccaca tgtccatcgt ggccgccaga ctgaacgact ccggcatcta cctgtgcggc    300
gctatctacc tgccccccaa cacccagatc aacgagagcc caggccga actgagcgtg    360

```
acagagagaa ccctggaacc tcccacccag agcccttccc ctcctcctag actgagcgga    420
cagctgcagg gcctggtggg taccgacaaa actcacacat gcccaccgtg cccagcacct    480
gaactcctgg ggggaccgtc agtcttcctc ttccccccaa acccaagga caccctcatg     540 atctcccgga cccctgaggt cacatgcgtg gtggtggacg tgagccacga agaccctgag    600
gtcaagttca actggtacgt ggacggcgtg gaggtgcata atgccaagac aaagccgcgg    660
gaggagcagt acaacagcac gtaccgtgtg gtcagcgtcc tcaccgtcct gcaccaggac    720
tggctgaatg gcaaggagta caagtgcaag gtctccaaca aagccctccc agcccccatc    780
gagaaaacca tctccaaagc caagggcag ccccgagaac cacaggtgta caccctgccc     840
ccatcccggg atgagctgac caagaaccag gtcagcctga cctgcctggt caaaggcttc    900
tatcccagcg acatcgccgt ggagtgggag agcaatgggc agccggagaa caactacaag    960
accacgcctc ccgtgctgga ctccgacggc tccttcttcc tctacagcaa gctcaccgtg   1020
gacaagagca ggtggcagca ggggaacgtc ttctcatgct ccgtgatgca tgaggctctg   1080
cacaaccact acacgcagaa gagcctctcc ctgtctccgg gtaaatga               1128
```

<210> SEQ ID NO 6
<211> LENGTH: 375
<212> TYPE: PRT
<213> ORGANISM: Artificial Sequence
<220> FEATURE:
<223> OTHER INFORMATION: canine and human

<400> SEQUENCE: 6

```
Leu Asp Ser Pro Asp Arg Pro Trp Ser Pro Leu Thr Phe Ser Pro Ala
  1               5                  10                  15

Gln Leu Thr Val Gln Glu Gly Glu Asn Ala Thr Phe Thr Cys Ser Leu
             20                  25                  30

Ala Asp Ile Pro Asp Ser Phe Val Leu Asn Trp Tyr Arg Leu Ser Pro
         35                  40                  45

Arg Asn Gln Thr Asp Lys Leu Ala Ala Phe Gln Glu Asp Arg Ile Glu
     50                  55                  60

Pro Gly Arg Asp Arg Arg Phe Arg Val Met Arg Leu Pro Asn Gly Arg
 65                  70                  75                  80

Asp Phe His Met Ser Ile Val Ala Ala Arg Leu Asn Asp Ser Gly Ile
                 85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
        130                 135                 140

Leu Val Gly Thr Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
```

```
225                 230                 235                 240
Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 7
<211> LENGTH: 816
<212> TYPE: DNA
<213> ORGANISM: Canis familiaris

<400> SEQUENCE: 7
tttacgatca cagtttctaa ggacctgtat gtggtagagt atggtggcaa tgtgacaatg      60
gaatgcaaat tcccggtgga aaaacagtta aacttgtttg cactaatcgt ctactgggaa     120
atggaggata aaaaaattat acaatttgtg aatggaaagg aagacctgaa agttcagcac     180
agcagctaca gccagagggc tcagctattg aaggaccagc tcttcttggg aaggctgcg     240 cttcagatca cagatgtgag attgcaggat gcaggggttt actgctgctt gatcggctat     300
ggcggtgctg actacaagcg gattactttg aaagttcatg ccccgtaccg caacatcagc     360
caaagaattt ctgtggatcc tgtcacctct gaacatgaac taatgtgtca ggctgagggt     420 tacccctgagg ctgaagtcat ctggacaagc agtgaccacc gagtcctgag tggcaaaacc     480
accatcacta attccaatag gaagagaag ctttttcaatg tgaccagcac gctgaacatc     540
aatgcaacag ctaatgagat tttctactgc acttttcaaa gatcaggtcc tgaggaaaac     600
aatactgccg agttggtcat cccagaacga ctgcccgttc agcaagtga aggactcat     660 ttcatgattc tgggaccttt cctgttgctt cttggtgtag tcctggcagt cactttctgt     720
ctaaaaaaac atgggagaat gatggatgtg gaaaaatgtt gcacccgaga taggaactca     780
aagaaacgaa atgatataca atttgaagag acataa                                  816

<210> SEQ ID NO 8
<211> LENGTH: 271
<212> TYPE: PRT
<213> ORGANISM: Canis familiaris

<400> SEQUENCE: 8

Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30
```

```
Phe Ala Leu Ile Val Tyr Trp Glu Met Glu Asp Lys Lys Ile Ile Gln
             35                  40                  45
Phe Val Asn Gly Lys Glu Asp Leu Lys Val Gln His Ser Ser Tyr Ser
 50                  55                  60
Gln Arg Ala Gln Leu Leu Lys Asp Gln Leu Phe Leu Gly Lys Ala Ala
 65                  70                  75                  80
Leu Gln Ile Thr Asp Val Arg Leu Gln Asp Ala Gly Val Tyr Cys Cys
                 85                  90                  95
Leu Ile Gly Tyr Gly Gly Ala Asp Tyr Lys Arg Ile Thr Leu Lys Val
                100                 105                 110
His Ala Pro Tyr Arg Asn Ile Ser Gln Arg Ile Ser Val Asp Pro Val
            115                 120                 125
Thr Ser Glu His Glu Leu Met Cys Gln Ala Glu Gly Tyr Pro Glu Ala
130                 135                 140
Glu Val Ile Trp Thr Ser Ser Asp His Arg Val Leu Ser Gly Lys Thr
145                 150                 155                 160
Thr Ile Thr Asn Ser Asn Arg Glu Glu Lys Leu Phe Asn Val Thr Ser
                165                 170                 175
Thr Leu Asn Ile Asn Ala Thr Ala Asn Glu Ile Phe Tyr Cys Thr Phe
            180                 185                 190
Gln Arg Ser Gly Pro Glu Glu Asn Asn Thr Ala Glu Leu Val Ile Pro
        195                 200                 205
Glu Arg Leu Pro Val Pro Ala Ser Glu Arg Thr His Phe Met Ile Leu
210                 215                 220
Gly Pro Phe Leu Leu Leu Leu Gly Val Val Leu Ala Val Thr Phe Cys
225                 230                 235                 240
Leu Lys Lys His Gly Arg Met Met Asp Val Glu Lys Cys Cys Thr Arg
                245                 250                 255
Asp Arg Asn Ser Lys Lys Arg Asn Asp Ile Gln Phe Glu Glu Thr
            260                 265                 270

<210> SEQ ID NO 9
<211> LENGTH: 660
<212> TYPE: DNA
<213> ORGANISM: Artificial Sequence
<220> FEATURE:
<223> OTHER INFORMATION: codon optimized canine

<400> SEQUENCE: 9
tttaccatca ccgtgtccaa ggacctgtac gtggtcgagt acggcggcaa tgtgaccatg      60
gagtgcaagt tccccgtgga gaagcagctg aacctgttcg ccctcatcgt gtactgggag     120
atggaggaca gaagatcat ccagttcgtg aacggcaagg aggacctgaa ggtgcagcac     180
tccagctact cccagagagc ccagctgctg aaggaccagc tgttcctggg caaggccgcc     240
ctgcagatca ccgacgtgag actgcaggac gccggcgtgt attgctgcct gatcggctac     300
ggaggcgccg actacaagag gatcaccctg aaggtgcatg cccctacag gaacatcagc     360
cagaggatca gcgtcgatcc cgtgaccagc gagcacgagc tgatgtgcca agccgagggc     420
tatcccgagg ccgaagtgat ctggaccagc agcgaccaca gggtcctgag cggcaagacc     480
accatcacca cagcaacag ggaggagaag ctgttcaacg tgaccagcac cctcaacatc     540
aacgccaccg ccaacgagat cttctactgc accttccaga ggagcggccc cgaagagaac     600
aacaccgccg agctggtgat ccccgagaga ctgcctgtgc ctgccagcga gaggacccac     660

<210> SEQ ID NO 10
```

<211> LENGTH: 220
<212> TYPE: PRT
<213> ORGANISM: Canis familiaris

<400> SEQUENCE: 10

```
Phe Thr Ile Thr Val Ser Lys Asp Leu Tyr Val Val Glu Tyr Gly Gly
1               5                  10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80

Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His
    210                 215                 220
```

<210> SEQ ID NO 11
<211> LENGTH: 1350
<212> TYPE: DNA
<213> ORGANISM: Artificial Sequence
<220> FEATURE:
<223> OTHER INFORMATION: codon optimized canine and human

<400> SEQUENCE: 11

| | | | | | |
|---|---|---|---|---|---|
| tttaccatca | ccgtgtccaa | ggacctgtac | gtggtcgagt | acggcggcaa | tgtgaccatg | 60 |
| gagtgcaagt | tccccgtgga | gaagcagctg | aacctgttcg | ccctcatcgt | gtactgggag | 120 |
| atggaggaca | agaagatcat | ccagttcgtg | aacggcaagg | aggacctgaa | ggtgcagcac | 180 |
| tccagctact | cccagagagc | ccagctgctg | aaggaccagc | tgttcctggg | caaggccgcc | 240 |
| ctgcagatca | ccgacgtgag | actgcaggac | gccggcgtgt | attgctgcct | gatcggctac | 300 |
| ggaggcgccg | actacaagag | gatcaccctg | aaggtgcatg | caccctacag | gaacatcagc | 360 |
| cagaggatca | gcgtcgatcc | cgtgaccagc | gagcacgagc | tgatgtgcca | agccgagggc | 420 |
| tatcccgagg | ccgaagtgat | ctggaccagc | agcgaccaca | gggtcctgag | cggcaagacc | 480 |
| accatcacca | acagcaacag | ggaggagaag | ctgttcaacg | tgaccagcac | cctcaacatc | 540 |
| aacgccaccg | ccaacgagat | cttctactgc | accttccaga | ggagcggccc | cgaagagaac | 600 |
| aacaccgccg | agctggtgat | ccccgagaga | ctgcctgtgc | ctgccagcga | gaggacccac | 660 |

```
ggtaccgaca aaactcacac atgcccaccg tgcccagcac ctgaactcct gggggaccg      720 tcagtcttcc tcttcccccc aaaacccaag gacaccctca tgatctcccg gaccccagag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```

<210> SEQ ID NO 12
<211> LENGTH: 449
<212> TYPE: PRT
<213> ORGANISM: Artificial Sequence
<220> FEATURE:
<223> OTHER INFORMATION: canine and human

<400> SEQUENCE: 12

```
Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80

Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His Gly Thr Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 17
<212> TYPE: PRT
<213> ORGANISM: Mus musculus

<400> SEQUENCE: 13

Lys Ser Ser Gln Ser Leu Leu Asn Ser Val Asn Gln Lys Asn Tyr Leu
1               5                   10                  15

Ala

<210> SEQ ID NO 14
<211> LENGTH: 16
<212> TYPE: PRT
<213> ORGANISM: Mus musculus

<400> SEQUENCE: 14

Arg Ser Ser Gln Asn Ile Val His Ser Asn Gly Asn Thr Tyr Leu Glu
1               5                   10                  15

<210> SEQ ID NO 15
<211> LENGTH: 11
<212> TYPE: PRT
<213> ORGANISM: Mus musculus

<400> SEQUENCE: 15

His Ala Ser Gln Asn Ile Asn Val Trp Leu Ser
1               5                   10

<210> SEQ ID NO 16
```

```
<211> LENGTH: 7
<212> TYPE: PRT
<213> ORGANISM: Mus musculus

<400> SEQUENCE: 16

Phe Ala Ser Thr Arg Val Ser
1               5

<210> SEQ ID NO 17
<211> LENGTH: 7
<212> TYPE: PRT
<213> ORGANISM: Mus musculus

<400> SEQUENCE: 17

Lys Val Ser Asn Arg Phe Ser
1               5

<210> SEQ ID NO 18
<211> LENGTH: 7
<212> TYPE: PRT
<213> ORGANISM: Mus musculus

<400> SEQUENCE: 18

Lys Ala Ser His Leu His Thr
1               5

<210> SEQ ID NO 19
<211> LENGTH: 7
<212> TYPE: PRT
<213> ORGANISM: Mus musculus

<400> SEQUENCE: 19

Phe Ala Ser Ala Arg Val Ser
1               5

<210> SEQ ID NO 20
<211> LENGTH: 7
<212> TYPE: PRT
<213> ORGANISM: Mus musculus

<400> SEQUENCE: 20

Phe Ala Ser Thr Arg Ile Ser
1               5

<210> SEQ ID NO 21
<211> LENGTH: 7
<212> TYPE: PRT
<213> ORGANISM: Mus musculus

<400> SEQUENCE: 21

Lys Ala Ser Asn Leu His Thr
1               5

<210> SEQ ID NO 22
<211> LENGTH: 9
<212> TYPE: PRT
<213> ORGANISM: Mus musculus

<400> SEQUENCE: 22

Gln Gln Tyr Phe Ser Thr Pro Leu Thr
1               5

<210> SEQ ID NO 23
<211> LENGTH: 9
<212> TYPE: PRT
```

<213> ORGANISM: Mus musculus

<400> SEQUENCE: 23

Phe Gln Gly Ser His Val Pro Tyr Thr
1               5

<210> SEQ ID NO 24
<211> LENGTH: 9
<212> TYPE: PRT
<213> ORGANISM: Mus musculus

<400> SEQUENCE: 24

Gln Gln Gly Gln Ser Trp Pro Leu Thr
1               5

<210> SEQ ID NO 25
<211> LENGTH: 9
<212> TYPE: PRT
<213> ORGANISM: Mus musculus

<400> SEQUENCE: 25

Gln Gln Tyr Phe Ser Thr Pro Leu Thr
1               5

<210> SEQ ID NO 26
<211> LENGTH: 9
<212> TYPE: PRT
<213> ORGANISM: Mus musculus

<400> SEQUENCE: 26

Gln Gln Gly Gln Ser Tyr Pro Leu Thr
1               5

<210> SEQ ID NO 27
<211> LENGTH: 10
<212> TYPE: PRT
<213> ORGANISM: Mus musculus

<400> SEQUENCE: 27

Gly Tyr Thr Phe Thr Thr Tyr Gly Met Ser
1               5                   10

<210> SEQ ID NO 28
<211> LENGTH: 10
<212> TYPE: PRT
<213> ORGANISM: Mus musculus

<400> SEQUENCE: 28

Gly Tyr Thr Phe Thr Arg Tyr Asn Met His
1               5                   10

<210> SEQ ID NO 29
<211> LENGTH: 10
<212> TYPE: PRT
<213> ORGANISM: Mus musculus

<400> SEQUENCE: 29

Gly Phe Asn Ile Lys Asn Thr Tyr Met His
1               5                   10

<210> SEQ ID NO 30
<211> LENGTH: 10
<212> TYPE: PRT
<213> ORGANISM: Mus musculus

```
<400> SEQUENCE: 30

Gly Phe Ser Leu Thr Ser Tyr Gly Val His
1               5                   10

<210> SEQ ID NO 31
<211> LENGTH: 17
<212> TYPE: PRT
<213> ORGANISM: Mus musculus

<400> SEQUENCE: 31

Trp Ile Asn Ile Tyr Ser Gly Ile Pro Thr Tyr Ala Asp Asp Phe Lys
1               5                   10                  15

Gly

<210> SEQ ID NO 32
<211> LENGTH: 17
<212> TYPE: PRT
<213> ORGANISM: Mus musculus

<400> SEQUENCE: 32

Thr Ile Tyr Pro Gly Tyr Gly Asp Thr Ser Tyr Asn Gln Lys Phe Lys
1               5                   10                  15

Gly

<210> SEQ ID NO 33
<211> LENGTH: 17
<212> TYPE: PRT
<213> ORGANISM: Mus musculus

<400> SEQUENCE: 33

Arg Ile Ala Pro Ala Asn Val Asp Thr Lys Tyr Ala Pro Lys Phe Gln
1               5                   10                  15

Gly

<210> SEQ ID NO 34
<211> LENGTH: 17
<212> TYPE: PRT
<213> ORGANISM: Mus musculus

<400> SEQUENCE: 34

Trp Ile Asn Ile Tyr Ser Gly Met Pro Thr Tyr Ala Asp Asp Phe Lys
1               5                   10                  15

Gly

<210> SEQ ID NO 35
<211> LENGTH: 17
<212> TYPE: PRT
<213> ORGANISM: Mus musculus

<400> SEQUENCE: 35

Arg Ile Asp Pro Ala Asn Val Asn Thr Lys Tyr Ala Pro Lys Phe Gln
1               5                   10                  15

Gly

<210> SEQ ID NO 36
<211> LENGTH: 6
<212> TYPE: PRT
<213> ORGANISM: Mus musculus

<400> SEQUENCE: 36

Phe Asp Gly Pro Asp Tyr
```

```
<210> SEQ ID NO 37
<211> LENGTH: 13
<212> TYPE: PRT
<213> ORGANISM: Mus musculus

<400> SEQUENCE: 37

Glu Phe Ala Asp Asp Tyr Pro Ile Pro Pro Phe Asp Tyr
1               5                   10

<210> SEQ ID NO 38
<211> LENGTH: 11
<212> TYPE: PRT
<213> ORGANISM: Mus musculus

<400> SEQUENCE: 38

Ile Tyr Tyr Asp Tyr Asp Gly Asp Ile Asp Val
1               5                   10

<210> SEQ ID NO 39
<211> LENGTH: 336
<212> TYPE: PRT
<213> ORGANISM: Canis familiaris

<400> SEQUENCE: 39

Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
                20                  25                  30

Tyr Phe Pro Glu Pro Val Thr Val Ser Trp Asn Ser Gly Ser Leu Thr
            35                  40                  45

Ser Gly Val His Thr Phe Pro Ser Val Leu Gln Ser Ser Gly Leu Tyr
        50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Pro Lys Arg Glu Asn Gly Arg Val Arg Pro Pro Asp
            100                 105                 110

Cys Pro Lys Cys Pro Ala Pro Glu Met Leu Gly Gly Pro Ser Val Phe
        115                 120                 125

Ile Phe Pro Pro Lys Pro Lys Asp Thr Leu Leu Ile Ala Arg Thr Pro
    130                 135                 140

Glu Val Thr Cys Val Val Val Asp Leu Asp Pro Glu Asp Pro Glu Val
145                 150                 155                 160

Gln Ile Ser Trp Phe Val Asp Gly Lys Gln Met Gln Thr Ala Lys Thr
                165                 170                 175

Gln Pro Arg Glu Glu Gln Phe Asn Gly Thr Tyr Arg Val Val Ser Val
            180                 185                 190

Leu Pro Ile Gly His Gln Asp Trp Leu Lys Gly Lys Gln Phe Thr Cys
        195                 200                 205

Lys Val Asn Asn Lys Ala Leu Pro Ser Pro Ile Glu Arg Thr Ile Ser
    210                 215                 220

Lys Ala Arg Gly Gln Ala His Gln Pro Ser Val Tyr Val Leu Pro Pro
225                 230                 235                 240

Ser Arg Glu Glu Leu Ser Lys Asn Thr Val Ser Leu Thr Cys Leu Ile
                245                 250                 255
```

```
Lys Asp Phe Phe Pro Asp Ile Asp Val Glu Trp Gln Ser Asn Gly
            260                 265                 270

Gln Gln Glu Pro Glu Ser Lys Tyr Arg Thr Thr Pro Gln Leu Asp
        275                 280                 285

Glu Asp Gly Ser Tyr Phe Leu Tyr Ser Lys Leu Ser Val Asp Lys Ser
290                 295                 300

Arg Trp Gln Arg Gly Asp Thr Phe Ile Cys Ala Val Met His Glu Ala
305                 310                 315                 320

Leu His Asn His Tyr Thr Gln Glu Ser Leu Ser His Ser Pro Gly Lys
                325                 330                 335
```

<210> SEQ ID NO 40
<211> LENGTH: 331
<212> TYPE: PRT
<213> ORGANISM: Artificial Sequence
<220> FEATURE:
<223> OTHER INFORMATION: modified canine

<400> SEQUENCE: 40

```
Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
                20                  25                  30

Tyr Phe Pro Glu Pro Val Thr Val Ser Trp Asn Ser Gly Ser Leu Thr
            35                  40                  45

Ser Gly Val His Thr Phe Pro Ser Val Leu Gln Ser Ser Gly Leu Tyr
        50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Phe Asn Glu Cys Arg Cys Thr Asp Thr Pro Pro Cys Pro
            100                 105                 110

Ala Pro Glu Met Leu Gly Gly Pro Ser Val Phe Ile Phe Pro Pro Lys
        115                 120                 125

Pro Lys Ala Thr Leu Leu Ile Ala Arg Thr Pro Glu Val Thr Cys Val
130                 135                 140

Val Val Asp Leu Asp Pro Glu Asp Pro Glu Val Gln Ile Ser Trp Phe
145                 150                 155                 160

Val Asp Gly Lys Gln Met Gln Thr Ala Lys Thr Gln Pro Arg Glu Glu
                165                 170                 175

Gln Phe Ala Gly Thr Tyr Arg Val Val Ser Val Leu Pro Ile Gly His
            180                 185                 190

Gln Asp Trp Leu Lys Gly Lys Gln Phe Thr Cys Lys Val Asn Asn Lys
        195                 200                 205

Ala Leu Pro Ser Pro Ile Glu Arg Thr Ile Ser Lys Ala Arg Gly Gln
210                 215                 220

Ala His Gln Pro Ser Val Tyr Val Leu Pro Pro Ser Arg Glu Glu Leu
225                 230                 235                 240

Ser Lys Asn Thr Val Ser Leu Thr Cys Leu Ile Lys Asp Phe Phe Pro
                245                 250                 255

Pro Asp Ile Asp Val Glu Trp Gln Ser Asn Gly Gln Gln Glu Pro Glu
            260                 265                 270

Ser Lys Tyr Arg Thr Thr Pro Pro Gln Leu Asp Glu Asp Gly Ser Tyr
        275                 280                 285
```

Phe Leu Tyr Ser Lys Leu Ser Val Asp Lys Ser Arg Trp Gln Arg Gly
    290                 295                 300

Asp Thr Phe Ile Cys Ala Val Met His Glu Ala Leu His Asn His Tyr
305                 310                 315                 320

Thr Gln Glu Ser Leu Ser His Ser Pro Gly Lys
                325                 330

<210> SEQ ID NO 41
<211> LENGTH: 331
<212> TYPE: PRT
<213> ORGANISM: Artificial Sequence
<220> FEATURE:
<223> OTHER INFORMATION: modified canine

<400> SEQUENCE: 41

Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
                20                  25                  30

Tyr Phe Pro Glu Pro Val Thr Val Ser Trp Asn Ser Gly Ser Leu Thr
                35                  40                  45

Ser Gly Val His Thr Phe Pro Ser Val Leu Gln Ser Ser Gly Leu Tyr
    50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Pro Lys Glu Ser Thr Cys Lys Cys Ile Ser Pro Cys Pro
                100                 105                 110

Ala Pro Glu Met Leu Gly Gly Pro Ser Val Phe Ile Phe Pro Pro Lys
                115                 120                 125

Pro Lys Ala Thr Leu Leu Ile Ala Arg Thr Pro Glu Val Thr Cys Val
    130                 135                 140

Val Val Asp Leu Asp Pro Glu Asp Pro Glu Val Gln Ile Ser Trp Phe
145                 150                 155                 160

Val Asp Gly Lys Gln Met Gln Thr Ala Lys Thr Gln Pro Arg Glu Glu
                165                 170                 175

Gln Phe Ala Gly Thr Tyr Arg Val Val Ser Val Leu Pro Ile Gly His
                180                 185                 190

Gln Asp Trp Leu Lys Gly Lys Gln Phe Thr Cys Lys Val Asn Asn Lys
    195                 200                 205

Ala Leu Pro Ser Pro Ile Glu Arg Thr Ile Ser Lys Ala Arg Gly Gln
    210                 215                 220

Ala His Gln Pro Ser Val Tyr Val Leu Pro Pro Ser Arg Glu Glu Leu
225                 230                 235                 240

Ser Lys Asn Thr Val Ser Leu Thr Cys Leu Ile Lys Asp Phe Phe Pro
                245                 250                 255

Pro Asp Ile Asp Val Glu Trp Gln Ser Asn Gly Gln Gln Glu Pro Glu
                260                 265                 270

Ser Lys Tyr Arg Thr Thr Pro Pro Gln Leu Asp Glu Asp Gly Ser Tyr
    275                 280                 285

Phe Leu Tyr Ser Lys Leu Ser Val Asp Lys Ser Arg Trp Gln Arg Gly
    290                 295                 300

Asp Thr Phe Ile Cys Ala Val Met His Glu Ala Leu His Asn His Tyr
305                 310                 315                 320

```
Thr Gln Glu Ser Leu Ser His Ser Pro Gly Lys
            325                 330

<210> SEQ ID NO 42
<211> LENGTH: 336
<212> TYPE: PRT
<213> ORGANISM: Artificial Sequence
<220> FEATURE:
<223> OTHER INFORMATION: modified canine

<400> SEQUENCE: 42

Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
            20                  25                  30

Tyr Phe Pro Glu Pro Val Thr Val Ser Trp Asn Ser Gly Ser Leu Thr
            35                  40                  45

Ser Gly Val His Thr Phe Pro Ser Val Leu Gln Ser Ser Gly Leu Tyr
50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Pro Lys Arg Glu Asn Gly Arg Val Pro Arg Pro Pro Asp
            100                 105                 110

Cys Pro Lys Cys Pro Ala Pro Glu Met Leu Gly Gly Pro Ser Val Phe
        115                 120                 125

Ile Phe Pro Pro Lys Pro Lys Ala Thr Leu Leu Ile Ala Arg Thr Pro
    130                 135                 140

Glu Val Thr Cys Val Val Val Asp Leu Asp Pro Glu Asp Pro Glu Val
145                 150                 155                 160

Gln Ile Ser Trp Phe Val Asp Gly Lys Gln Met Gln Thr Ala Lys Thr
                165                 170                 175

Gln Pro Arg Glu Glu Gln Phe Ala Gly Thr Tyr Arg Val Val Ser Val
            180                 185                 190

Leu Pro Ile Gly His Gln Asp Trp Leu Lys Gly Lys Gln Phe Thr Cys
        195                 200                 205

Lys Val Asn Asn Lys Ala Leu Pro Ser Pro Ile Glu Arg Thr Ile Ser
    210                 215                 220

Lys Ala Arg Gly Gln Ala His Gln Pro Ser Val Tyr Val Leu Pro Pro
225                 230                 235                 240

Ser Arg Glu Glu Leu Ser Lys Asn Thr Val Ser Leu Thr Cys Leu Ile
                245                 250                 255

Lys Asp Phe Phe Pro Pro Asp Ile Asp Val Glu Trp Gln Ser Asn Gly
            260                 265                 270

Gln Gln Glu Pro Glu Ser Lys Tyr Arg Thr Thr Pro Pro Gln Leu Asp
        275                 280                 285

Glu Asp Gly Ser Tyr Phe Leu Tyr Ser Lys Leu Ser Val Asp Lys Ser
    290                 295                 300

Arg Trp Gln Arg Gly Asp Thr Phe Ile Cys Ala Val Met His Glu Ala
305                 310                 315                 320

Leu His Asn His Tyr Thr Gln Glu Ser Leu Ser His Ser Pro Gly Lys
                325                 330                 335

<210> SEQ ID NO 43
```

<211> LENGTH: 345
<212> TYPE: DNA
<213> ORGANISM: Mus musculus

<400> SEQUENCE: 43

```
cagatccagt tggtacagtc tggacctgaa ctgaagaagc ctggagagac agtcaagatc      60
tcctgcaagg cttctgggta taccttcaca acctatggaa tgagctgggt gaaacaggct     120
ccaggaaagg gtttaaagtg gatgggctgg attaatatct actctggaat cccaacatat     180
gctgatgact tcaagggacg gtttgccttc tctttggaaa cctctgccag cactgcctat     240
ttgcagatcg acaacctcaa aaatgaggac acggctacat atttctgtgc aagatttgat     300
ggtcccgact actggggcca aggcaccact ctcaccgtct cccca                     345
```

<210> SEQ ID NO 44
<211> LENGTH: 115
<212> TYPE: PRT
<213> ORGANISM: Mus musculus

<400> SEQUENCE: 44

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Thr Tyr
            20                  25                  30
Gly Met Ser Trp Val Lys Gln Ala Pro Gly Lys Gly Leu Lys Trp Met
        35                  40                  45
Gly Trp Ile Asn Ile Tyr Ser Gly Ile Pro Thr Tyr Ala Asp Asp Phe
    50                  55                  60
Lys Gly Arg Phe Ala Phe Ser Leu Glu Thr Ser Ala Ser Thr Ala Tyr
65                  70                  75                  80
Leu Gln Ile Asp Asn Leu Lys Asn Glu Asp Thr Ala Thr Tyr Phe Cys
                85                  90                  95
Ala Arg Phe Asp Gly Pro Asp Tyr Trp Gly Gln Gly Thr Thr Leu Thr
            100                 105                 110
Val Ser Pro
        115
```

<210> SEQ ID NO 45
<211> LENGTH: 339
<212> TYPE: DNA
<213> ORGANISM: Mus musculus

<400> SEQUENCE: 45

```
gacattgtga tgacacagtc tccatcctcc ctggctatgt cagtaggaca gaaggtcact      60
atgagctgca gtccagtca gagccttta aatagtgtca atcaaaagaa ctatttggcc     120
tggtaccagc agaaaccagg acagtctcct aaagttctgg tatactttgc atccactagg     180
gtatctgggg tccctgatcg cttcataggc agtggatctg ggacagattt cactcttacc     240
atcaccagtg tgcaggctga agacctgaca acttacctct gtcagcaata ttttagcact     300
cctctcacgt tcggtgctgg gaccaagctg gaaataaaa                            339
```

<210> SEQ ID NO 46
<211> LENGTH: 113
<212> TYPE: PRT
<213> ORGANISM: Mus musculus

<400> SEQUENCE: 46

```
Asp Ile Val Met Thr Gln Ser Pro Ser Ser Leu Ala Met Ser Val Gly
```

```
            1               5                  10                 15
         Gln Lys Val Thr Met Ser Cys Lys Ser Ser Gln Ser Leu Leu Asn Ser
                        20                  25                  30

Val Asn Gln Lys Asn Tyr Leu Ala Trp Tyr Gln Gln Lys Pro Gly Gln
                        35                  40                  45

Ser Pro Lys Val Leu Val Tyr Phe Ala Ser Thr Arg Val Ser Gly Val
                        50                  55                  60

Pro Asp Arg Phe Ile Gly Ser Gly Ser Gly Thr Asp Phe Thr Leu Thr
          65                 70                  75                  80

Ile Thr Ser Val Gln Ala Glu Asp Leu Thr Thr Tyr Leu Cys Gln Gln
                        85                  90                  95

Tyr Phe Ser Thr Pro Leu Thr Phe Gly Ala Gly Thr Lys Leu Glu Ile
                        100                 105                 110

Lys

<210> SEQ ID NO 47
<211> LENGTH: 423
<212> TYPE: DNA
<213> ORGANISM: Mus musculus

<400> SEQUENCE: 47
atgggattca gcaggatctt tctcttcctc ctgtcagtaa ctacaggtgt ccactcccag      60
gcttatctac agcagtctgg ggctgagctg gtgaggcctg ggcctcagt gaagatctcc     120 tgcaaggctt ctggctacac atttaccaga tacaatatgc actgggtaaa gcagacacct    180
agacagggcc tggaatggat tggaactatt tatcccggat atggtgatac ttcttacaat    240
cagaaattca agggcaaggc cacactgact gtagacatat cctccagcac agcctacatg    300
cagctcacca gcctgacatc tgaggactct gcggtctatt tctgttcaag ggagtttgcc    360
gatgattacc ccattccccc ctttgactac tggggccaag caccactct cacagtctcc    420 tca                                                                   423

<210> SEQ ID NO 48
<211> LENGTH: 141
<212> TYPE: PRT
<213> ORGANISM: Mus musculus

<400> SEQUENCE: 48

Met Gly Phe Ser Arg Ile Phe Leu Phe Leu Leu Ser Val Thr Thr Gly
 1               5                  10                  15

Val His Ser Gln Ala Tyr Leu Gln Gln Ser Gly Ala Glu Leu Val Arg
                20                  25                  30

Pro Gly Ala Ser Val Lys Ile Ser Cys Lys Ala Ser Gly Tyr Thr Phe
                35                  40                  45

Thr Arg Tyr Asn Met His Trp Val Lys Gln Thr Pro Arg Gln Gly Leu
         50                  55                  60

Glu Trp Ile Gly Thr Ile Tyr Pro Gly Tyr Gly Asp Thr Ser Tyr Asn
 65                 70                  75                  80

Gln Lys Phe Lys Gly Lys Ala Thr Leu Thr Val Asp Ile Ser Ser Ser
                85                  90                  95

Thr Ala Tyr Met Gln Leu Thr Ser Leu Thr Ser Glu Asp Ser Ala Val
                100                 105                 110

Tyr Phe Cys Ser Arg Glu Phe Ala Asp Asp Tyr Pro Ile Pro Pro Phe
                115                 120                 125

Asp Tyr Trp Gly Gln Gly Thr Thr Leu Thr Val Ser Ser
```

<210> SEQ ID NO 49
<211> LENGTH: 393
<212> TYPE: DNA
<213> ORGANISM: Mus musculus

<400> SEQUENCE: 49

```
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgtagat ctagtcagaa cattgtacat agtaatggaa acacctactt agaatggtac     180
ctgcagaaac caggccagtc tccaaagctc ctgatctaca aagtttccaa ccgatttttct    240
ggggtcccag acaggttcag tggcagtgga tcagggacag atttcacact caagatcagc     300
agagtggagg ctgaggatct gggaatttat tactgctttc aaggttcaca tgttccgtac     360
acgttcggag gggggaccaa gctggaaata aaa                                  393
```

<210> SEQ ID NO 50
<211> LENGTH: 131
<212> TYPE: PRT
<213> ORGANISM: Mus musculus

<400> SEQUENCE: 50

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Asn Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Tyr Cys
            100                 105                 110

Phe Gln Gly Ser His Val Pro Tyr Thr Phe Gly Gly Gly Thr Lys Leu
        115                 120                 125

Glu Ile Lys
    130

<210> SEQ ID NO 51
<211> LENGTH: 417
<212> TYPE: DNA
<213> ORGANISM: Mus musculus

<400> SEQUENCE: 51

```
atgaaattca gctgggtcat cttcttcctg atggcagtgg ttacaggggt caattcagag      60
gttcagctgc agcagtctgt ggcagagctt gtgaggccag ggcctcagt caagttgtcc      120
tgcacagctt ctggcttcaa cattaaaaac acctatatgc actggataaa acagaggcct     180
gaacagggcc tggagtggat tggaaggatt gctcctgcga atgttgatac taaatatgcc     240
ccgaagttcc agggcaaggc cactataact gcagacacat cctccaacac agcctacatg     300
cagctcagca ccctgacatc ggaggacact gccatctatt actgtgtcct gatctactat     360
```
gattacgacg gggacatcga tgtctggggc acagggacca cggtcaccgt ctcctca    417

<210> SEQ ID NO 52
<211> LENGTH: 139
<212> TYPE: PRT
<213> ORGANISM: Mus musculus

<400> SEQUENCE: 52

Met Lys Phe Ser Trp Val Ile Phe Phe Leu Met Ala Val Val Thr Gly
1               5                   10                  15

Val Asn Ser Glu Val Gln Leu Gln Gln Ser Val Ala Glu Leu Val Arg
            20                  25                  30

Pro Gly Ala Ser Val Lys Leu Ser Cys Thr Ala Ser Gly Phe Asn Ile
        35                  40                  45

Lys Asn Thr Tyr Met His Trp Ile Lys Gln Arg Pro Glu Gln Gly Leu
    50                  55                  60

Glu Trp Ile Gly Arg Ile Ala Pro Ala Asn Val Asp Thr Lys Tyr Ala
65                  70                  75                  80

Pro Lys Phe Gln Gly Lys Ala Thr Ile Thr Ala Asp Thr Ser Ser Asn
                85                  90                  95

Thr Ala Tyr Met Gln Leu Ser Thr Leu Thr Ser Glu Asp Thr Ala Ile
            100                 105                 110

Tyr Tyr Cys Val Leu Ile Tyr Tyr Asp Tyr Asp Gly Asp Ile Asp Val
        115                 120                 125

Trp Gly Thr Gly Thr Thr Val Thr Val Ser Ser
    130                 135

<210> SEQ ID NO 53
<211> LENGTH: 381
<212> TYPE: DNA
<213> ORGANISM: Mus musculus

<400> SEQUENCE: 53
atgagggtcc ttgctgagct cctggggctg ctgctgttct gcttttagg tgtgagatgt    60 gacatccaga tgaaccagtc tccatccagt ctgtctgcat cccttggaga cacaattacc    120
atcacttgcc atgccagtca gaacattaat gtttggttaa gttggtacca gcagagacca    180
ggaaatattc ctaaactatt gatctataag gcttctcact tacacacagg cgtcccatca    240
aggtttagtg gcagtggatc tggaacaggt ttcacattaa ccatcagcag cctgcagcct    300
gaagacattg ccacttacta ctgtcaacag ggtcaaagtt ggccgctcac gttcggtgct    360
gggaccaaac tggagctgaa a                                              381

<210> SEQ ID NO 54
<211> LENGTH: 127
<212> TYPE: PRT
<213> ORGANISM: Mus musculus

<400> SEQUENCE: 54

Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Ser Trp Tyr Gln Gln Arg Pro Gly Asn Ile Pro
    50                  55                  60

```
Lys Leu Leu Ile Tyr Lys Ala Ser His Leu His Thr Gly Val Pro Ser
 65                  70                  75                  80

Arg Phe Ser Gly Ser Gly Ser Gly Thr Gly Phe Thr Leu Thr Ile Ser
                 85                  90                  95

Ser Leu Gln Pro Glu Asp Ile Ala Thr Tyr Tyr Cys Gln Gln Gly Gln
            100                 105                 110

Ser Trp Pro Leu Thr Phe Gly Ala Gly Thr Lys Leu Glu Leu Lys
        115                 120                 125
```

<210> SEQ ID NO 55
<211> LENGTH: 402
<212> TYPE: DNA
<213> ORGANISM: Mus musculus

<400> SEQUENCE: 55

```
atgggttggc tgtggaactt gctattcctg atggcagctg cccaaagtgc ccaaacacag      60
atccagttgg tacagtctgg acctgaactg aagaagcctg gagagacagt caagatctcc     120
tgcaaggctt ctgggtatac cttcacaacc tatggaatga ctgggtgaa acaggctcca     180
ggaaagggtt taaagtggat gggctggatt aatatctact ctggaatccc aacatatgct     240
gatgacttca aggacgatt tgccttctct ttggaaacct ctgccagcac tgcctatttg     300
cagatcgaca acctcaaaaa tgaggacacg gctacatatt tctgtgcaag atttgatggt     360
cccgactact ggggccaagg caccactctc acagtctcct ca                      402
```

<210> SEQ ID NO 56
<211> LENGTH: 134
<212> TYPE: PRT
<213> ORGANISM: Mus musculus

<400> SEQUENCE: 56

```
Met Gly Trp Leu Trp Asn Leu Leu Phe Leu Met Ala Ala Ala Gln Ser
  1               5                  10                  15

Ala Gln Thr Gln Ile Gln Leu Val Gln Ser Gly Pro Glu Leu Lys Lys
             20                  25                  30

Pro Gly Glu Thr Val Lys Ile Ser Cys Lys Ala Ser Gly Tyr Thr Phe
         35                  40                  45

Thr Thr Tyr Gly Met Ser Trp Val Lys Gln Ala Pro Gly Lys Gly Leu
     50                  55                  60

Lys Trp Met Gly Trp Ile Asn Ile Tyr Ser Gly Ile Pro Thr Tyr Ala
 65                  70                  75                  80

Asp Asp Phe Lys Gly Arg Phe Ala Phe Ser Leu Glu Thr Ser Ala Ser
                 85                  90                  95

Thr Ala Tyr Leu Gln Ile Asp Asn Leu Lys Asn Glu Asp Thr Ala Thr
            100                 105                 110

Tyr Phe Cys Ala Arg Phe Asp Gly Pro Asp Tyr Trp Gly Gln Gly Thr
        115                 120                 125

Thr Leu Thr Val Ser Ser
        130
```

<210> SEQ ID NO 57
<211> LENGTH: 399
<212> TYPE: DNA
<213> ORGANISM: Mus musculus

<400> SEQUENCE: 57

```
atggaatcac agacccaggt cctcatgttt cttctgctct gggtatctgg tgcctgtgca      60
```

```
gacattgtga tgacacagtc tccatcctcc ctggctgtgt cagtaggacg gaaggtcact      120
atgagctgca agtccagtca gagccttttta aatagtgtca atcaaaagaa ctatttggcc     180
tggtaccagc agaaaccagg acagtctcct aaagttctgg tatactttgc atccgctagg     240
gtatctgggg tccctgatcg cttcataggc agtggatctg ggacagattt cactcttgcc     300
atcagcagtg tgcaggctga agacctgaca acttacttct gtcagcaata ttttagcact     360
cctctcacgt tcggtgctgg gaccaagctg gaactgaaa                            399
```

<210> SEQ ID NO 58
<211> LENGTH: 133
<212> TYPE: PRT
<213> ORGANISM: Mus musculus

<400> SEQUENCE: 58

```
Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Val Ser Val Gly Arg Lys Val Thr Met Ser Cys Lys Ser Ser Gln Ser
        35                  40                  45

Leu Leu Asn Ser Val Asn Gln Lys Asn Tyr Leu Ala Trp Tyr Gln Gln
    50                  55                  60

Lys Pro Gly Gln Ser Pro Lys Val Leu Val Tyr Phe Ala Ser Ala Arg
65                  70                  75                  80

Val Ser Gly Val Pro Asp Arg Phe Ile Gly Ser Gly Ser Gly Thr Asp
                85                  90                  95

Phe Thr Leu Ala Ile Ser Ser Val Gln Ala Glu Asp Leu Thr Thr Tyr
            100                 105                 110

Phe Cys Gln Gln Tyr Phe Ser Thr Pro Leu Thr Phe Gly Ala Gly Thr
        115                 120                 125

Lys Leu Glu Leu Lys
    130
```

<210> SEQ ID NO 59
<211> LENGTH: 402
<212> TYPE: DNA
<213> ORGANISM: Mus musculus

<400> SEQUENCE: 59

```
atgggttggc tgtggaactt gctattcctg atggcagctg cccaaagtgc caagcacag       60 atccagttgg tacagtctgg acctgaactg aagaagcctg agagacagt caagatctcc     120 tgcaaggctt ctgggtatac cttcacaacc tatggaatga gctgggtgaa acaggcgcca     180
ggaaagggtt taaagtggat gggctggata aatatctact ctggaatgcc aacatatgct     240
gatgacttca agggacggtt tgccttctct ttggaaacct ctgtcagcac tgcctatttg     300
cagatcaaca acctcaaaaa tgaggacacg gctacatatt tctgtgcaag atttgatggt     360
cccgactact ggggccaagg caccactctc acagtctcct ca                       402
```

<210> SEQ ID NO 60
<211> LENGTH: 134
<212> TYPE: PRT
<213> ORGANISM: Mus musculus

<400> SEQUENCE: 60

```
Met Gly Trp Leu Trp Asn Leu Leu Phe Leu Met Ala Ala Ala Gln Ser
1               5                   10                  15
```

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Thr Tyr Gly Met Ser Trp Val Lys Gln Ala Pro Gly Lys Gly Leu
    50                  55                  60

Lys Trp Met Gly Trp Ile Asn Ile Tyr Ser Gly Met Pro Thr Tyr Ala
65                  70                  75                  80

Asp Asp Phe Lys Gly Arg Phe Ala Phe Ser Leu Glu Thr Ser Val Ser
                85                  90                  95

Thr Ala Tyr Leu Gln Ile Asn Asn Leu Lys Asn Glu Asp Thr Ala Thr
            100                 105                 110

Tyr Phe Cys Ala Arg Phe Asp Gly Pro Asp Tyr Trp Gly Gln Gly Thr
        115                 120                 125

Thr Leu Thr Val Ser Ser
    130

<210> SEQ ID NO 61
<211> LENGTH: 399
<212> TYPE: DNA
<213> ORGANISM: Mus musculus

<400> SEQUENCE: 61
atggaatcac agacccaggt cctcatgttt cttctgctct gggtatctgg tgcctgtgca      60
gacattgtga tgacacagtc tccatcctcc ctggctatgt cagtaggaca gaaggtcact     120
atgagctgca agtccagtca gagccttttta aatagtgtca atcaaaagaa ctatttggcc    180
tggtaccagc agaaaccagg acagtctcct aaagttctgg tatactttgc atccactagg     240
atatctgggg tccctgatcg cttcataggc agtggatctg gacagatttt cactcttacc     300
atcagcagtg tgcaggctga agacctggca gattacttct gtcagcaata ttttagcact     360
cctctcacgt tcggtgctgg gaccaagctg gagctgaaa                            399

<210> SEQ ID NO 62
<211> LENGTH: 133
<212> TYPE: PRT
<213> ORGANISM: Mus musculus

<400> SEQUENCE: 62

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Val Asn Gln Lys Asn Tyr Leu Ala Trp Tyr Gln Gln
    50                  55                  60

Lys Pro Gly Gln Ser Pro Lys Val Leu Val Tyr Phe Ala Ser Thr Arg
65                  70                  75                  80

Ile Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln Tyr Phe Ser Thr Pro Leu Thr Phe Gly Ala Gly Thr
        115                 120                 125

Lys Leu Glu Leu Lys
    130

<210> SEQ ID NO 63
<211> LENGTH: 417
<212> TYPE: DNA
<213> ORGANISM: Mus musculus

<400> SEQUENCE: 63

| | | | | | |
|---|---|---|---|---|---|
| atgaaattca | gctgggtcat | cttcttcctg | atggcagtgg | ttacaggggt | caattcagag | 60 |
| gttcagctgc | agcagtctgt | ggcagagctt | gtgaggccag | gggcctcagt | caagttgtcc | 120 |
| tgcacagttt | ctggcttcaa | cattaaaaac | acctatatgc | actgggtgaa | gcagaggcct | 180 |
| gaacagggcc | tggagtggat | tggaagaatt | gatcctgcga | atgttaatac | taaatatgcc | 240 |
| ccgaagttcc | agggcaaggc | cactataact | acagacacat | cctccaacac | agcctacatg | 300 |
| cagctcagca | gcctgacatc | ggaggacact | gccatctatt | actgtgtcct | gattttctat | 360 |
| gattacgacg | ggacatcga | tgtctggggc | acagggacca | aggtcaccgt | ctcctca | 417 |

<210> SEQ ID NO 64
<211> LENGTH: 139
<212> TYPE: PRT
<213> ORGANISM: Mus musculus

<400> SEQUENCE: 64

Met Lys Phe Ser Trp Val Ile Phe Phe Leu Met Ala Val Val Thr Gly
1               5                   10                  15

Val Asn Ser Glu Val Gln Leu Gln Gln Ser Val Ala Glu Leu Val Arg
            20                  25                  30

Pro Gly Ala Ser Val Lys Leu Ser Cys Thr Val Ser Gly Phe Asn Ile
        35                  40                  45

Lys Asn Thr Tyr Met His Trp Val Lys Gln Arg Pro Glu Gln Gly Leu
    50                  55                  60

Glu Trp Ile Gly Arg Ile Asp Pro Ala Asn Val Asn Thr Lys Tyr Ala
65                  70                  75                  80

Pro Lys Phe Gln Gly Lys Ala Thr Ile Thr Thr Asp Thr Ser Ser Asn
                85                  90                  95

Thr Ala Tyr Met Gln Leu Ser Ser Leu Thr Ser Glu Asp Thr Ala Ile
            100                 105                 110

Tyr Tyr Cys Val Leu Ile Phe Tyr Asp Tyr Asp Gly Asp Ile Asp Val
        115                 120                 125

Trp Gly Thr Gly Thr Lys Val Thr Val Ser Ser
    130                 135

<210> SEQ ID NO 65
<211> LENGTH: 381
<212> TYPE: DNA
<213> ORGANISM: Mus musculus

<400> SEQUENCE: 65

| | | | | | |
|---|---|---|---|---|---|
| atgagggtcc | ttgctgagct | cctggggctg | ctgctgttct | gcttttttagg | tgtgagatgt | 60 |
| gacatccaga | tgaaccagtc | tccatccagt | ctgtctgcat | cccttggaga | cacaattacc | 120 |
| atcacttgcc | atgccagtca | gaacattaat | gtttggttaa | gctggtacca | gcagaaacca | 180 |
| ggaaatattc | ctaaactatt | gatctataag | gcttccaact | tacacacagg | cgtcccatca | 240 |
| aggtttagtg | gcagtggatc | tggaacagat | ttcacattaa | ccatcagcag | cctgcagcct | 300 |
| gaagacattg | ccacttacta | ctgtcaacag | ggtcaaagtt | atccgctcac | gttcggtgct | 360 | gggaccaagc tggagctgaa a                                                    381

<210> SEQ ID NO 66
<211> LENGTH: 127
<212> TYPE: PRT
<213> ORGANISM: Mus musculus

<400> SEQUENCE: 66

Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Ser Trp Tyr Gln Gln Lys Pro Gly Asn Ile Pro
    50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Ile Ala Thr Tyr Tyr Cys Gln Gln Gly Gln
            100                 105                 110

Ser Tyr Pro Leu Thr Phe Gly Ala Gly Thr Lys Leu Glu Leu Lys
        115                 120                 125

<210> SEQ ID NO 67
<211> LENGTH: 345
<212> TYPE: DNA
<213> ORGANISM: Mus musculus

<400> SEQUENCE: 67
caggtgcagc tgaagcagtc aggacctggc ctagtgcagc cctcacagag cctgtccata     60
acctgcacag tctctggttt ctcattaact agctatggtg tacactgggt tcgccagtct    120
ccaggaaagg gtttaaagtg gatgggctgg attaatatct actctggaat cccaacatat    180
gctgatgact tcaagggacg gtttgccttc tctttggaaa cctctgccag cactgcctat    240
ttgcagatcg acaacctcaa aaatgaggac acggctacat atttctgtgc aagatttgat    300
ggtcccgact actggggcca aggcatcact ctcactgtct ccgca                    345

<210> SEQ ID NO 68
<211> LENGTH: 115
<212> TYPE: PRT
<213> ORGANISM: Mus musculus

<400> SEQUENCE: 68

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Lys Trp Met
        35                  40                  45

Gly Trp Ile Asn Ile Tyr Ser Gly Ile Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asp Asn Leu Lys Asn Glu Asp Thr Ala Thr Tyr Phe Cys 85                  90                  95

Ala Arg Phe Asp Gly Pro Asp Tyr Trp Gly Gln Gly Ile Thr Leu Thr
                100                 105                 110

Val Ser Ala
        115

<210> SEQ ID NO 69
<211> LENGTH: 339
<212> TYPE: DNA
<213> ORGANISM: Mus musculus

<400> SEQUENCE: 69
gacattgtga tgacacagtc tccatcctcc ctggctatgt cagtaggaca gaaggtcact      60
atgagctgca gtccagtca gagccttta aatagtgtca atcaaaagaa ctatttggcc      120
tggtaccagc agaaaccagg acagtctcct aaagttctgg tatactttgc atccactagg     180
gtatctgggg tccctgatcg cttcataggc agtggatctg ggacagattt cactcttacc     240
atcaccagtg tgcaggctga agacctgaca acttacttct gtcagcaata ttttagcact     300
cctctcacgt tcggtgctgg gaccaagctg gaactgaaa                             339

<210> SEQ ID NO 70
<211> LENGTH: 113
<212> TYPE: PRT
<213> ORGANISM: Mus musculus

<400> SEQUENCE: 70

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Val Asn Gln Lys Asn Tyr Leu Ala Trp Tyr Gln Gln Lys Pro Gly Gln
        35                  40                  45

Ser Pro Lys Val Leu Val Tyr Phe Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Thr Ser Val Gln Ala Glu Asp Leu Thr Thr Tyr Phe Cys Gln Gln
                85                  90                  95

Tyr Phe Ser Thr Pro Leu Thr Phe Gly Ala Gly Thr Lys Leu Glu Leu
                100                 105                 110

Lys

<210> SEQ ID NO 71
<211> LENGTH: 15
<212> TYPE: PRT
<213> ORGANISM: Canis familiaris

<400> SEQUENCE: 71

Leu Asp Ser Pro Asp Arg Pro Trp Ser Pro Leu Thr Phe Ser Pro
1               5                   10                  15

<210> SEQ ID NO 72
<211> LENGTH: 15
<212> TYPE: PRT
<213> ORGANISM: Canis familiaris

<400> SEQUENCE: 72

Arg Pro Trp Ser Pro Leu Thr Phe Ser Pro Ala Gln Leu Thr Val

```
                1               5                    10                   15
```

<210> SEQ ID NO 73
<211> LENGTH: 15
<212> TYPE: PRT
<213> ORGANISM: Canis familiaris

<400> SEQUENCE: 73

```
Leu Thr Phe Ser Pro Ala Gln Leu Thr Val Gln Glu Gly Glu Asn
1               5                    10                   15
```

<210> SEQ ID NO 74
<211> LENGTH: 15
<212> TYPE: PRT
<213> ORGANISM: Canis familiaris

<400> SEQUENCE: 74

```
Ala Gln Leu Thr Val Gln Glu Gly Glu Asn Ala Thr Phe Thr Cys
1               5                    10                   15
```

<210> SEQ ID NO 75
<211> LENGTH: 15
<212> TYPE: PRT
<213> ORGANISM: Canis familiaris

<400> SEQUENCE: 75

```
Gln Glu Gly Glu Asn Ala Thr Phe Thr Cys Ser Leu Ala Asp Ile
1               5                    10                   15
```

<210> SEQ ID NO 76
<211> LENGTH: 15
<212> TYPE: PRT
<213> ORGANISM: Canis familiaris

<400> SEQUENCE: 76

```
Ala Thr Phe Thr Cys Ser Leu Ala Asp Ile Pro Asp Ser Phe Val
1               5                    10                   15
```

<210> SEQ ID NO 77
<211> LENGTH: 15
<212> TYPE: PRT
<213> ORGANISM: Canis familiaris

<400> SEQUENCE: 77

```
Ser Leu Ala Asp Ile Pro Asp Ser Phe Val Leu Asn Trp Tyr Arg
1               5                    10                   15
```

<210> SEQ ID NO 78
<211> LENGTH: 15
<212> TYPE: PRT
<213> ORGANISM: Canis familiaris

<400> SEQUENCE: 78

```
Pro Asp Ser Phe Val Leu Asn Trp Tyr Arg Leu Ser Pro Arg Asn
1               5                    10                   15
```

<210> SEQ ID NO 79
<211> LENGTH: 15
<212> TYPE: PRT
<213> ORGANISM: Canis familiaris

<400> SEQUENCE: 79

```
Leu Asn Trp Tyr Arg Leu Ser Pro Arg Asn Gln Thr Asp Lys Leu
1               5                    10                   15
```

<210> SEQ ID NO 80
<211> LENGTH: 15
<212> TYPE: PRT
<213> ORGANISM: Canis familiaris

<400> SEQUENCE: 80

Leu Ser Pro Arg Asn Gln Thr Asp Lys Leu Ala Ala Phe Gln Glu
1               5                   10                  15

<210> SEQ ID NO 81
<211> LENGTH: 15
<212> TYPE: PRT
<213> ORGANISM: Canis familiaris

<400> SEQUENCE: 81

Gln Thr Asp Lys Leu Ala Ala Phe Gln Glu Asp Arg Ile Glu Pro
1               5                   10                  15

<210> SEQ ID NO 82
<211> LENGTH: 15
<212> TYPE: PRT
<213> ORGANISM: Canis familiaris

<400> SEQUENCE: 82

Ala Ala Phe Gln Glu Asp Arg Ile Glu Pro Gly Arg Asp Arg Arg
1               5                   10                  15

<210> SEQ ID NO 83
<211> LENGTH: 15
<212> TYPE: PRT
<213> ORGANISM: Canis familiaris
<220> FEATURE:
<221> NAME/KEY: MISC_FEATURE
<222> LOCATION: (14)..(14)
<223> OTHER INFORMATION: Xaa can be Met or Thr

<400> SEQUENCE: 83

Asp Arg Ile Glu Pro Gly Arg Asp Arg Arg Phe Arg Val Xaa Arg
1               5                   10                  15

<210> SEQ ID NO 84
<211> LENGTH: 15
<212> TYPE: PRT
<213> ORGANISM: Canis familiaris
<220> FEATURE:
<221> NAME/KEY: MISC_FEATURE
<222> LOCATION: (9)..(9)
<223> OTHER INFORMATION: Xaa can be Met or Thr

<400> SEQUENCE: 84

Gly Arg Asp Arg Arg Phe Arg Val Xaa Arg Leu Pro Asn Gly Arg
1               5                   10                  15

<210> SEQ ID NO 85
<211> LENGTH: 15
<212> TYPE: PRT
<213> ORGANISM: Canis familiaris
<220> FEATURE:
<221> NAME/KEY: MISC_FEATURE
<222> LOCATION: (4)..(4)
<223> OTHER INFORMATION: Xaa can be Met or Thr

<400> SEQUENCE: 85

Phe Arg Val Xaa Arg Leu Pro Asn Gly Arg Asp Phe His Met Ser
1               5                   10                  15

-continued

<210> SEQ ID NO 86
<211> LENGTH: 15
<212> TYPE: PRT
<213> ORGANISM: Canis familiaris

<400> SEQUENCE: 86

Leu Pro Asn Gly Arg Asp Phe His Met Ser Ile Val Ala Ala Arg
1               5                   10                  15

<210> SEQ ID NO 87
<211> LENGTH: 15
<212> TYPE: PRT
<213> ORGANISM: Canis familiaris

<400> SEQUENCE: 87

Asp Phe His Met Ser Ile Val Ala Ala Arg Leu Asn Asp Ser Gly
1               5                   10                  15

<210> SEQ ID NO 88
<211> LENGTH: 15
<212> TYPE: PRT
<213> ORGANISM: Canis familiaris

<400> SEQUENCE: 88

Ile Val Ala Ala Arg Leu Asn Asp Ser Gly Ile Tyr Leu Cys Gly
1               5                   10                  15

<210> SEQ ID NO 89
<211> LENGTH: 15
<212> TYPE: PRT
<213> ORGANISM: Canis familiaris

<400> SEQUENCE: 89

Leu Asn Asp Ser Gly Ile Tyr Leu Cys Gly Ala Ile Tyr Leu Pro
1               5                   10                  15

<210> SEQ ID NO 90
<211> LENGTH: 15
<212> TYPE: PRT
<213> ORGANISM: Canis familiaris

<400> SEQUENCE: 90

Ile Tyr Leu Cys Gly Ala Ile Tyr Leu Pro Pro Asn Thr Gln Ile
1               5                   10                  15

<210> SEQ ID NO 91
<211> LENGTH: 15
<212> TYPE: PRT
<213> ORGANISM: Canis familiaris

<400> SEQUENCE: 91

Ala Ile Tyr Leu Pro Pro Asn Thr Gln Ile Asn Glu Ser Pro Arg
1               5                   10                  15

<210> SEQ ID NO 92
<211> LENGTH: 15
<212> TYPE: PRT
<213> ORGANISM: Canis familiaris

<400> SEQUENCE: 92

Pro Asn Thr Gln Ile Asn Glu Ser Pro Arg Ala Glu Leu Ser Val
1               5                   10                  15

<210> SEQ ID NO 93
<211> LENGTH: 15

```
<212> TYPE: PRT
<213> ORGANISM: Canis familiaris

<400> SEQUENCE: 93

Asn Glu Ser Pro Arg Ala Glu Leu Ser Val Thr Glu Arg Thr Leu
1               5                   10                  15

<210> SEQ ID NO 94
<211> LENGTH: 15
<212> TYPE: PRT
<213> ORGANISM: Canis familiaris

<400> SEQUENCE: 94

Ala Glu Leu Ser Val Thr Glu Arg Thr Leu Glu Pro Pro Thr Gln
1               5                   10                  15

<210> SEQ ID NO 95
<211> LENGTH: 15
<212> TYPE: PRT
<213> ORGANISM: Canis familiaris

<400> SEQUENCE: 95

Thr Glu Arg Thr Leu Glu Pro Pro Thr Gln Ser Pro Ser Pro Pro
1               5                   10                  15

<210> SEQ ID NO 96
<211> LENGTH: 15
<212> TYPE: PRT
<213> ORGANISM: Canis familiaris

<400> SEQUENCE: 96

Glu Pro Pro Thr Gln Ser Pro Ser Pro Pro Arg Leu Ser Gly
1               5                   10                  15

<210> SEQ ID NO 97
<211> LENGTH: 15
<212> TYPE: PRT
<213> ORGANISM: Canis familiaris

<400> SEQUENCE: 97

Ser Pro Ser Pro Pro Arg Leu Ser Gly Gln Leu Gln Gly Leu
1               5                   10                  15

<210> SEQ ID NO 98
<211> LENGTH: 15
<212> TYPE: PRT
<213> ORGANISM: Canis familiaris

<400> SEQUENCE: 98

Pro Ser Pro Pro Arg Leu Ser Gly Gln Leu Gln Gly Leu Val
1               5                   10                  15

<210> SEQ ID NO 99
<211> LENGTH: 25
<212> TYPE: PRT
<213> ORGANISM: Canis familiaris
<220> FEATURE:
<221> NAME/KEY: MISC_FEATURE
<222> LOCATION: (5)..(5)
<223> OTHER INFORMATION: Xaa can be Met or Thr

<400> SEQUENCE: 99

Arg Phe Arg Val Xaa Arg Leu Pro Asn Gly Arg Asp Phe His Met Ser
1               5                   10                  15

Ile Val Ala Ala Arg Leu Asn Asp Ser
```

```
                    20                  25

<210> SEQ ID NO 100
<211> LENGTH: 26
<212> TYPE: PRT
<213> ORGANISM: Canis familiaris
<220> FEATURE:
<221> NAME/KEY: misc_feature
<222> LOCATION: (20)..(20)
<223> OTHER INFORMATION: Xaa can be any naturally occurring amino acid

<400> SEQUENCE: 100

Leu Ala Ala Phe Gln Glu Asp Arg Ile Glu Pro Gly Arg Asp Arg Arg
1               5                   10                  15

Phe Arg Val Xaa Arg Leu Pro Asn Gly Arg
            20                  25

<210> SEQ ID NO 101
<211> LENGTH: 31
<212> TYPE: PRT
<213> ORGANISM: Canis familiaris
<220> FEATURE:
<221> NAME/KEY: MISC_FEATURE
<222> LOCATION: (15)..(15)
<223> OTHER INFORMATION: Xaa can be Met or Thr

<400> SEQUENCE: 101

Glu Asp Arg Ile Glu Pro Gly Arg Asp Arg Arg Phe Arg Val Xaa Arg
1               5                   10                  15

Leu Pro Asn Gly Arg Asp Phe His Met Ser Ile Val Ala Ala Arg
            20                  25                  30

<210> SEQ ID NO 102
<211> LENGTH: 31
<212> TYPE: PRT
<213> ORGANISM: Canis familiaris
<220> FEATURE:
<221> NAME/KEY: MISC_FEATURE
<222> LOCATION: (25)..(25)
<223> OTHER INFORMATION: Xaa can be Met or Thr

<400> SEQUENCE: 102

Asn Gln Thr Asp Lys Leu Ala Ala Phe Gln Glu Asp Arg Ile Glu Pro
1               5                   10                  15

Gly Arg Asp Arg Arg Phe Arg Val Xaa Arg Leu Pro Asn Gly Arg
            20                  25                  30

<210> SEQ ID NO 103
<211> LENGTH: 45
<212> TYPE: PRT
<213> ORGANISM: Canis familiaris
<220> FEATURE:
<221> NAME/KEY: MISC_FEATURE
<222> LOCATION: (25)..(25)
<223> OTHER INFORMATION: Xaa can be Met or Thr

<400> SEQUENCE: 103

Asn Gln Thr Asp Lys Leu Ala Ala Phe Gln Glu Asp Arg Ile Glu Pro
1               5                   10                  15

Gly Arg Asp Arg Arg Phe Arg Val Xaa Arg Leu Pro Asn Gly Arg Asp
            20                  25                  30

Phe His Met Ser Ile Val Ala Ala Arg Leu Asn Asp Ser
        35                  40                  45

<210> SEQ ID NO 104
```

-continued

<211> LENGTH: 20
<212> TYPE: PRT
<213> ORGANISM: Canis familiaris
<220> FEATURE:
<221> NAME/KEY: misc_feature
<222> LOCATION: (14)..(14)
<223> OTHER INFORMATION: Xaa can be Met or Thr

<400> SEQUENCE: 104

Asp Arg Ile Glu Pro Gly Arg Asp Arg Arg Phe Arg Val Xaa Arg Leu
1               5                   10                  15

Pro Asn Gly Arg
            20

<210> SEQ ID NO 105
<211> LENGTH: 867
<212> TYPE: DNA
<213> ORGANISM: Canis familiaris

<400> SEQUENCE: 105
atggggagcc ggcgggggcc ctggccgctc gtctgggccg tgctgcagct gggctggtgg    60
ccaggatggc tcctagactc ccctgacagg ccctggagcc cgctcacctt ctccccggcg   120
cagctcacgg tgcaggaggg agagaacgcc acgttcacct gcagcctggc cgacatcccc   180
gacagcttcg tgctcaactg gtaccgcctg agccccgca accagacgga caagctggcc    240
gccttccagg aggaccgcat cgagccgggc cgggacaggc gcttccgcgt catgcggctg   300
cccaacgggc gggacttcca catgagcatc gtcgctgcgc cctcaacga cagcggcatc    360 tacctgtgcg gggccatcta cctgcccccc aacacacaga tcaacgagag tccccgcgca   420
gagctctccg tgacggagag aaccctggag ccccccacac agagcccag ccccccaccc    480 agactcagcg ccagttgca ggggctggtc atcggcgtca cgagcgtgct ggtgggtgtc    540
ctgctactgc tgctgctgac ctgggtcctg gccgctgtct tccccagggc cacccgaggt   600
gcctgtgtgt gcgggagcga ggacgagcct ctgaaggagg ccccgatgc agcgcccgtc    660 ttcaccctgg actacgggga gctggacttc cagtggcgag agaagacgcc ggagccccg    720 gcgccctgtg ccccggagca gaccgagtat gccaccatcg tcttcccggg caggccggcg   780
tccccgggcc gcagggcctc ggccagcagc ctgcaggag cccagcctcc gagccccgag   840
gacggacccg gcctgtggcc cctctga                                       867

<210> SEQ ID NO 106
<211> LENGTH: 288
<212> TYPE: PRT
<213> ORGANISM: Canis familiaris

<400> SEQUENCE: 106

Met Gly Ser Arg Arg Gly Pro Trp Pro Leu Val Trp Ala Val Leu Gln
1               5                   10                  15

Leu Gly Trp Trp Pro Gly Trp Leu Leu Asp Ser Pro Asp Arg Pro Trp
            20                  25                  30

Ser Pro Leu Thr Phe Ser Pro Ala Gln Leu Thr Val Gln Glu Gly Glu
        35                  40                  45

Asn Ala Thr Phe Thr Cys Ser Leu Ala Asp Ile Pro Asp Ser Phe Val
    50                  55                  60

Leu Asn Trp Tyr Arg Leu Ser Pro Arg Asn Gln Thr Asp Lys Leu Ala
65                  70                  75                  80

Ala Phe Gln Glu Asp Arg Ile Glu Pro Gly Arg Asp Arg Arg Phe Arg
                85                  90                  95

Val Met Arg Leu Pro Asn Gly Arg Asp Phe His Met Ser Ile Val Ala
            100                 105                 110

Ala Arg Leu Asn Asp Ser Gly Ile Tyr Leu Cys Gly Ala Ile Tyr Leu
        115                 120                 125

Pro Pro Asn Thr Gln Ile Asn Glu Ser Pro Arg Ala Glu Leu Ser Val
    130                 135                 140

Thr Glu Arg Thr Leu Glu Pro Pro Thr Gln Ser Pro Ser Pro Pro Pro
145                 150                 155                 160

Arg Leu Ser Gly Gln Leu Gln Gly Leu Val Ile Gly Val Thr Ser Val
                165                 170                 175

Leu Val Gly Val Leu Leu Leu Leu Leu Thr Trp Val Leu Ala Ala
            180                 185                 190

Val Phe Pro Arg Ala Thr Arg Gly Ala Cys Val Cys Gly Ser Glu Asp
        195                 200                 205

Glu Pro Leu Lys Glu Gly Pro Asp Ala Ala Pro Val Phe Thr Leu Asp
    210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
                245                 250                 255

Gly Arg Pro Ala Ser Pro Gly Arg Arg Ala Ser Ala Ser Ser Leu Gln
            260                 265                 270

Gly Ala Gln Pro Pro Ser Pro Glu Asp Gly Pro Gly Leu Trp Pro Leu
        275                 280                 285

<210> SEQ ID NO 107
<211> LENGTH: 870
<212> TYPE: DNA
<213> ORGANISM: Canis familiaris

<400> SEQUENCE: 107
atgagaatgt tagtgtctt tacattcatg gcctactgcc atttgctaaa agcatttacg      60
atcacagttt ctaaggacct gtatgtggta gagtatggtg caatgtgac aatggaatgc     120 aaattcccgg tggaaaaaca gttaaacttg tttgcactaa tcgtctactg ggaaatggag    180
gataaaaaaa ttatacaatt tgtgaatgga aggaagacc tgaaagttca gcacagcagc    240
tacagccaga gggctcagct attgaaggac cagctcttct tggggaaggc tgcgcttcag    300
atcacagatg tgagattgca ggatgcaggg gtttactgct gcttgatcgg ctatggcggt    360
gctgactaca gcggattac tttgaaagtt catgccccgt accgcaacat cagccaaaga    420
atttctgtgg atcctgtcac ctctgaacat gaactaatgt gtcaggctga gggttaccct    480
gaggctgaag tcatctggac aagcagtgac caccgagtcc tgagtggcaa aaccaccatc    540
actaattcca atagggaaga gaagctttc aatgtgacca gcacgctgaa catcaatgca    600
acagctaatg agatttttcta ctgcacttt caaagatcag gtcctgagga aaacaatact    660
gccgagttgg tcatcccaga cgactgccc gttccagcaa gtgagaggac tcatttcatg    720
attctgggac ctttcctgtt gcttcttggt gtagtcctgg cagtcacttt ctgtctaaaa    780
aaacatggga gaatgatgga tgtggaaaaa tgttgcaccc gagataggaa ctcaaagaaa    840
cgaaatgata tacaatttga agagacataa                                      870

<210> SEQ ID NO 108
<211> LENGTH: 289
<212> TYPE: PRT

<213> ORGANISM: Canis familiaris

<400> SEQUENCE: 108

| | | | | | | | | | | | | | | |
|---|---|---|---|---|---|---|---|---|---|---|---|---|---|---|
| Met | Arg | Met | Phe | Ser | Val | Phe | Thr | Phe | Met | Ala | Tyr | Cys | His | Leu | Leu |
| 1 | | | | 5 | | | | | 10 | | | | | 15 | |

| Lys | Ala | Phe | Thr | Ile | Thr | Val | Ser | Lys | Asp | Leu | Tyr | Val | Glu | Tyr |
|---|---|---|---|---|---|---|---|---|---|---|---|---|---|---|
| | | | 20 | | | | | 25 | | | | | 30 | |

| Gly | Gly | Asn | Val | Thr | Met | Glu | Cys | Lys | Phe | Pro | Val | Glu | Lys | Gln | Leu |
|---|---|---|---|---|---|---|---|---|---|---|---|---|---|---|---|
| | | | | 35 | | | | | 40 | | | | | 45 | |

| Asn | Leu | Phe | Ala | Leu | Ile | Val | Tyr | Trp | Glu | Met | Glu | Asp | Lys | Lys | Ile |
|---|---|---|---|---|---|---|---|---|---|---|---|---|---|---|---|
| | 50 | | | | | 55 | | | | | 60 | | | | |

| Ile | Gln | Phe | Val | Asn | Gly | Lys | Glu | Asp | Leu | Lys | Val | Gln | His | Ser | Ser |
|---|---|---|---|---|---|---|---|---|---|---|---|---|---|---|---|
| 65 | | | | | 70 | | | | | 75 | | | | | 80 |

| Tyr | Ser | Gln | Arg | Ala | Gln | Leu | Leu | Lys | Asp | Gln | Leu | Phe | Leu | Gly | Lys |
|---|---|---|---|---|---|---|---|---|---|---|---|---|---|---|---|
| | | | | 85 | | | | | 90 | | | | | 95 | |

| Ala | Ala | Leu | Gln | Ile | Thr | Asp | Val | Arg | Leu | Gln | Asp | Ala | Gly | Val | Tyr |
|---|---|---|---|---|---|---|---|---|---|---|---|---|---|---|---|
| | | | 100 | | | | | 105 | | | | | 110 | | |

| Cys | Cys | Leu | Ile | Gly | Tyr | Gly | Gly | Ala | Asp | Tyr | Lys | Arg | Ile | Thr | Leu |
|---|---|---|---|---|---|---|---|---|---|---|---|---|---|---|---|
| | | | 115 | | | | | 120 | | | | | 125 | | |

| Lys | Val | His | Ala | Pro | Tyr | Arg | Asn | Ile | Ser | Gln | Arg | Ile | Ser | Val | Asp |
|---|---|---|---|---|---|---|---|---|---|---|---|---|---|---|---|
| | 130 | | | | | 135 | | | | | 140 | | | | |

| Pro | Val | Thr | Ser | Glu | His | Glu | Leu | Met | Cys | Gln | Ala | Glu | Gly | Tyr | Pro |
|---|---|---|---|---|---|---|---|---|---|---|---|---|---|---|---|
| 145 | | | | | 150 | | | | | 155 | | | | | 160 |

| Glu | Ala | Glu | Val | Ile | Trp | Thr | Ser | Ser | Asp | His | Arg | Val | Leu | Ser | Gly |
|---|---|---|---|---|---|---|---|---|---|---|---|---|---|---|---|
| | | | | 165 | | | | | 170 | | | | | 175 | |

| Lys | Thr | Thr | Ile | Thr | Asn | Ser | Asn | Arg | Glu | Glu | Lys | Leu | Phe | Asn | Val |
|---|---|---|---|---|---|---|---|---|---|---|---|---|---|---|---|
| | | | 180 | | | | | 185 | | | | | 190 | | |

| Thr | Ser | Thr | Leu | Asn | Ile | Asn | Ala | Thr | Ala | Asn | Glu | Ile | Phe | Tyr | Cys |
|---|---|---|---|---|---|---|---|---|---|---|---|---|---|---|---|
| | | | 195 | | | | | 200 | | | | | 205 | | |

| Thr | Phe | Gln | Arg | Ser | Gly | Pro | Glu | Glu | Asn | Asn | Thr | Ala | Glu | Leu | Val |
|---|---|---|---|---|---|---|---|---|---|---|---|---|---|---|---|
| | 210 | | | | | 215 | | | | | 220 | | | | |

| Ile | Pro | Glu | Arg | Leu | Pro | Val | Pro | Ala | Ser | Glu | Arg | Thr | His | Phe | Met |
|---|---|---|---|---|---|---|---|---|---|---|---|---|---|---|---|
| 225 | | | | | 230 | | | | | 235 | | | | | 240 |

| Ile | Leu | Gly | Pro | Phe | Leu | Leu | Leu | Leu | Gly | Val | Val | Leu | Ala | Val | Thr |
|---|---|---|---|---|---|---|---|---|---|---|---|---|---|---|---|
| | | | | 245 | | | | | 250 | | | | | 255 | |

| Phe | Cys | Leu | Lys | Lys | His | Gly | Arg | Met | Met | Asp | Val | Glu | Lys | Cys | Cys |
|---|---|---|---|---|---|---|---|---|---|---|---|---|---|---|---|
| | | | 260 | | | | | 265 | | | | | 270 | | |

| Thr | Arg | Asp | Arg | Asn | Ser | Lys | Lys | Arg | Asn | Asp | Ile | Gln | Phe | Glu | Glu |
|---|---|---|---|---|---|---|---|---|---|---|---|---|---|---|---|
| | | | 275 | | | | | 280 | | | | | 285 | | |

Thr

<210> SEQ ID NO 109
<211> LENGTH: 423
<212> TYPE: DNA
<213> ORGANISM: Mus musculus

<400> SEQUENCE: 109

```
atgggattca gcaggatctt tctcttcctc ctgtcagtaa ctacaggtgt ccactcccag      60
gcttatctac agcagtctgg ggctgagctg gtgaggcctg ggcctcagt gaagatgtcc      120 tgcaaggctt ttggctacac atttaccagt tacaatatgc actgggtgaa gcagacacct     180
agacagggcc tggaatggat tggaaccatt tatccaggag atggtgacgc ttcctacaat     240
cagaaattcc aggacaaggc cacactgact gttgacaaat cctccagcac agcctacatg     300
cagctcagca gcctgacatc tgaagactct gcggtctatt tctgttcaag ggagtttgcc     360
```

```
gatgcttacc ccattcccc ctttgactac tggggccaag gcaccactct cacagtctcc      420
tca                                                                   423
```

<210> SEQ ID NO 110
<211> LENGTH: 141
<212> TYPE: PRT
<213> ORGANISM: Mus musculus

<400> SEQUENCE: 110

```
Met Gly Phe Ser Arg Ile Phe Leu Phe Leu Leu Ser Val Thr Thr Gly
1               5                   10                  15

Val His Ser Gln Ala Tyr Leu Gln Gln Ser Gly Ala Glu Leu Val Arg
            20                  25                  30

Pro Gly Ala Ser Val Lys Met Ser Cys Lys Ala Phe Gly Tyr Thr Phe
        35                  40                  45

Thr Ser Tyr Asn Met His Trp Val Lys Gln Thr Pro Arg Gln Gly Leu
    50                  55                  60

Glu Trp Ile Gly Thr Ile Tyr Pro Gly Asp Gly Asp Ala Ser Tyr Asn
65                  70                  75                  80

Gln Lys Phe Gln Asp Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ser Arg Glu Phe Ala Asp Ala Tyr Pro Ile Pro Pro Phe
        115                 120                 125

Asp Tyr Trp Gly Gln Gly Thr Thr Leu Thr Val Ser Ser
    130                 135                 140
```

<210> SEQ ID NO 111
<211> LENGTH: 393
<212> TYPE: DNA
<213> ORGANISM: Mus musculus

<400> SEQUENCE: 111

```
atgaagttgc ctgttaggct gttggtgctg attttctgga ttcctgcttc cagtagtgat      60
gttttgatga cccaaactcc actctccctg gttgtcagtc ttggagatca ggcctccatc     120
tcttgcagat ctagtcagag cattgtatat agtaatggaa acacctattt agaatggtac     180
ctgcaaaaac caggccagtc tccaaagctc ctgatttaca aagtttccaa ccgatttttct    240 ggggtcccag acaggttcag tgcagtgga tcaggacag atttcacact caagatcagc      300
agagtggagg ctgaggatct gggagtttat tactgctttc aaggttcaca tgttccgtac     360
acgttcggag gggggaccaa gctggaaata aaa                                  393
```

<210> SEQ ID NO 112
<211> LENGTH: 131
<212> TYPE: PRT
<213> ORGANISM: Mus musculus

<400> SEQUENCE: 112

```
Met Lys Leu Pro Val Arg Leu Leu Val Leu Ile Phe Trp Ile Pro Ala
1               5                   10                  15

Ser Ser Ser Asp Val Leu Met Thr Gln Thr Pro Leu Ser Leu Val Val
            20                  25                  30

Ser Leu Gly Asp Gln Ala Ser Ile Ser Cys Arg Ser Ser Gln Ser Ile
        35                  40                  45
```

```
Val Tyr Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
                100                 105                 110

Phe Gln Gly Ser His Val Pro Tyr Thr Phe Gly Gly Gly Thr Lys Leu
                115                 120                 125

Glu Ile Lys
    130

<210> SEQ ID NO 113
<211> LENGTH: 401
<212> TYPE: PRT
<213> ORGANISM: Artificial Sequence
<220> FEATURE:
<223> OTHER INFORMATION: canine and human

<400> SEQUENCE: 113

Met Asn Phe Leu Leu Ser Trp Val His Trp Ser Leu Ala Leu Leu Leu
1               5                   10                  15

Tyr Leu His His Ala Lys Trp Ser Gln Ala Leu Asp Ser Pro Asp Arg
                20                  25                  30

Pro Trp Ser Pro Leu Thr Phe Ser Pro Ala Gln Leu Thr Val Gln Glu
                35                  40                  45

Gly Glu Asn Ala Thr Phe Thr Cys Ser Leu Ala Asp Ile Pro Asp Ser
    50                  55                  60

Phe Val Leu Asn Trp Tyr Arg Leu Ser Pro Arg Asn Gln Thr Asp Lys
65                  70                  75                  80

Leu Ala Ala Phe Gln Glu Asp Arg Ile Glu Pro Gly Arg Asp Arg Arg
                85                  90                  95

Phe Arg Val Met Arg Leu Pro Asn Gly Arg Asp Phe His Met Ser Ile
                100                 105                 110

Val Ala Ala Arg Leu Asn Asp Ser Gly Ile Tyr Leu Cys Gly Ala Ile
                115                 120                 125

Tyr Leu Pro Pro Asn Thr Gln Ile Asn Glu Ser Pro Arg Ala Glu Leu
    130                 135                 140

Ser Val Thr Glu Arg Thr Leu Glu Pro Pro Thr Gln Ser Pro Ser Pro
145                 150                 155                 160

Pro Pro Arg Leu Ser Gly Gln Leu Gln Gly Leu Val Gly Thr Asp Lys
                165                 170                 175

Thr His Thr Cys Pro Pro Cys Pro Ala Pro Glu Leu Leu Gly Gly Pro
                180                 185                 190

Ser Val Phe Leu Phe Pro Pro Lys Pro Lys Asp Thr Leu Met Ile Ser
                195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
                260                 265                 270
```

```
Tyr Lys Cys Lys Val Ser Asn Lys Ala Leu Pro Ala Pro Ile Glu Lys
            275                 280                 285

Thr Ile Ser Lys Ala Lys Gly Gln Pro Arg Glu Pro Gln Val Tyr Thr
        290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys

<210> SEQ ID NO 114
<211> LENGTH: 11
<212> TYPE: PRT
<213> ORGANISM: Mus musculus

<400> SEQUENCE: 114

Ile Phe Tyr Asp Tyr Asp Gly Asp Ile Asp Val
1               5                   10
```

We claim:

1. An isolated mammalian antibody or an antigen binding fragment thereof, that binds canine Programmed Death Receptor 1 (canine PD-1) with specificity, said antibody comprising a set of six complementary determining regions (CDRs) that comprises three light chain CDRs: CDR light 1 (CDRL1), CDR light 2 (CDRL2), and CDR light 3 (CDRL3); and three heavy chain CDRs: CDR heavy 1 (CDRH1), CDR heavy 2 (CDRH2) and CDR heavy 3 (CDRH3);
   (a) wherein CDRL1 comprises the amino acid sequence of SEQ ID NO: 13;
   (b) wherein CDRL2 comprises the amino acid sequence of SEQ ID NO: 19;
   (c) wherein CDRL3 comprises the amino acid sequence of SEQ ID NO: 25;
   (d) wherein CDRH1 comprises the amino acid sequence of SEQ ID NO: 27;
   (e) wherein CDRH2 comprises the amino acid sequence of SEQ ID NO: 31; and
   (f) wherein CDRH3 comprises the amino acid sequence of SEQ ID NO: 36.

2. The isolated mammalian antibody or antigen binding fragment thereof of claim 1, wherein the mammalian antibody is a murine antibody.

3. The isolated mammalian antibody or antigen binding fragment thereof of claim 2 that is a caninized antibody.

4. The isolated mammalian antibody or antigen binding fragment thereof of claim 3, wherein when bound to canine PD-1, said antibody binds to at least one amino acid residue within SEQ ID NO: 103; wherein the antibody and antigen binding fragment thereof binds canine PD-1 and blocks the binding of canine PD-1 to canine Programmed Death Ligand 1 (PD-L1).

5. The isolated mammalian antibody or antigen binding fragment thereof of claim 4 wherein when bound to canine PD-1 said antibody binds to at least one amino acid residue within one or more amino acid sequences selected from the group consisting of SEQ ID NO: 83, SEQ ID NO: 84, SEQ ID NO: 99, SEQ ID NO: 100, of SEQ ID NO: 101, SEQ ID NO: 102, and SEQ ID NO: 104.

6. The isolated mammalian antibody or antigen binding fragment thereof of claim 5, wherein when bound to canine PD-1 said antibody binds to one or more amino acid residues selected from the group consisting of $R_{62}$, $R_{69}$, $R_{72}$, $R_{75}$, and $R_{90}$ of SEQ ID NO: 2.

7. An isolated nucleic acid that encodes the light chain of the antibody of claim 1.

8. An isolated nucleic acid that encodes the heavy chain of the antibody of claim 1.

9. An isolated nucleic acid that encodes the amino acid sequences of SEQ ID NOs: 27, 31, and 36.

10. An expression vector comprising the isolated nucleic acid of claim 8.

11. A pharmaceutical composition comprising the antibody of claim 4 and a pharmaceutically acceptable carrier or diluent.

12. A method of increasing the activity of an immune cell, comprising administering to a subject in need thereof a therapeutically effective amount of the pharmaceutical composition of claim 11.

13. A pharmaceutical composition comprising the antibody of claim 3 and a pharmaceutically acceptable carrier or diluent.

14. A pharmaceutical composition comprising the antibody of claim 1 and a pharmaceutically acceptable carrier or diluent.

15. An expression vector comprising the isolated nucleic acid of claim 7.

16. A method of increasing the activity of an immune cell, comprising administering to a subject in need thereof a therapeutically effective amount of the pharmaceutical composition of claim 14.

17. A method of increasing the activity of an immune cell, comprising administering to a subject in need thereof a therapeutically effective amount of the pharmaceutical composition of claim 13.

* * * * *